United States Patent
Celiz et al.

(10) Patent No.: US 11,224,679 B2
(45) Date of Patent: Jan. 18, 2022

(54) METHODS AND COMPOSITIONS FOR DENTAL TISSUE REPAIR AND/OR REGENERATION

(71) Applicant: President and Fellows of Harvard College, Cambridge, MA (US)

(72) Inventors: Adam D. Celiz, Dorchester, MA (US); Kyle Holmberg Vining, Brookline, MA (US); David J. Mooney, Sudbury, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/082,808

(22) PCT Filed: Mar. 8, 2017

(86) PCT No.: PCT/US2017/021324
§ 371 (c)(1),
(2) Date: Sep. 6, 2018

(87) PCT Pub. No.: WO2017/156102
PCT Pub. Date: Sep. 14, 2017

(65) Prior Publication Data
US 2019/0091373 A1    Mar. 28, 2019

Related U.S. Application Data

(60) Provisional application No. 62/305,733, filed on Mar. 9, 2016.

(51) Int. Cl.
| | | |
|---|---|---|
| *A61L 27/38* | (2006.01) | |
| *A61L 27/16* | (2006.01) | |
| *A61L 27/52* | (2006.01) | |
| *A61K 31/27* | (2006.01) | |
| *A61K 35/32* | (2015.01) | |
| *A61K 31/215* | (2006.01) | |
| *A61K 31/225* | (2006.01) | |
| *A61K 6/54* | (2020.01) | |
| *A61C 5/00* | (2017.01) | |
| *C08L 5/00* | (2006.01) | |
| *C08L 33/10* | (2006.01) | |
| *C08L 67/04* | (2006.01) | |

(52) U.S. Cl.
CPC ............ *A61L 27/3834* (2013.01); *A61K 6/54* (2020.01); *A61K 31/215* (2013.01); *A61K 31/225* (2013.01); *A61K 31/27* (2013.01); *A61K 35/32* (2013.01); *A61L 27/16* (2013.01); *A61L 27/52* (2013.01); *A61C 5/00* (2013.01); *A61L 2430/12* (2013.01); *C08L 5/00* (2013.01); *C08L 33/10* (2013.01); *C08L 67/04* (2013.01); *C08L 2203/02* (2013.01)

(58) Field of Classification Search
CPC .......... A61K 6/54; A61K 31/27; A61K 35/32; A61K 31/225; A61K 31/215; C08L 67/04; C08L 33/10; C08L 2203/02; C08L 5/00; C08L 33/08; A61C 5/00; A61L 2430/12; A61L 27/16; A61L 27/3834; A61L 27/52
See application file for complete search history.

(56) References Cited

U.S. PATENT DOCUMENTS

| | | | |
|---|---|---|---|
| 3,835,090 A * | 9/1974 | Gander et al. .......... | C08K 3/013 523/116 |
| 2005/0079470 A1 | 4/2005 | Rutherford et al. | |
| 2009/0270527 A1 * | 10/2009 | Lin ........................ | A61K 6/887 523/116 |
| 2012/0164604 A1 | 6/2012 | Nakashima et al. | |
| 2012/0189668 A1 | 7/2012 | Whitson | |
| 2013/0115573 A1 | 5/2013 | Lampl | |

FOREIGN PATENT DOCUMENTS

| | | |
|---|---|---|
| KR | 10-0911843 B1 | 8/2009 |
| WO | 2006/116530 A2 | 11/2006 |
| WO | 2008/147366 A1 | 12/2008 |

OTHER PUBLICATIONS https://pubchem.ncbi.nlm.nih.gov/substance/237355416, Retrieved Sep. 16, 2019.*
Chen et al., In vitro and in vivo characterization of pentaerythritol triacrylate-co-trimethylolpropane nanocomposite scaffolds as potential bone augments and grafts. Tissue Eng Part A. Jan. 2015;21(1-2):320-31.
Pubchem, SCHEMBL12264264, PubChem SID: 237355416. Retrieved online at: https:/.pubchem.ncbi.nlm.nih.gov/substance/237355416. 7 pages, Feb. 13, 2015.
International Search Report and Written Opinion for Application No. PCT/US2017/021324, dated May 25, 2017, 20 pages.
Supplementary European Search Report for Application No. 17763983. 8, dated Oct. 11, 2019, 9 pages.

* cited by examiner

*Primary Examiner* — Lezah Roberts
(74) *Attorney, Agent, or Firm* — McCarter & English, LLP; Maria Laccotripe Zacharakis

(57) ABSTRACT

The present invention provides methods and compositions for promoting dental tissue repair and/or regeneration, methods for promoting differentiation of dental pulp stem cells, methods for treating periodontal diseases, and methods for treating infection of a dental pulp in a subject in need thereof by contacting the tissue with a composition comprising a triacrylate capable of promoting dental pulp stem cells adhesion and/or proliferation.

19 Claims, 31 Drawing Sheets

AT03 – trimethylolpropane triacrylate

Day 21

N = 6, +/- SEM, Two-way ANOVA with Tukey post-hoc test, alpha = 0.05

METHODS AND COMPOSITIONS FOR DENTAL TISSUE REPAIR AND/OR REGENERATION

RELATED APPLICATION

This application is a 35 U.S.C. § 371 national stage filing of International Application No. PCT/US2017/021324, filed on Mar. 8, 2017, which in turn claims the benefit of priority to U.S. Provisional Application No. 62/305,733, filed on Mar. 9, 2016. The entire contents of each of the foregoing applications are incorporated herein by reference.

GOVERNMENT SUPPORT

This invention was made with government support under DE013033 and under DE025292 awarded by the National Institutes of Health. The government has certain rights in this invention.

BACKGROUND OF THE INVENTION

Dental diseases such as caries and periodontal diseases have historically been considered the most important global oral health burdens. In fact, dental caries is still a major oral health problem in most industrialized countries, affecting 60-90% of school-age children and the vast majority of adults. The overall economic cost of dental procedures is up to thousands of dollars per tooth over the course of a patient's life, and the gross domestic cost of endodontic procedures alone in the U.S. is estimated to total $8.2 billion annually (Brown L J, N. K., Johns B A, Warren M (2003) *ADA Health Policy Resources Center Dental Health Policy Analysis Series*; American Dental Association Survey Center (2002) American Dental Association). The global economic burden of dental disease was estimated to be $442 billion in 2010 (Listl S. et al., 2015 *Journal of Dental Research* 94(10): 1355-1361). Thus, the development of reliable and affordable therapeutic strategies for treating dental diseases is an area of active investigation.

A tooth is biologically viable largely because of the dental pulp. Dental pulp is a delicate connective tissue interspersed with tiny blood vessels, lymphatics, nerves, and undifferentiated connective tissue cells. Like other connective tissues throughout the body, it reacts to bacterial infection or to other stimuli by an inflammatory response known as pulpitis, which is the most common cause of toothache. Most cases of pulpitis are primarily a result of dental caries in which bacteria or their products invade the dentin and pulp tissue. The breakdown of enamel by bacteria can result in irreversible damage to the dentin and dental pulp.

Dental infections into the pulp are treated primarily by endodontic surgery such as root canal therapy. After removal of the native tooth pulp, synthetic materials are injected to fill the root canal. Although endodontic or root canal treatment has been the conventional state of the art of contemporary dentistry, it has several deficiencies that negatively affect the quality of life of the patient (Salvi et al., 2007 *Int Enclod J.* 40(3): 209-15). For example, root canal-treated teeth tend to be brittle, and susceptible to fracture. In addition, discoloration frequently takes place following root canal treatment. Patients whose root canal treated teeth have undergone discoloration often require additional and costly cosmetic dental procedures. Root canal treatment is not suitable for all infected teeth. In particular, diseased, missing or infected tooth pulp of baby teeth often lacks treatment options and is frequently not suitable for root canal treatment. Untreated or poorly managed dental infections may result in dental pulp injury and infection, which causes pain and may also cause systemic infections (Shay, 2002 *Clin Infect Dis.* 34(9): 1215-23; Brennan et al., 2007 *J Am. Dent. Assoc.* 138(1): 80-85). Currently, there are no alternatives to root canal therapy for restoring infected teeth.

Accordingly, there remains an ongoing and unmet need for the development of novel therapeutic strategies to promote dental tissue repair and regeneration and to treat dental diseases.

SUMMARY OF THE INVENTION

The present invention is based, at least in part, on the discovery that certain novel therapeutic biomaterials are compatible with dental pulp stem cells and are capable of promoting dentin and/or dental pulp repair and/or regeneration. In particular, the present inventors have surprisingly discovered that, in contrast to methyacrylates and other acrylates, such as diacrylates, triacrylates are able to stimulate dental pulp stem cell (DPCS) adhesion, proliferation and differentiation, thus facilitating the regeneration of dentin and/or dental pulp and preserving the vitality of the tooth. Without intending to be limited by theory, it is believed that the use of these therapeutic biomaterials represents a novel strategy that could significantly impact the practice of dentistry and, thus, could establish a new paradigm for improving dental treatments.

Accordingly, in one aspect, the present invention provides compositions for use in dental tissue repair and/or regeneration. The compositions include a triacrylate capable of promoting adhesion and/or proliferation of dental pulp stem cells (DPSCs); and a scaffold.

In some embodiments, the scaffold comprises a particle that encapsulates the composition. In some embodiments, the particle that encapsulates the composition is selected from the group consisting of a microsphere, a liposome, a microparticle, or combinations thereof. In some embodiments, the scaffold comprises a hydrogel. In some embodiments, the hydrogel is selected from the group consisting of collagen, alginate, polysaccharide, gelatin, chitosan, hyaluronic acid (HA), polyethylene glycol (PEG), poly (glycolide) (PGA), poly(L-lactide) (PLA), poly(lactide-co-glycolide) (PLGA), and polylactic-coglycolic acid.

In some embodiments, the triacrylate is selected from the group consisting of trimethylolpropane propoxylate triacrylate, trimethylolpropane triacrylate, pentaerythritol triacrylate, trimethylolpropane ethoxylate triacrylate, succinic acid triacrylate and combinations thereof.

In some embodiments, the triacrylate is trimethylolpropane propoxylate triacrylate. In other embodiments, the triacrylate is trimethylolpropane triacrylate. In some embodiments, the triacrylate is pentaerythritol triacrylate. In other embodiments, the triacrylate is trimethylolpropane ethoxylate triacrylate. In yet another embodiment, the triacrylate is succinic acid triacrylate.

In some embodiments, the triacrylate is modified triacrylate. In some embodiments, the triacrylate is a compound of Formula I, comprising the structure:

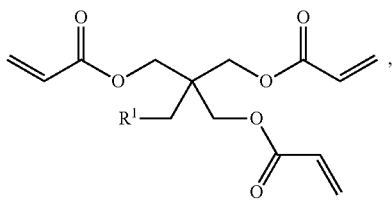

or a pharmaceutically acceptable salt thereof.

In some embodiments, $R^1$ is selected from the group consisting of —COOR$^a$, —OCOR$^a$, —NR$^a$COOR$^a$, —OCON(R$^a$)$_2$, —NR$^b$COR$^a$, —CON(R$^a$)$_2$, —COR$^a$ and —NHCON(R$^a$)$_2$; R$^a$ is selected from the group consisting of hydrogen, C$_1$-C$_{12}$alkyl, C$_1$-C$_{12}$alkoxy, C$_2$-C$_{12}$alkenyl, C$_2$-C$_{12}$alkynyl, C$_3$-C$_{12}$cycloalkyl, C$_2$-C$_{11}$heterocyclyl, C$_6$-C$_{14}$aryl, —N(R$^b$)$_2$, —SR$^b$, and —OR$^b$; wherein the C$_1$-C$_{12}$alkyl, C$_1$-C$_{12}$alkoxy, C$_2$-C$_{12}$alkenyl, C$_2$-C$_{12}$alkynyl, C$_3$-C$_{12}$cycloalkyl, C$_2$-C$_{11}$heterocyclyl, and C$_6$-C$_{14}$aryl groups are optionally substituted with one or four groups selected from the group consisting of hydrogen, halogen, hydroxy, cyano, amino, C$_1$-C$_{12}$alkyl, C$_1$-C$_{12}$alkoxy, C$_1$-C$_{12}$alkenyl, C$_1$-C$_{12}$alkynyl, C$_3$-C$_{12}$cycloalkyl, C$_2$-C$_{11}$heterocyclyl, C$_6$-C$_{14}$aryl, C$_1$-C$_{12}$alkylamino, di(C$_1$-C$_{12}$alkyl)amino, —COOR$^c$, —OCOR$^c$, —NR$^c$COOR$^c$, —OCON(R$^c$)$_2$, —NR$^c$COR$^c$, —CON(R$^c$)$_2$, —COR$^c$ and —NHCON(R$^c$)$_2$; R$^b$ is independently selected from the group consisting of hydrogen, C$_1$-C$_{12}$alkyl, C$_1$-C$_{12}$alkoxy, C$_2$-C$_{12}$alkenyl, C$_2$-C$_{12}$alkynyl, C$_3$-C$_{12}$cycloalkyl, C$_6$-C$_{14}$aryl, and C$_2$-C$_{11}$heterocyclyl, or wherein the two R$^b$ groups may form a heterocyclyl with the nitrogen, oxygen, or sulfur to which they are connected, wherein the C$_1$-C$_{12}$alkyl, C$_1$-C$_{12}$alkoxy, C$_2$-C$_{12}$alkenyl, C$_2$-C$_{12}$alkynyl, C$_3$-C$_{12}$cycloalkyl, C$_6$-C$_{14}$aryl, and C$_2$-C$_{11}$heterocyclyl are optionally substituted by one of more groups selected from halogen, hydroxy, amino, carboxy, C$_1$-C$_6$alkyl, C$_1$-C$_4$ carbonylamino, and C$_1$-C$_4$ alkoxy; and R$^c$ is independently selected from the group consisting of hydrogen, C$_1$-C$_{12}$alkyl, C$_1$-C$_{12}$alkoxy, C$_2$-C$_{12}$alkenyl, C$_2$-C$_{12}$alkynyl, C$_3$-C$_{12}$cycloalkyl, C$_6$-C$_{14}$aryl, and C$_2$-C$_{11}$heterocyclyl, or wherein the two R$^c$ groups may form a heterocyclyl with the nitrogen or sulfur to which they are connected, wherein the C$_1$-C$_{12}$alkyl, C$_1$-C$_{12}$alkoxy, C$_2$-C$_{12}$alkenyl, C$_2$-C$_{12}$alkynyl, C$_3$-C$_{12}$cycloalkyl, C$_6$-C$_{14}$aryl, and C$_2$-C$_{11}$heterocyclyl are optionally substituted by one of more groups selected from halogen, hydroxy, amino, carboxy, C$_1$-C$_6$alkyl, C$_1$-C$_4$ carbonylamino, and C$_1$-C$_4$ alkoxy.

In some embodiments, $R^1$ is —OCON(R$^a$)$_2$; wherein R$^a$ is selected from the group consisting of hydrogen and C$_1$-C$_8$alkyl; wherein the C$_1$-C$_6$alkyl is optionally substituted by one or four groups selected from halogen, hydroxy, amino, carboxy, C$_1$-C$_6$alkyl, C$_1$-C$_4$ carbonylamino, and C$_1$-C$_4$ alkoxy.

In some embodiments, the compound is of the following structural formula, or a pharmaceutically acceptable salt thereof;

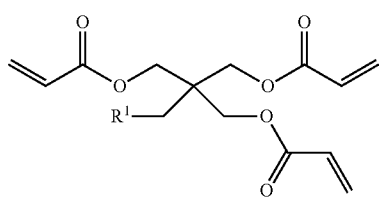

[Formula I]

wherein $R^1 =$ 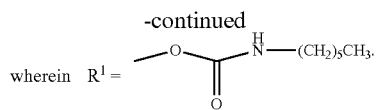

In some embodiments, $R^1$ is —OCOR$^a$; wherein R$^a$ is selected from the group consisting of hydrogen, C$_1$-C$_{12}$alkyl, C$_1$-C$_{12}$alkoxy, C$_2$-C$_{12}$alkenyl, C$_2$-C$_{12}$alkynyl, C$_3$-C$_{12}$cycloalkyl, C$_2$-C$_{11}$heterocyclyl, C$_6$-C$_{14}$aryl, —N(R$^b$)$_2$, —SR$^b$, and —OR$^b$; wherein the C$_1$-C$_{12}$alkyl, C$_1$-C$_{12}$alkoxy, C$_2$-C$_{12}$alkenyl, C$_2$-C$_{12}$alkynyl, C$_3$-C$_{12}$cycloalkyl, C$_2$-C$_{11}$heterocyclyl, and C$_6$-C$_{14}$aryl groups are optionally substituted with one or four groups selected from the group consisting of hydrogen, halogen, hydroxy, cyano, amino, C$_1$-C$_{12}$alkyl, C$_1$-C$_{12}$alkoxy, C$_1$-C$_{12}$alkenyl, C$_1$-C$_{12}$alkynyl, C$_3$-C$_{12}$cycloalkyl, C$_2$-C$_{11}$heterocyclyl, C$_6$-C$_{14}$aryl, C$_1$-C$_{12}$alkylamino, di(C$_1$-C$_{12}$alkyl)amino, —COOR$^a$, —OCOR$^a$, —NR$^a$COOR$^a$, —OCON(R$^a$)$_2$, —NR$^a$COR$^a$, —CON(R$^a$)$_2$, —COR$^a$ and —NHCON(R$^a$)$_2$; wherein R$^b$ is independently selected from the group consisting of hydrogen, C$_1$-C$_{12}$alkyl, C$_1$-C$_{12}$alkoxy, C$_2$-C$_{12}$alkenyl, C$_2$-C$_{12}$alkynyl, C$_3$-C$_{12}$cycloalkyl, C$_6$-C$_{14}$aryl, and C$_2$-C$_{11}$heterocyclyl, or wherein the two R$^b$ groups may form a heterocyclyl with the nitrogen, oxygen, or sulfur to which they are connected, wherein the C$_1$-C$_{12}$alkyl, C$_1$-C$_{12}$alkoxy, C$_2$-C$_{12}$alkenyl, C$_2$-C$_{12}$alkynyl, C$_3$-C$_{12}$cycloalkyl, C$_6$-C$_{14}$aryl, and C$_2$-C$_{11}$heterocyclyl are optionally substituted by one of more groups selected from halogen, hydroxy, amino, carboxy, C$_1$-C$_6$alkyl, C$_1$-C$_4$ carbonylamino, and C$_1$-C$_4$ alkoxy; and R$^a$ is independently selected from the group consisting of hydrogen, halogen, C$_1$-C$_{12}$alkyl, C$_1$-C$_{12}$alkenyl, C$_1$-C$_{12}$alkynyl, C$_3$-C$_{12}$cycloalkyl, C$_2$-C$_{11}$heterocyclyl, and C$_6$-C$_{14}$aryl; wherein the C$_1$-C$_{12}$alkyl, C$_1$-C$_{12}$alkenyl, C$_1$-C$_{12}$alkynyl, C$_3$-C$_{12}$cycloalkyl, C$_2$-C$_{11}$heterocyclyl, and C$_6$-C$_{14}$aryl are optionally substituted from the group consisting of hydrogen, halogen, hydroxy, amino, carboxy, C$_1$-C$_4$ carbonylamino, and C$_1$-C$_4$ alkoxy.

In some embodiments, the compound is of the following structural formula,

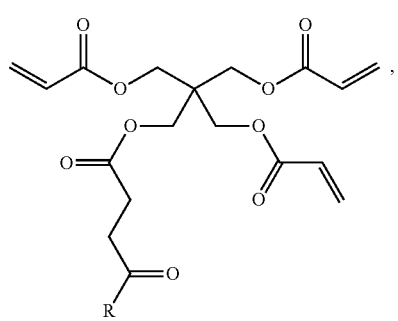

[Formula II]

or a pharmaceutical salt thereof; wherein R is selected from the group consisting of hydrogen, bromo, iodo, fluoro, C$_1$-C$_{12}$alkyl, C$_2$-C$_{12}$alkenyl, C$_2$-C$_{12}$alkynyl, C$_3$-C$_{12}$cycloalkyl, C$_2$-C$_{11}$heterocyclyl, C$_6$-C$_{14}$aryl, —N(R$^d$)$_2$, —SR$^d$, and —OR$^e$; wherein the C$_1$-C$_{12}$alkyl, C$_2$-C$_{12}$alkenyl, C$_2$-C$_{12}$alkynyl, C$_3$-C$_{12}$cycloalkyl, C$_2$-C$_{11}$heterocyclyl, and C$_6$-C$_{14}$aryl groups are optionally substituted by one or more groups selected from the group consisting of halogen, hydroxy, cyano, amino, C$_1$-C$_{12}$alkyl, C$_1$-C$_{12}$alkenyl, C$_1$-C$_{12}$alkynyl, C$_1$-C$_{12}$alkoxy, $C_3$-$C_{12}$cycloalkyl, $C_2$-$C_{11}$heterocyclyl, $C_6$-$C_{14}$aryl, $C_1$-$C_{12}$alkylamino, and di($C_1$-$C_{12}$alkyl)amino; $R^d$ is independently selected from the group consisting of hydrogen, $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two $R^d$ groups may form a heterocyclyl with the nitrogen to which they are connected, wherein the $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, and $C_1$-$C_4$ alkoxy; and $R^e$ is independently selected from the group consisting of $C_2$-$C_{12}$alkyl, $C_2$-$C_{12}$alkenyl, $C_2$-$C_{12}$alkynyl, benzyl, and phenyl, wherein the $C_2$-$C_{12}$alkyl, $C_2$-$C_{12}$alkenyl, $C_2$-$C_{12}$alkynyl, benzyl, and phenyl are optionally substituted from the group consisting of halogen, hydroxy, and $C_1$-$C_4$ alkoxy.

In some embodiments, the compound is of the following structural formula, or a pharmaceutically acceptable salt thereof;

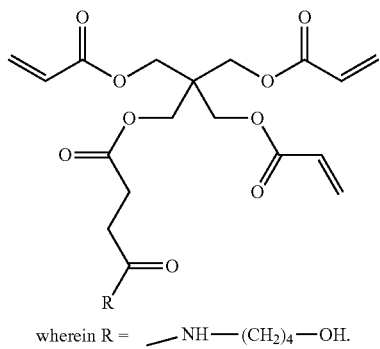

[Formula II]

wherein R = $\underset{}{\diagup}$NH—(CH$_2$)$_4$—OH.

In some embodiments, modification of the triacrylate increases the ability of the triacrylate to promote adhesion and/or proliferation of dental pulp stem cells (DPSCs). In other embodiments, modification of the triacrylate increases the ability of the triacrylate to promote dental tissue repair and/or regeneration.

In some embodiments, the composition further comprises a plurality of dental pulp stem cells (DPSCs).

In one aspect, the present invention provides compounds of formula II, comprising the structure:

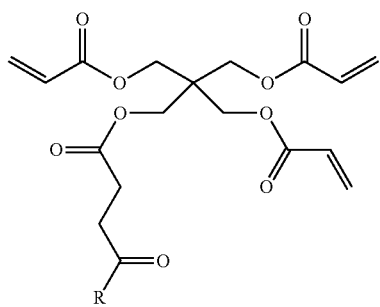

[Formula II]

or a pharmaceutically acceptable salt thereof; wherein R is selected from the group consisting of hydrogen, bromo, iodo, fluoro, $C_1$-$C_{12}$alkyl, $C_2$-$C_{12}$alkenyl, $C_2$-$C_{12}$alkynyl, $C_3$-$C_{12}$cycloalkyl, $C_2$-$C_{11}$heterocyclyl, $C_6$-$C_{14}$aryl, —N($R^d$)$_2$, —S$R^d$, and —O$R^e$; wherein the $C_1$-$C_{12}$alkyl, $C_2$-$C_{12}$alkenyl, $C_2$-$C_{12}$alkynyl, $C_3$-$C_{12}$cycloalkyl, $C_2$-$C_{11}$heterocyclyl, and $C_6$-$C_{14}$aryl groups are optionally substituted by one or more groups selected from the group consisting of halogen, hydroxy, cyano, amino, $C_1$-$C_{12}$alkyl, $C_1$-$C_{12}$alkenyl, $C_1$-$C_{12}$alkynyl, $C_1$-$C_{12}$alkoxy, $C_3$-$C_{12}$cycloalkyl, $C_2$-$C_{11}$heterocyclyl, $C_6$-$C_{14}$aryl, $C_1$-$C_{12}$alkylamino, and di($C_1$-$C_{12}$alkyl)amino; $R^d$ is independently selected from the group consisting of hydrogen, $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two $R^d$ groups may form a heterocyclyl with the nitrogen to which they are connected, wherein the $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, and $C_1$-$C_4$ alkoxy; and $R^e$ is independently selected from the group consisting of $C_2$-$C_{12}$alkyl, $C_2$-$C_{12}$alkenyl, $C_2$-$C_{12}$alkynyl, benzyl, and phenyl, wherein the $C_2$-$C_{12}$alkyl, $C_2$-$C_{12}$alkenyl, $C_2$-$C_{12}$alkynyl, benzyl, and phenyl are optionally substituted from the group consisting of halogen, hydroxy, and $C_1$-$C_4$ alkoxy.

In some embodiments, R is selected from the groups consisting of hydrogen, bromo, iodo, fluoro, $C_1$-$C_6$alkyl, $C_2$-$C_6$alkenyl, $C_2$-$C_6$alkynyl, $C_3$-$C_8$cycloalkyl, $C_2$-$C_6$heterocyclyl, $C_6$-$C_{12}$aryl, —N($R^d$)$_2$, —S$R^d$, and —O$R^e$; wherein $C_1$-$C_6$alkyl, $C_2$-$C_6$alkenyl, $C_2$-$C_6$alkynyl, $C_3$-$C_6$cycloalkyl, $C_2$-$C_6$heterocyclyl, $C_6$-$C_{12}$aryl are optionally substituted by one to four groups selected from halogen, hydroxy, and $C_1$-$C_4$ alkoxy; $R^d$ is independently selected from the groups consisting of hydrogen, $C_1$-$C_6$alkyl, $C_3$-$C_8$cycloalkyl, $C_6$-$C_{14}$aryl, and $C_2$-$C_{11}$heterocyclyl, wherein the $C_1$-$C_6$alkyl, $C_3$-$C_8$cycloalkyl, $C_6$-$C_{14}$aryl, and $C_2$-$C_{11}$heterocyclyl are optionally substituted by one of more groups selected from halogen, hydroxy, and $C_1$-$C_4$ alkoxy; and $R^e$ is independently selected from the groups consisting of $C_2$-$C_6$alkyl, benzyl, and phenyl, the $C_2$-$C_6$alkyl, benzyl, and phenyl are optionally substituted from the groups consisting of halogen, hydroxy, and $C_1$-$C_4$ alkoxy.

In some embodiments, R is selected from the group consisting of hydrogen, $C_1$-$C_{12}$alkyl, $C_2$-$C_{12}$alkenyl, $C_2$-$C_{12}$alkynyl, $C_3$-$C_{12}$cycloalkyl, $C_2$-$C_{11}$heterocyclyl, $C_6$-$C_{14}$aryl, —N($R^d$)$_2$, —S$R^d$, and —O$R^e$; wherein the $C_1$-$C_{12}$alkyl, $C_2$-$C_{12}$alkenyl, $C_2$-$C_{12}$alkynyl, $C_3$-$C_{12}$cycloalkyl, $C_2$-$C_{11}$heterocyclyl, and $C_6$-$C_{14}$aryl groups are optionally substituted by one or more groups selected from the group consisting of halogen, hydroxy, cyano, amino, $C_1$-$C_{12}$alkyl, $C_1$-$C_{12}$alkenyl, $C_1$-$C_{12}$alkynyl, $C_1$-$C_{12}$alkoxy, $C_3$-$C_{12}$cycloalkyl, $C_2$-$C_{11}$heterocyclyl, $C_6$-$C_{14}$aryl, $C_1$-$C_{12}$alkylamino, and di($C_1$-$C_{12}$alkyl)amino; $R^d$ is independently selected from the group consisting of hydrogen, $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two $R^d$ groups may form a heterocyclyl with the nitrogen to which they are connected, wherein the $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, and $C_1$-$C_4$ alkoxy; and $R^e$ is independently selected from the group consisting of $C_2$-$C_{12}$alkyl, $C_2$-$C_{12}$alkenyl, $C_2$-$C_{12}$alkynyl, benzyl, and phenyl, wherein the $C_2$-$C_{12}$alkyl, $C_2$-$C_{12}$alkenyl, $C_2$-$C_{12}$alkynyl, benzyl, and phenyl are optionally substituted from the group consisting of halogen, hydroxy, and $C_1$-$C_4$ alkoxy.

In some embodiments, R is selected from the group consisting of hydrogen, $C_1$-$C_{12}$alkyl, —N($R^d$)$_2$, —S$R^d$, and —O$R^e$; wherein the $C_1$-$C_{12}$alkyl is optionally substituted by one or more groups selected from the group consisting of halogen, hydroxy, cyano, amino, $C_1$-$C_{12}$alkyl, $C_1$-$C_{12}$alkylamino, and di($C_1$-$C_{12}$alkyl)amino; $R^d$ is independently selected from the group consisting of hydrogen and $C_1$-$C_{12}$alkyl, or wherein the two $R^d$ groups may form a heterocyclyl with the nitrogen to which they are connected, wherein the $C_1$-$C_{12}$alkyl is optionally substituted by one of more groups selected from halogen, hydroxy, and $C_1$-$C_4$ alkoxy; and $R^e$ is independently selected from the group consisting of $C_2$-$C_{12}$alkyl, benzyl, and phenyl, wherein the $C_2$-$C_{12}$alkyl, benzyl, and phenyl are optionally substituted from the group consisting of halogen, hydroxy, and $C_1$-$C_4$ alkoxy.

In some embodiments, the aryl is anthracenyl, naphthyl, and phenyl.

In some embodiments, the heterocyclyl is aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydropyranyl, imidazolinyl, dihydropyranyl, azirinyl, oxirenyl, thiirenyl, diazirinyl, azetyl, oxetyl, thietyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, thiazepinyl 3-azabicyclo[3.1.0]hexanyl, 3-azabicyclo[3.1.1]heptanyl, 2-azaspiro[3.3]heptanyl, 2-oxa-6-azaspiro[3.3]heptanyl, or 5-azaspiro [2.3]hexanyl.

In another aspect, the present invention provides a compound of formula III, comprising the structure:

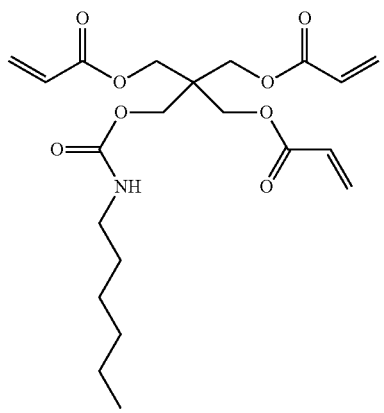

[formula III]

or a pharmaceutically acceptable salt thereof.

In yet another aspect, the present invention provides a compound of formula IV, comprising the structure:

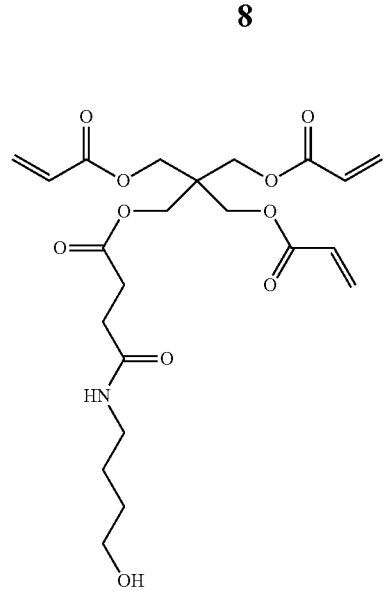

[formula IV]

or a pharmaceutically acceptable salt thereof.

The present of invention further provides compositions for use in dental tissue repair and/or regeneration comprising the compounds having the structural formula II, III and IV, as described herein.

The present invention also provides compositions comprising the compounds having the structural formula II, III and IV, as described herein.

In some embodiments, the triacrylate is polymerized triacrylate. In other embodiments, the triacrylate is polymerized by ultraviolet (UV) irradiation.

In some embodiments, the dental tissue is a dental pulp tissue. In other embodiments, the dental tissue is a dentin tissue.

In some embodiments, the composition further promotes migration and/or differentiation of DPSCs.

In some embodiments, the composition is suitable for treating a dental pulp infection. In other embodiments, the composition is suitable for delivering to a natural or artificial cavity or chamber of a tooth in a subject. In some embodiments, the composition is delivered by injection.

In one aspect, the present invention provides methods for promoting dental tissue repair and/or regeneration in a subject in need thereof. The methods include contacting the dental tissue with a composition comprising a triacrylate capable of promoting adhesion and/or proliferation of dental pump stem cells (DPSCs); and allowing DPSCs to adhere to the composition and proliferate, thereby promoting repair and/or regeneration of the dental tissue.

In some embodiments, the dental tissue is a dental pulp tissue. In other embodiments, the dental tissue is a dentin tissue. In some embodiments, the dental tissue is selected from the group consisting of a dental pulp tissue, a coronal pulp tissue, a radicular pulp tissue, a dentin tissue, a periapical tissue, a periapical connective tissue, a periodontal tissue, an accessory canal tissue, an apical foramen tissue, a foramina tissue, an odontoblastic layer, a bone tissue, a gum tissue, a blood vessel tissue, a nerve tissue, a cementum tissue, a neodentin tissue, and tissues associated with dental pulp comprising any of ameloblasts, fibroblasts, odontoblasts, histiocytes, macrophage, granulocytes mast cells or plasma cells.

In some embodiments, the triacrylate is selected from the group consisting of trimethylolpropane propoxylate triacrylate, trimethylolpropane triacrylate, pentaerythritol triacrylate, trimethylolpropane ethoxylate triacrylate, succinic acid triacrylate and combinations thereof.

In some embodiments, the triacrylate is trimethylolpropane propoxylate triacrylate. In other embodiments, the triacrylate is trimethylolpropane triacrylate. In some embodiments, the triacrylate is pentaerythritol triacrylate. In other embodiments, the triacrylate is trimethylolpropane ethoxylate triacrylate. In yet another embodiment, the triacrylate is succinic acid triacrylate.

In some embodiments, the triacrylate is modified triacrylate. In some embodiments, the triacrylate is a compound of Formula I, comprising the structure:

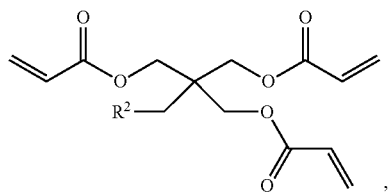

[Formula I]

or a pharmaceutically acceptable salt thereof.

In some embodiments, $R^1$ is selected from the group consisting of —COOR$^a$, —OCOR$^a$, —NR$^a$COOR$^a$, —OCON(R$^a$)$_2$, —NR$^b$COR$^a$, —CON(R$^a$)$_2$, —COR$^a$ and —NHCON(R$^a$)$_2$; R$^a$ is selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_2$-$C_{11}$heterocyclyl, $C_6$-$C_{14}$aryl, —N(R$^b$)$_2$, —SR$^b$, and —OR$^b$; wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_2$-$C_{11}$heterocyclyl, and $C_6$-$C_{14}$aryl groups are optionally substituted with one or four groups selected from the group consisting of hydrogen, halogen, hydroxy, cyano, amino, $C_1$-$C_{12}$alkyl, $C_1$-$C_{12}$alkoxy, $C_1$-$C_{12}$alkenyl, $C_1$-$C_{12}$alkynyl, $C_3$-$C_{12}$cycloalkyl, $C_2$-$C_{11}$heterocyclyl, $C_6$-$C_{14}$aryl, $C_1$-$C_{12}$alkylamino, di($C_1$-$C_{12}$alkyl)amino, —COOR$^c$, —OCOR$^c$, —NR$^c$COOR$^c$, —OCON(R$^c$)$_2$, —NR$^c$COR$^c$, —CON(R$^c$)$_2$, —COR$^c$ and —NHCON(R$^c$)$_2$; R$^b$ is independently selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two R$^b$ groups may form a heterocyclyl with the nitrogen, oxygen, or sulfur to which they are connected, wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, amino, carboxy, $C_1$-$C_6$alkyl, $C_1$-$C_4$ carbonylamino, and $C_1$-$C_4$ alkoxy; and R$^c$ is independently selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two R$^c$ groups may form a heterocyclyl with the nitrogen or sulfur to which they are connected, wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, amino, carboxy, $C_1$-$C_6$alkyl, $C_1$-$C_4$ carbonylamino, and $C_1$-$C_4$ alkoxy.

In some embodiments, $R^1$ is —OCON(R$^a$)$_2$; wherein R$^a$ is selected from the group consisting of hydrogen and $C_1$-$C_8$alkyl; wherein the $C_1$-$C_6$alkyl is optionally substituted by one or four groups selected from halogen, hydroxy, amino, carboxy, $C_1$-$C_6$alkyl, $C_1$-$C_4$ carbonylamino, and $C_1$-$C_4$ alkoxy.

In some embodiments, the compound is of the following structural formula, or a pharmaceutically acceptable salt thereof;

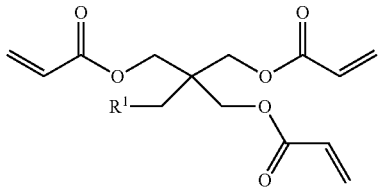

[Formula I]

wherein $R^1 =$ —O—C(=O)—N(H)—(CH$_2$)$_5$CH$_3$.

In some embodiments, $R^1$ is —OCOR$^a$; wherein R$^a$ is selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_1$-$C_{11}$heterocyclyl, $C_6$-$C_{14}$aryl, —N(R$^b$)$_2$, —SR$^b$, and —OR$^b$; wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_2$-$C_{11}$heterocyclyl, and $C_6$-$C_{14}$aryl groups are optionally substituted with one or four groups selected from the group consisting of hydrogen, halogen, hydroxy, cyano, amino, $C_1$-$C_{12}$alkyl, $C_1$-$C_{12}$alkoxy, $C_1$-$C_{12}$alkenyl, $C_1$-$C_{12}$alkynyl, $C_3$-$C_{12}$cycloalkyl, $C_2$-$C_{11}$heterocyclyl, $C_6$-$C_{14}$aryl, $C_1$-$C_{12}$alkylamino, di($C_1$-$C_{12}$alkyl)amino, —COOR$^c$, —OCOR$^c$, —NR$^c$COOR$^c$, —OCON(R$^a$)$_2$, —NR$^c$COR$^c$, —CON(R$^c$)$_2$, —COR$^c$ and —NHCON(R$^a$)$_2$; wherein R$^b$ is independently selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two R$^b$ groups may form a heterocyclyl with the nitrogen, oxygen, or sulfur to which they are connected, wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, amino, carboxy, $C_1$-$C_6$alkyl, $C_1$-$C_4$ carbonylamino, and $C_1$-$C_4$ alkoxy; and R$^c$ is independently selected from the group consisting of hydrogen, halogen, $C_1$-$C_{12}$alkyl, $C_1$-$C_{12}$alkenyl, $C_1$-$C_{12}$alkynyl, $C_3$-$C_{12}$cycloalkyl, $C_2$-$C_{11}$heterocyclyl, and $C_6$-$C_{14}$aryl; wherein the $C_1$-$C_{12}$alkyl, $C_1$-$C_{12}$alkenyl, $C_1$-$C_{12}$alkynyl, $C_3$-$C_{12}$cycloalkyl, $C_2$-$C_{11}$heterocyclyl, and $C_6$-$C_{14}$aryl are optionally substituted from the group consisting of hydrogen, halogen, hydroxy, amino, carboxy, $C_1$-$C_4$ carbonylamino, and $C_1$-$C_4$ alkoxy.

In some embodiments, the compound is of the following structural formula,

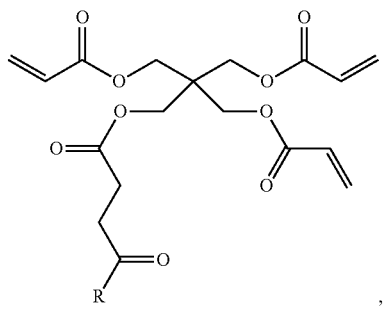

[Formula II]

or a pharmaceutical salt thereof; wherein R is selected from the group consisting of hydrogen, bromo, iodo, fluoro, $C_1$-$C_{12}$alkyl, $C_2$-$C_{12}$alkenyl, $C_2$-$C_{12}$alkynyl, $C_3$-$C_{12}$cycloalkyl, $C_2$-$C_{11}$heterocyclyl, $C_6$-$C_{14}$aryl, —N($R^d$)$_2$, —$SR^d$, and —$OR^e$; wherein the $C_1$-$C_{12}$alkyl, $C_2$-$C_{12}$alkenyl, $C_2$-$C_{12}$alkynyl, $C_3$-$C_{12}$cycloalkyl, $C_2$-$C_{11}$heterocyclyl, and $C_6$-$C_{14}$aryl groups are optionally substituted by one or more groups selected from the group consisting of halogen, hydroxy, cyano, amino, $C_1$-$C_{12}$alkyl, $C_1$-$C_{12}$alkenyl, $C_1$-$C_{12}$alkynyl, $C_1$-$C_{12}$alkoxy, $C_3$-$C_{12}$cycloalkyl, $C_2$-$C_{11}$heterocyclyl, $C_6$-$C_{14}$aryl, $C_1$-$C_{12}$alkylamino, and di($C_1$-$C_{12}$alkyl)amino; $R^d$ is independently selected from the group consisting of hydrogen, $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two $R^d$ groups may form a heterocyclyl with the nitrogen to which they are connected, wherein the $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, and $C_1$-$C_4$ alkoxy; and $R^e$ is independently selected from the group consisting of $C_2$-$C_{12}$alkyl, $C_2$-$C_{12}$alkenyl, $C_2$-$C_{12}$alkynyl, benzyl, and phenyl, wherein the $C_2$-$C_{12}$alkyl, $C_2$-$C_{12}$alkenyl, $C_2$-$C_{12}$alkynyl, benzyl, and phenyl are optionally substituted from the group consisting of halogen, hydroxy, and $C_1$-$C_4$ alkoxy.

In some embodiments, the compound is of the following structural formula, or a pharmaceutically acceptable salt thereof;

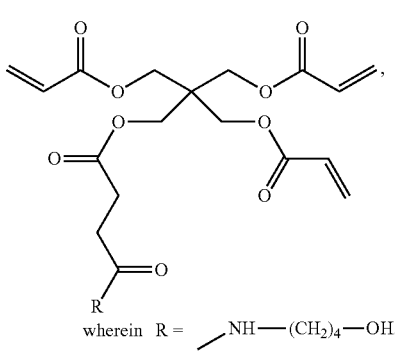

[Formula II]

wherein R = $\diagup$NH—(CH$_2$)$_4$—OH.

In some embodiments, modification of the triacrylate increases the ability of the triacrylate to promote adhesion and/or proliferation of dental pulp stem cells (DPSCs). In other embodiments, modification of the triacrylate increases the ability of the triacrylate to promote dental tissue repair and/or regeneration.

In some embodiments, the triacrylates comprises any compounds as described herein.

In some embodiments, the triacrylate is polymerized prior to contacting the dental tissue. In other embodiments, the triacrylate is polymerized after contacting the dental tissue. In some embodiments, the triacrylate is polymerized by UV irradiation.

In some embodiments, the dental tissue is contacted by delivering the composition into a natural or artificial cavity or chamber of a tooth by injection. In other embodiments, the dental tissue is contacted by delivering the composition into a natural or artificial cavity or chamber of a tooth within a scaffold.

In some embodiments, the scaffold comprises a particle that encapsulates the composition. In other embodiments, the scaffold comprises a hydrogel. In some embodiments, the hydrogel is selected from the group consisting of collagen, alginate, polysaccharide, gelatin, chitosan, hyaluronic acid (HA), polyethylene glycol (PEG), poly(glycolide) (PGA), poly(L-lactide) (PLA), poly(lactide-co-glycolide) (PLGA), and polylactic-coglycolic acid.

In some embodiments, the dental tissue is contacted by delivering the composition into a natural or artificial cavity or chamber of a tooth as a monomer. In other embodiments, the monomer is polymerized after delivery into the natural or artificial cavity or chamber of the tooth by in situ polymerization. In some embodiments, the monomer is polymerized by UV irradiation.

In some embodiments, the composition further promotes migration and/or differentiation of DPSCs.

In some embodiments, the composition comprises a bioactive agent. In other embodiments, the bioactive agent is a compound selected from the group consisting of a chemotactic compound, an osteogenic compound, a dentinogenic compound, an amelogenic compound, an angiogenic compound, and combinations thereof. In certain embodiments, the bioactive agent is an antibiotic or an analgesic.

In some embodiments, the composition further comprises a cell. In other embodiments, the composition is free of a bioactive agent or a cell.

In some embodiments, the subject is a mammal. In other embodiments, the subject is a human.

In one aspect, the present invention provides methods of promoting differentiation of dental pulp stem cells (DPSCs). The methods include contacting the dental pulp stem cells (DPSCs) with a composition comprising a triacrylate capable of promoting adhesion and/or proliferation of DPSCs; and allowing DPSCs to adhere to the composition and proliferate, thereby promoting differentiation of the DPSCs.

In some embodiments, the triacrylate is selected from the group consisting of trimethylolpropane propoxylate triacrylate, trimethylolpropane triacrylate, pentaerythritol triacrylate, trimethylolpropane ethoxylate triacrylate, succinic acid triacrylate and combinations thereof.

In some embodiments, the triacrylate is trimethylolpropane propoxylate triacrylate. In other embodiments, the triacrylate is trimethylolpropane triacrylate. In some embodiments, the triacrylate is pentaerythritol triacrylate. In other embodiments, the triacrylate is trimethylolpropane ethoxylate triacrylate. In yet another embodiment, the triacrylate is succinic acid triacrylate.

In some embodiments, the triacrylate is modified triacrylate. In some embodiments, the triacrylate is a compound of Formula I, comprising the structure:

[Formula I]

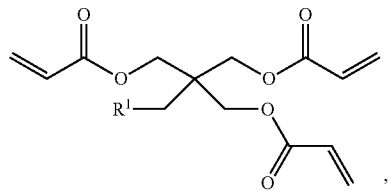 [SMILES: C=CC(=O)OCC(CC)(COC(=O)C=C)COC(=O)C=C]

or a pharmaceutically acceptable salt thereof.

In some embodiments, $R^1$ is selected from the group consisting of —COOR$^a$, —OCOR$^a$, —NR$^a$COOR$^a$, —OCON(R$^a$)$_2$, —NR$^b$COR$^a$, —CON(R$^a$)$_2$, —COR$^a$ and —NHCON(R$^a$)$_2$; R$^a$ is selected from the group consisting of hydrogen, C$_1$-C$_{12}$alkyl, C$_1$-C$_{12}$alkoxy, C$_2$-C$_{12}$alkenyl, C$_2$-C$_{12}$alkynyl, C$_3$-C$_{12}$cycloalkyl, C$_2$-C$_{11}$heterocyclyl, C$_6$-C$_{14}$aryl, —N(R$^b$)$_2$, —SR$^b$, and —OR$^b$; wherein the C$_1$-C$_{12}$alkyl, C$_1$-C$_{12}$alkoxy, C$_2$-C$_{12}$alkenyl, C$_2$-C$_{12}$alkynyl, C$_3$-C$_{12}$cycloalkyl, C$_2$-C$_{11}$heterocyclyl, and C$_6$-C$_{14}$aryl groups are optionally substituted with one or four groups selected from the group consisting of hydrogen, halogen, hydroxy, cyano, amino, C$_1$-C$_{12}$alkyl, C$_1$-C$_{12}$alkoxy, C$_1$-C$_{12}$alkenyl, C$_1$-C$_{12}$alkynyl, C$_3$-C$_{12}$cycloalkyl, C$_2$-C$_{11}$heterocyclyl, C$_6$-C$_{14}$aryl, C$_1$-C$_{12}$alkylamino, di(C$_1$-C$_{12}$alkyl)amino, —COOR$^c$, —OCOR$^c$, —NR$^c$COOR$^c$, —OCON(R$^c$)$_2$, —NR$^c$COR$^c$, —CON(R$^c$)$_2$, —COR$^c$ and —NHCON(R$^c$)$_2$; R$^b$ is independently selected from the group consisting of hydrogen, C$_1$-C$_{12}$alkyl, C$_1$-C$_{12}$alkoxy, C$_2$-C$_{12}$alkenyl, C$_2$-C$_{12}$alkynyl, C$_3$-C$_{12}$cycloalkyl, C$_6$-C$_{14}$aryl, and C$_2$-C$_{11}$heterocyclyl, or wherein the two R$^b$ groups may form a heterocyclyl with the nitrogen, oxygen, or sulfur to which they are connected, wherein the C$_1$-C$_{12}$alkyl, C$_1$-C$_{12}$alkoxy, C$_2$-C$_{12}$alkenyl, C$_2$-C$_{12}$alkynyl, C$_3$-C$_{12}$cycloalkyl, C$_6$-C$_{14}$aryl, and C$_2$-C$_{11}$heterocyclyl are optionally substituted by one of more groups selected from halogen, hydroxy, amino, carboxy, C$_1$-C$_6$alkyl, C$_1$-C$_4$ carbonylamino, and C$_1$-C$_4$ alkoxy; and R$^c$ is independently selected from the group consisting of hydrogen, halogen, C$_1$-C$_{12}$alkyl, C$_1$-C$_{12}$alkenyl, C$_1$-C$_{12}$alkynyl, C$_3$-C$_{12}$cycloalkyl, C$_2$-C$_{11}$heterocyclyl, and C$_6$-C$_{14}$aryl; wherein the C$_1$-C$_{12}$alkyl, C$_1$-C$_{12}$alkenyl, C$_1$-C$_{12}$alkynyl, C$_3$-C$_{12}$cycloalkyl, C$_2$-C$_{11}$heterocyclyl, and C$_6$-C$_{14}$aryl are optionally substituted from the group consisting of hydrogen, halogen, hydroxy, amino, carboxy, C$_1$-C$_4$ carbonylamino, and C$_1$-C$_4$ alkoxy.

In some embodiments, the compound is of the following structural formula,

[Formula II]

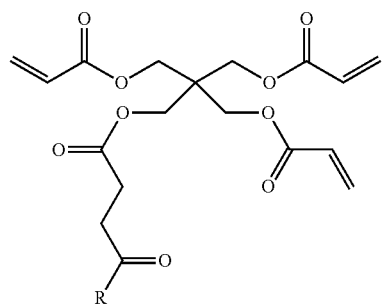

or a pharmaceutical salt thereof; wherein R is selected from the group consisting of hydrogen, bromo, iodo, fluoro, C$_1$-C$_{12}$alkyl, C$_2$-C$_{12}$alkenyl, C$_2$-C$_{12}$alkynyl, C$_3$-C$_{12}$cycloalkyl, C$_2$-C$_{11}$heterocyclyl, C$_6$-C$_{14}$aryl, —N(R$^d$)$_2$, —SR$^d$, and —OR$^e$; wherein the C$_1$-C$_{12}$alkyl, C$_2$-C$_{12}$alkenyl, C$_2$-C$_{12}$alkynyl, C$_3$-C$_{12}$cycloalkyl, C$_2$-C$_{11}$heterocyclyl, and C$_6$-C$_{14}$aryl groups are optionally substituted by one or more groups selected from the group consisting of halogen, hydroxy, cyano, amino, C$_1$-C$_{12}$alkyl, In some embodiments, $R^1$ is —OCON(R$^a$)$_2$; wherein R$^a$ is selected from the group consisting of hydrogen and C$_1$-C$_8$alkyl; wherein the C$_1$-C$_6$alkyl is optionally substituted by one or four groups selected from halogen, hydroxy, amino, carboxy, C$_1$-C$_6$alkyl, C$_1$-C$_4$ carbonylamino, and C$_1$-C$_4$ alkoxy.

In some embodiments, the compound is of the following structural formula, or a pharmaceutically acceptable salt thereof;

[Formula I]

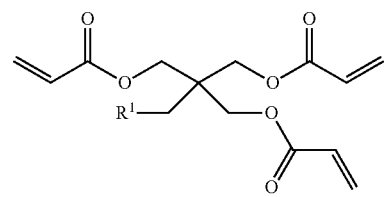

wherein $R^1 =$ 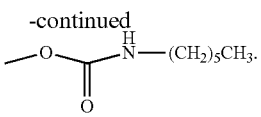

$C_1$-$C_{12}$alkenyl, $C_1$-$C_{12}$alkynyl, $C_1$-$C_{12}$alkoxy, $C_3$-$C_{12}$cycloalkyl, $C_2$-$C_{11}$heterocyclyl, $C_6$-$C_{14}$aryl, $C_1$-$C_{12}$alkylamino, and di($C_1$-$C_{12}$alkyl)amino; $R^d$ is independently selected from the group consisting of hydrogen, $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two $R^d$ groups may form a heterocyclyl with the nitrogen to which they are connected, wherein the $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, and $C_1$-$C_4$ alkoxy; and $R^e$ is independently selected from the group consisting of $C_2$-$C_{12}$alkyl, $C_2$-$C_{12}$alkenyl, $C_2$-$C_{12}$alkynyl, benzyl, and phenyl, wherein the $C_2$-$C_{12}$alkyl, $C_r$-$C_{12}$alkenyl, $C_2$-$C_{12}$alkynyl, benzyl, and phenyl are optionally substituted from the group consisting of halogen, hydroxy, and $C_1$-$C_4$ alkoxy.

In some embodiments, the compound is of the following structural formula, or a pharmaceutically acceptable salt thereof;

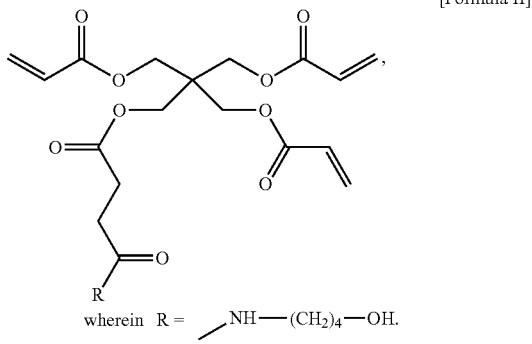

[Formula II]

wherein R = $\diagup$NH—(CH$_2$)$_4$—OH.

In some embodiments, modification of the triacrylate increases the ability of the triacrylate to promote adhesion and/or proliferation of dental pulp stem cells (DPSCs). In other embodiments, modification of the triacrylate increases the ability of the triacrylate to promote dental tissue repair and/or regeneration.

In some embodiments, the triacrylates comprises any compounds as described herein.

In some embodiments, the triacrylate is polymerized prior to contacting the dental tissue. In other embodiments, the triacrylate is polymerized after contacting the dental tissue. In some embodiments, the triacrylate is polymerized by UV irradiation.

In some embodiments, the triacrylate is polymerized prior to contacting the dental tissue. In other embodiments, the triacrylate is polymerized after contacting the dental tissue. In some embodiments, the triacrylate is polymerized by UV irradiation.

In some embodiments, the dental tissue is contacted by delivering the composition into a natural or artificial cavity or chamber of a tooth by injection. In other embodiments, the dental tissue is contacted by delivering the composition into a natural or artificial cavity or chamber of a tooth within a scaffold.

In some embodiments, the scaffold comprises a particle that encapsulates the composition. In other embodiments, the particle that encapsulates the composition is selected from the group consisting of a microsphere, a liposome, a microparticle, or combinations thereof. In some embodiments, the scaffold comprises a hydrogel. In some embodiments, the hydrogel is selected from the group consisting of collagen, alginate, polysaccharide, gelatin, chitosan, hyaluronic acid (HA), polyethylene glycol (PEG), poly (glycolide) (PGA), poly(L-lactide) (PLA), poly(lactide-co-glycolide) (PLGA), and polylactic-coglycolic acid.

In some embodiments, the dental tissue is contacted by delivering the composition into a natural or artificial cavity or chamber of a tooth as a monomer. In other embodiments, the monomer is polymerized after delivery into the natural or artificial cavity or chamber of the tooth by in situ polymerization. In some embodiments, the monomer is polymerized by UV irradiation.

In some embodiments, the composition further promotes migration and/or differentiation of DPSCs.

In some embodiments, the composition comprises a bioactive agent. In other embodiments, the bioactive agent is a compound selected from the group consisting of a chemotactic compound, an osteogenic compound, a dentinogenic compound, an amelogenic compound, an angiogenic compound, and combinations thereof. In certain embodiments, the bioactive agent is an antibiotic or an analgesic.

In some embodiments, the composition further comprises a cell. In other embodiments, the composition is free of a bioactive agent or a cell.

In some embodiments, the subject is a mammal. In other embodiments, the subject is a human.

In some embodiments, the methods further include assessing the expression level of a marker of DPSC differentiation. In some embodiments, the marker of DPSC differentiation is selected from the group consisting of BGLAP, DSPP, RUNX2, TGEB1, DMP1, ALP and SPP1.

In certain embodiments, the expression level of a marker of DPSC differentiation is assessed by a method selected from the group consisting of immunofluorescence, quantitative PCR, and Western blot analysis.

In one aspect, the present invention provides methods of treating a periodontal disease in a subject in need thereof. The methods include contacting a dental pulp tissue with a composition comprising a triacrylate capable of promoting adhesion and/or proliferation of dental pulp stem cells (DPSCs); and regenerating dental pulp tissue by allowing DPSCs to adhere to the composition and proliferate, thereby treating the periodontal disease in the subject.

In another aspect, the present invention provides methods of treating a dental pulp infection in a subject in need thereof. The methods include contacting a dental pulp tissue with a composition comprising a triacrylate capable of promoting adhesion and/or proliferation of dental pulp stem cells (DPSCs); and regenerating dental pulp tissue by allowing DPSCs to adhere to the composition and proliferate, thereby treating dental pulp infection in the subject.

In some embodiments, the triacrylate is selected from the group consisting of trimethylolpropane propoxylate triacrylate, trimethylolpropane triacrylate, pentaerythritol triacrylate, trimethylolpropane ethoxylate triacrylate, succinic acid triacrylate and combinations thereof.

In some embodiments, the triacrylate is trimethylolpropane propoxylate triacrylate. In other embodiments, the triacrylate is trimethylolpropane triacrylate. In some embodiments, the triacrylate is pentaerythritol triacrylate. In other embodiments, the triacrylate is trimethylolpropane ethoxylate triacrylate. In yet another embodiment, the triacrylate is succinic acid triacrylate.

In some embodiments, the triacrylate is modified triacrylate.

In some embodiments, the triacrylate is a compound of Formula I, comprising the structure:

[Formula I]

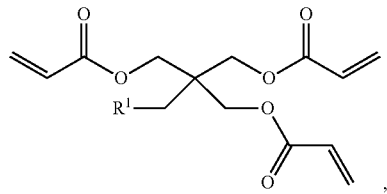

or a pharmaceutically acceptable salt thereof.

In some embodiments, $R^1$ is selected from the group consisting of —COOR$^a$, —OCOR$^a$, —NR$^a$COOR$^a$, —OCON(R$^a$)$_2$, —NR$^b$COR$^a$, —CON(R$^a$)$_2$, —COR$^a$ and —NHCON(R$^a$)$_2$; R$^a$ is selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_2$-$C_{11}$heterocyclyl, $C_6$-$C_{14}$aryl, —N(R$^b$)$_2$, —SR$^b$, and —OR$^b$; wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_2$-$C_{11}$heterocyclyl, and $C_6$-$C_{14}$aryl groups are optionally substituted with one or four groups selected from the group consisting of hydrogen, halogen, hydroxy, cyano, amino, $C_1$-$C_{12}$alkyl, $C_1$-$C_{12}$alkoxy, $C_1$-$C_{12}$alkenyl, $C_1$-$C_{12}$alkynyl, $C_3$-$C_{12}$cycloalkyl, $C_2$-$C_{11}$heterocyclyl, $C_6$-$C_{14}$aryl, $C_1$-$C_{12}$alkylamino, di($C_1$-$C_{12}$alkyl)amino, —COOR$^c$, —OCOR$^c$, —NR$^c$COOR$^c$, —OCON(R$^c$)$_2$, —NR$^c$COR$^c$, —CON(R$^c$)$_2$, —COR$^c$ and —NHCON(R$^a$)$_2$; R$^b$ is independently selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two R$^b$ groups may form a heterocyclyl with the nitrogen, oxygen, or sulfur to which they are connected, wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, amino, carboxy, $C_1$-$C_6$alkyl, $C_1$-$C_4$ carbonylamino, and $C_1$-$C_4$ alkoxy; and R$^c$ is independently selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two R$^c$ groups may form a heterocyclyl with the nitrogen or sulfur to which they are connected, wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, amino, carboxy, $C_1$-$C_6$alkyl, $C_1$-$C_4$ carbonylamino, and $C_1$-$C_4$ alkoxy.

In some embodiments, $R^1$ is —OCON(R$^a$)$_2$; wherein R$^a$ is selected from the group consisting of hydrogen and $C_1$-$C_8$alkyl; wherein the $C_1$-$C_6$alkyl is optionally substituted by one or four groups selected from halogen, hydroxy, amino, carboxy, $C_1$-$C_6$alkyl, $C_1$-$C_4$ carbonylamino, and $C_1$-$C_4$ alkoxy.

In some embodiments, the compound is of the following structural formula, or a pharmaceutically acceptable salt thereof;

[Formula I]

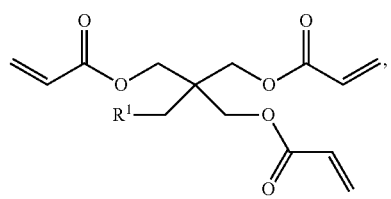

-continued

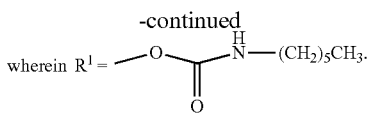

wherein $R^1 =$

In some embodiments, $R^1$ is —OCOR$^a$; wherein R$^a$ is selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_2$-$C_{11}$heterocyclyl, $C_6$-$C_{14}$aryl, —N(R$^b$)$_2$, —SR$^b$, and —OR$^b$; wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_2$-$C_{11}$heterocyclyl, and $C_6$-$C_{14}$aryl groups are optionally substituted with one or four groups selected from the group consisting of hydrogen, halogen, hydroxy, cyano, amino, $C_1$-$C_{12}$alkyl, $C_1$-$C_{12}$alkoxy, $C_1$-$C_{12}$alkenyl, $C_1$-$C_{12}$alkynyl, $C_3$-$C_{12}$cycloalkyl, $C_2$-$C_{11}$heterocyclyl, $C_6$-$C_{14}$aryl, $C_1$-$C_{12}$alkylamino, di($C_1$-$C_{12}$alkyl)amino, —COOR$^c$, —OCOR$^c$, —NR$^c$COOR$^c$, —OCON(R$^c$)$_2$, —NR$^c$COR$^c$, —CON(R$^c$)$_2$, —COR$^c$ and —NHCON(R$^c$)$_2$; wherein R$^b$ is independently selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two R$^b$ groups may form a heterocyclyl with the nitrogen, oxygen, or sulfur to which they are connected, wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, amino, carboxy, $C_1$-$C_6$alkyl, $C_1$-$C_4$ carbonylamino, and $C_1$-$C_4$ alkoxy; and R$^c$ is independently selected from the group consisting of hydrogen, halogen, $C_1$-$C_{12}$alkyl, $C_1$-$C_{12}$alkenyl, $C_1$-$C_{12}$alkynyl, $C_3$-$C_{12}$cycloalkyl, $C_2$-$C_{11}$heterocyclyl, and $C_6$-$C_{14}$aryl; wherein the $C_1$-$C_{12}$alkyl, $C_1$-$C_{12}$alkenyl, $C_1$-$C_{12}$alkynyl, $C_3$-$C_{12}$cycloalkyl, $C_2$-$C_{11}$heterocyclyl, and $C_6$-$C_{14}$aryl are optionally substituted from the group consisting of hydrogen, halogen, hydroxy, amino, carboxy, $C_1$-$C_4$ carbonylamino, and $C_1$-$C_4$ alkoxy.

In some embodiments, the compound is of the following structural formula,

[Formula II]

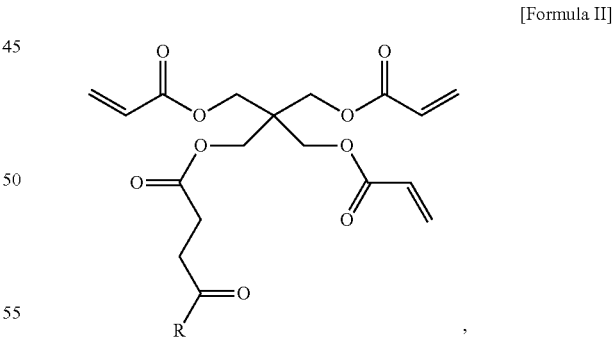

or a pharmaceutical salt thereof; wherein R is selected from the group consisting of hydrogen, bromo, iodo, fluoro, $C_1$-$C_{12}$alkyl, $C_2$-$C_{12}$alkenyl, $C_2$-$C_{12}$alkynyl, $C_3$-$C_{12}$cycloalkyl, $C_2$-$C_{11}$heterocyclyl, $C_6$-$C_{14}$aryl, —N(R$^d$)$_2$, —SR$^d$, and —OR$^e$; wherein the $C_1$-$C_{12}$alkyl, $C_2$-$C_{12}$alkenyl, $C_2$-$C_{12}$alkynyl, $C_3$-$C_{12}$cycloalkyl, $C_2$-$C_{11}$heterocyclyl, and $C_6$-$C_{14}$aryl groups are optionally substituted by one or more groups selected from the group consisting of halogen, hydroxy, cyano, amino, $C_1$-$C_{12}$alkyl, $C_1$-$C_{12}$alkenyl, $C_1$-$C_{12}$alkynyl, $C_1$-$C_{12}$alkoxy, $C_3$-$C_{12}$cycloalkyl, $C_2$-$C_{11}$heterocyclyl, $C_6$-$C_{14}$aryl, $C_1$-$C_{12}$alkylamino, and di($C_1$-$C_{12}$alkyl)amino; $R^d$ is independently selected from the group consisting of hydrogen, $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two $R^d$ groups may form a heterocyclyl with the nitrogen to which they are connected, wherein the $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, and $C_1$-$C_4$ alkoxy; and $R^e$ is independently selected from the group consisting of $C_2$-$C_{12}$alkyl, $C_2$-$C_{12}$alkenyl, $C_2$-$C_{12}$alkynyl, benzyl, and phenyl, wherein the $C_2$-$C_{12}$alkyl, $C_2$-$C_{12}$alkenyl, $C_2$-$C_{12}$alkynyl, benzyl, and phenyl are optionally substituted from the group consisting of halogen, hydroxy, and $C_1$-$C_4$ alkoxy.

In some embodiments, the compound is of the following structural formula, or a pharmaceutically acceptable salt thereof;

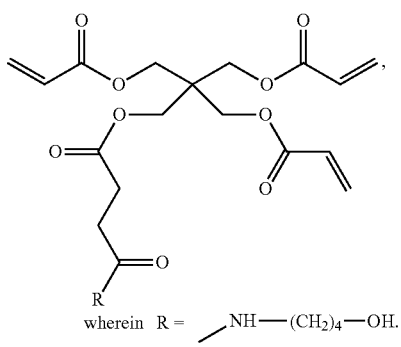

[Formula II]

wherein R = $\diagup$ NH—(CH$_2$)$_4$—OH.

In some embodiments, modification of the triacrylate increases the ability of the triacrylate to promote adhesion and/or proliferation of dental pulp stem cells (DPSCs). In other embodiments, modification of the triacrylate increases the ability of the triacrylate to promote dental tissue repair and/or regeneration.

In some embodiments, the triacrylates comprises any compounds as described herein.

In some embodiments, the triacrylate is polymerized prior to contacting the dental tissue. In other embodiments, the triacrylate is polymerized after contacting the dental tissue. In some embodiments, the triacrylate is polymerized by UV irradiation.

In some embodiments, the triacrylate is polymerized prior to contacting the dental tissue. In other embodiments, the triacrylate is polymerized after contacting the dental tissue. In some embodiments, the triacrylate is polymerized by UV irradiation.

In some embodiments, the dental tissue is contacted by delivering the composition into a natural or artificial cavity or chamber of a tooth by injection. In other embodiments, the dental tissue is contacted by delivering the composition into a natural or artificial cavity or chamber of a tooth within a scaffold.

In some embodiments, the scaffold comprises a particle that encapsulates the composition. In other embodiments, the particle that encapsulates the composition is selected from the group consisting of a microsphere, a liposome, a microparticle, or combinations thereof. In some embodiments, the scaffold comprises a hydrogel. In some embodiments, the hydrogel is selected from the group consisting of collagen, alginate, polysaccharide, gelatin, chitosan, hyaluronic acid (HA), polyethylene glycol (PEG), poly (glycolide) (PGA), poly(L-lactide) (PLA), poly(lactide-co-glycolide) (PLGA), and polylactic-coglycolic acid.

In some embodiments, the dental tissue is contacted by delivering the composition into a natural or artificial cavity or chamber of a tooth as a monomer. In other embodiments, the monomer is polymerized after delivery into the natural or artificial cavity or chamber of the tooth by in situ polymerization. In some embodiments, the monomer is polymerized by UV irradiation.

In some embodiments, the composition further promotes migration and/or differentiation of DPSCs.

In some embodiments, the composition comprises a bioactive agent. In other embodiments, the bioactive agent is a compound selected from the group consisting of a chemotactic compound, an osteogenic compound, a dentinogenic compound, an amelogenic compound, an angiogenic compound, and combinations thereof. In certain embodiments, the bioactive agent is an antibiotic or an analgesic.

In some embodiments, the composition further comprises a cell. In other embodiments, the composition is free of a bioactive agent or a cell.

In some embodiments, the subject is a mammal. In other embodiments, the subject is a human.

In yet another aspect, the present invention provides kits comprising a composition comprising a triacrylate capable of promoting adhesion and/or proliferation of dental pulp stem cells (DPSCs); and instructions for delivery of the composition into a dental tissue of a subject to treat a dental condition in the subject.

In some embodiments, the dental tissue is a dental pulp tissue. In other embodiments, the dental tissue is a dentin tissue.

In some embodiments, the kits comprise any compounds as described herein.

In yet another aspect, provided herein are dental repair (e.g., restoration) materials comprising a composition described herein.

The present invention is illustrated by the following drawings and detailed description, which do not limit the scope of the invention described in the claims.

BRIEF DESCRIPTION THE DRAWINGS

Figure 1:
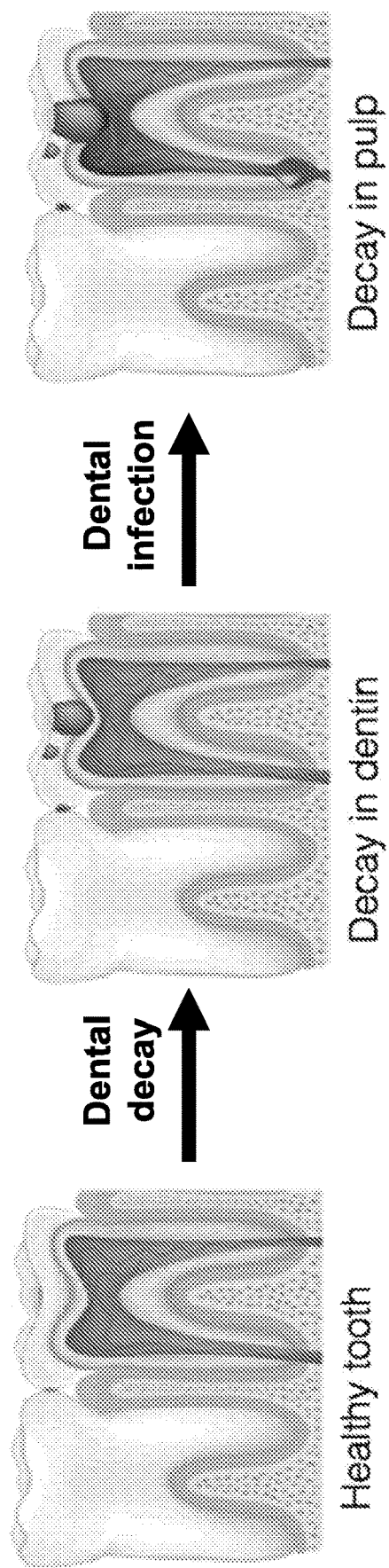
FIG. 1 depicts the general anatomy for a health tooth, an infected tooth with decay in dentin, and an infected tooth with decay in the pulp.
Figure 2:
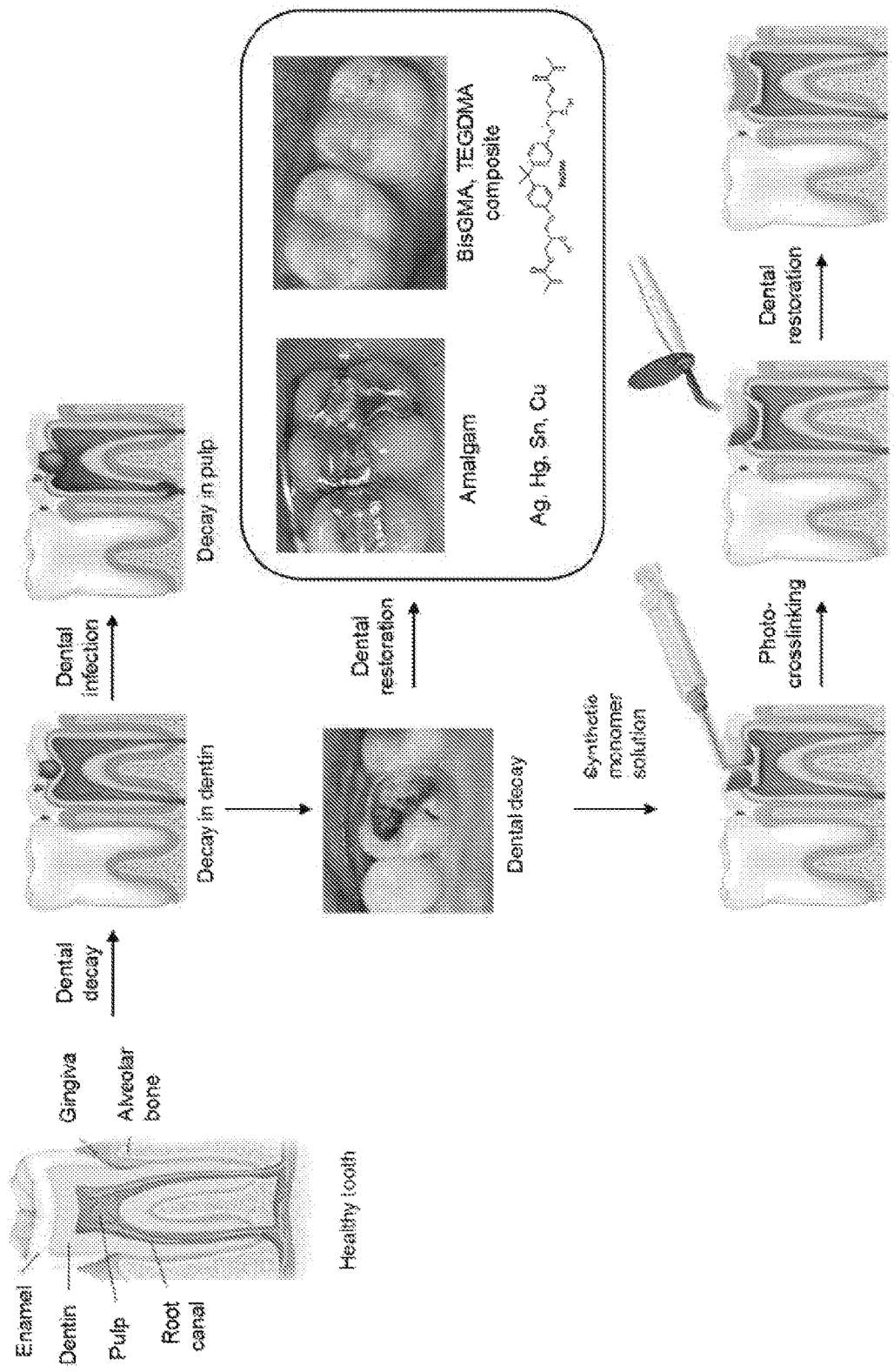
FIG. 2 is a schematic depiction of certain embodiments of the invention.
Figure 3A:
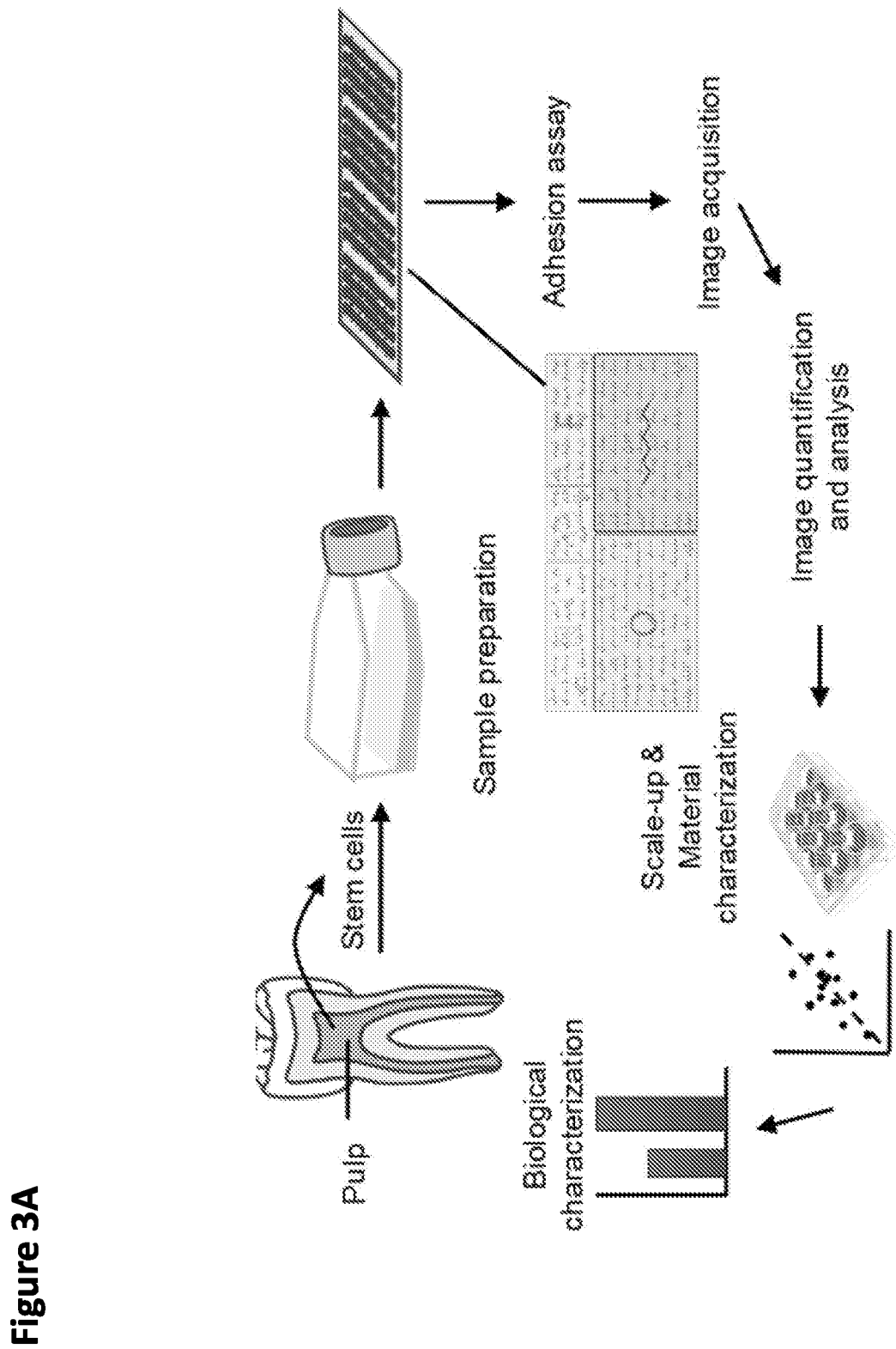
Figure 3B:
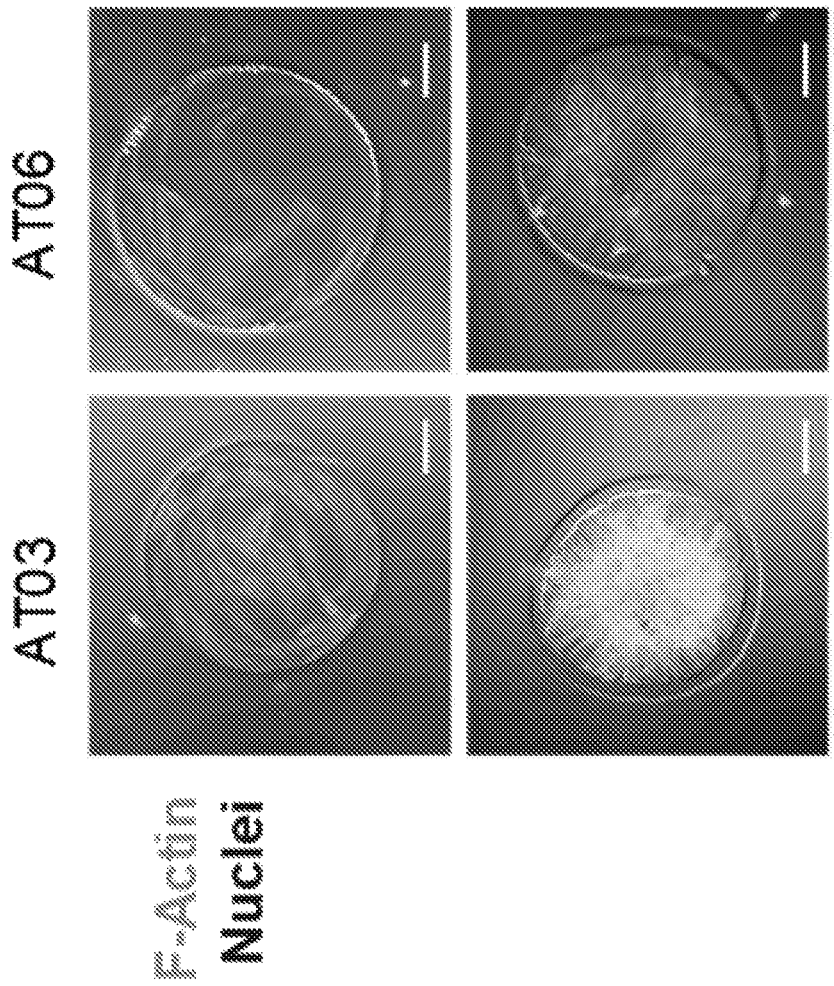

FIG. 3A depicts an overview for the high-throughput polymer miscroarray screen to identify novel therapeutic UV-curable biomaterials as substrates that adhere to human dental pulp stem cells (DPSC). DPSCs were procured from human donor teeth and expanded in tissue culture to be used in the experimental workflow, which involved screening, scaling up the materials to cell culture substrates, materials characterization, and biological characterization. Specifically, monomers were printed and photo-polymerized on polyHEMA coated slides in microarrays. Human dental pulp stem cells (DPSCs) were seeded at high seeding density (80,000 cells per array) and low seeding density (8,000 cells per array) on two arrays in serum-free media conditions (alpha MEM with 0.1 mM ascorbic acid and 1% penicillin/ streptomycin at 37° C. under 5% $CO_2$). Cells were fixed with 4% PFA, and stained with DAPI and phalloidin-488. (FIG. 3B, scale bar=100 µm). Automated-stage fluorescent imaging was performed with manual cell counting and image processing to quantify adhered cell number and cell area per polymer spot. The quantification of a combined area x count index yielded top-performing polymers identified as AT03 (trimethylolpropane triacrylate), and AT06 (pentaerythritol triacrylate) (FIG. 3C, black bars, statistically significantly different from overall mean, p<0.05, Kruskal-Wallis test with Dunn's multiple comparisons test, n=5 per marker).

Figure 4:
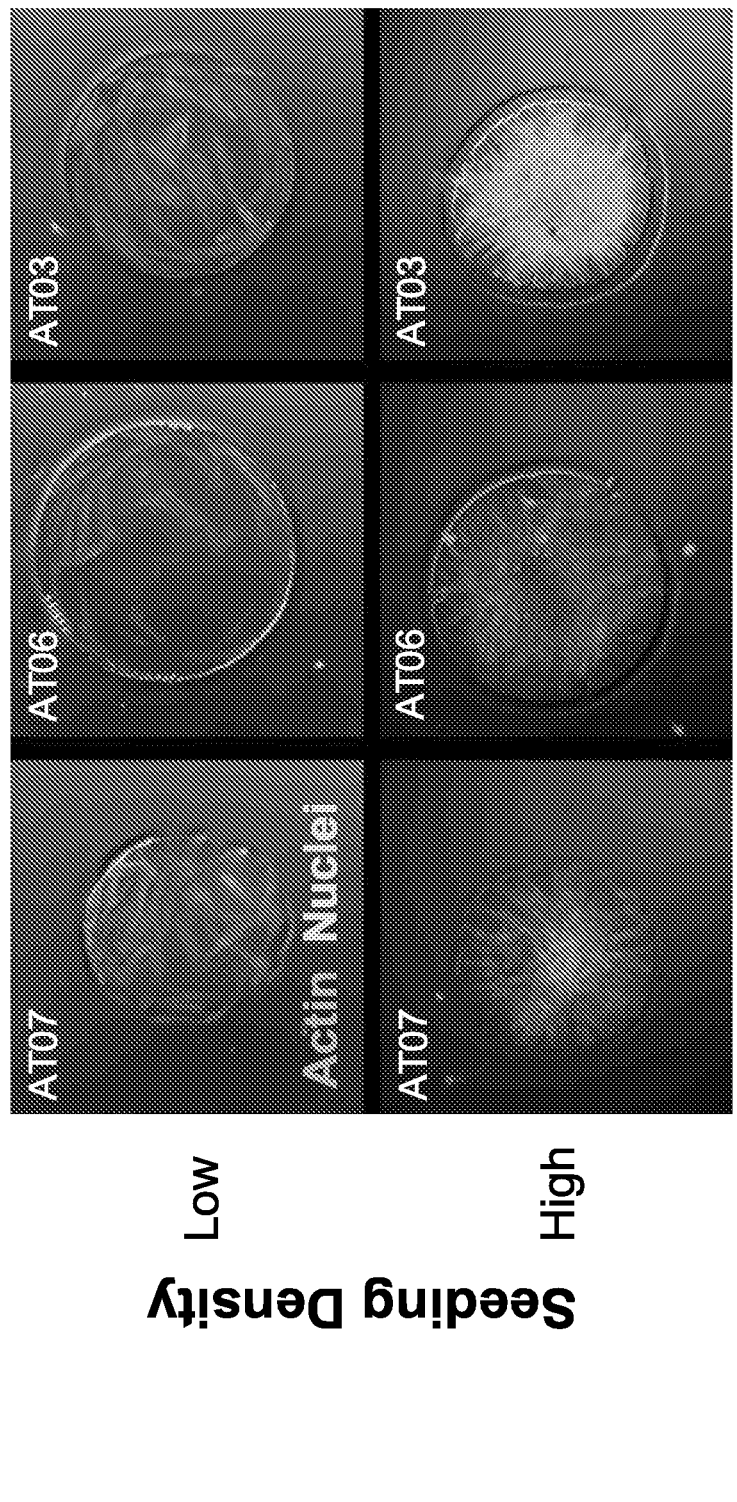

FIG. 4 depicts fluorescent images for DPSC adhesion to polymer microarrays. Specifically, fluorescent images of DPSCs on selected polymers AT03 (trimethylolpropane triacrylate), AT06 (pentaerythritol triacrylate) and AT07 (trimethylolpropane ethoxylate triacrylate) were illustrated at both high and low seeding density conditions in serum-free media. Actin is stained green with phalloidin-488 and cell nuclei are stained blue with DAPI.

Figure 5:
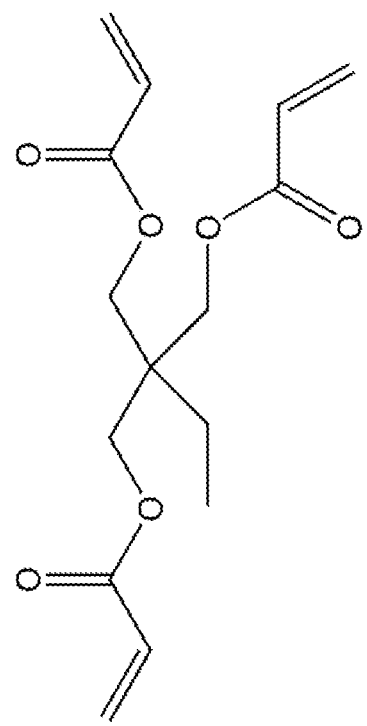

FIG. 5 depicts the chemical structure of AT03 (trimethylolpropane triacrylate).

Figure 6:
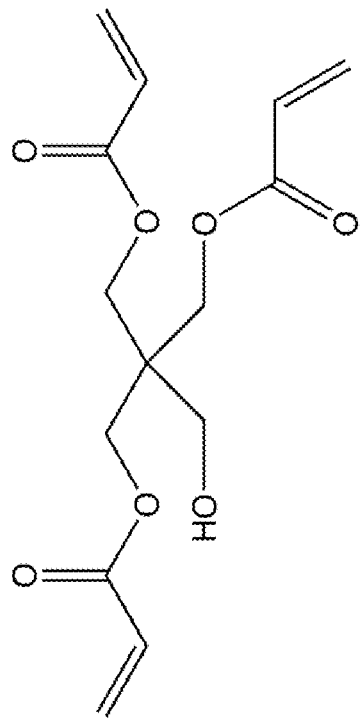

FIG. 6 depicts the chemical structure of AT06 (pentaerythritol triacrylate).

Figure 7:
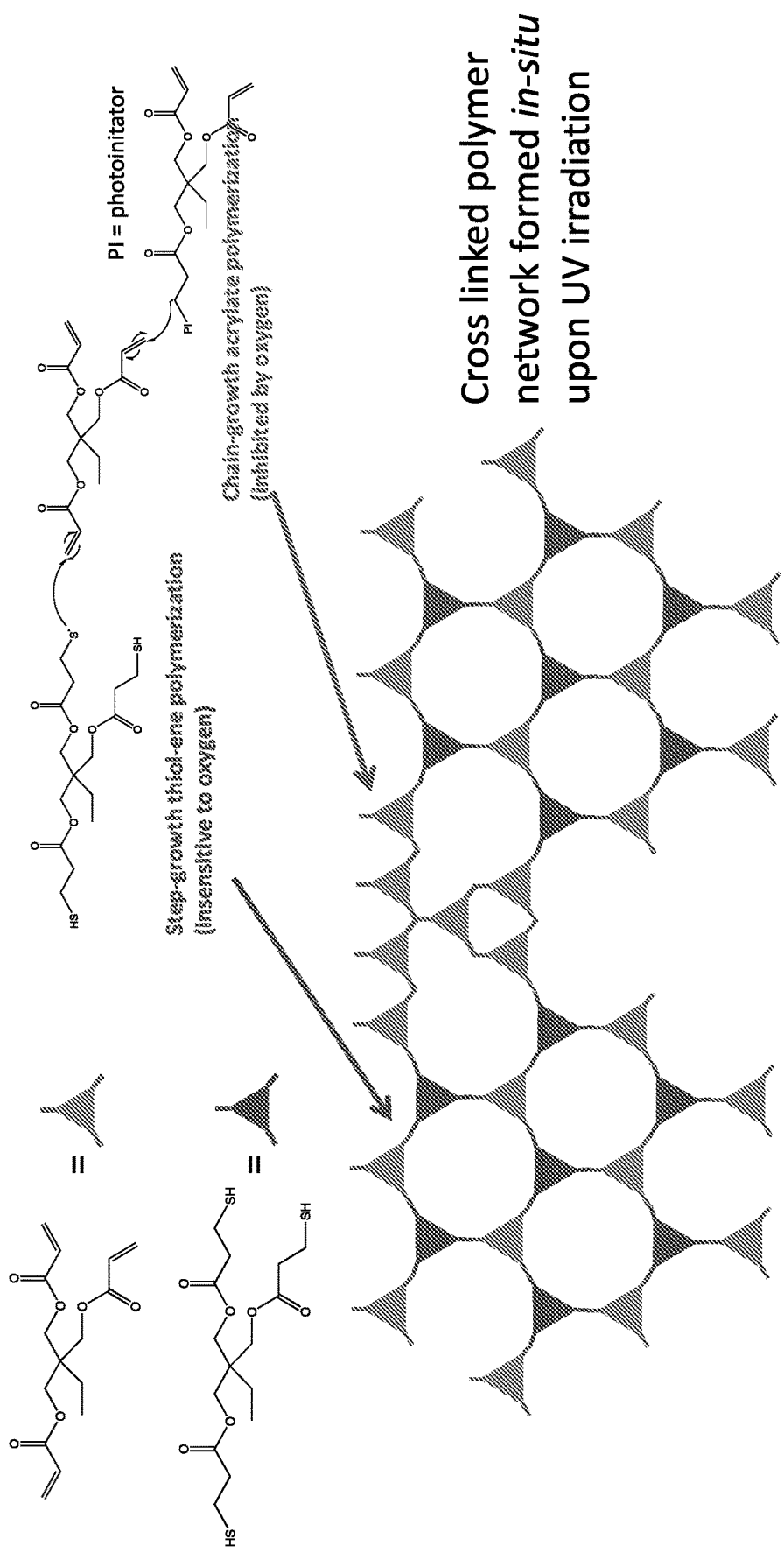

FIG. 7 depicts the chemical composition and mechanism of in situ polymerization of monomer hits with thiol-ene crosslinking.

Figure 8A:
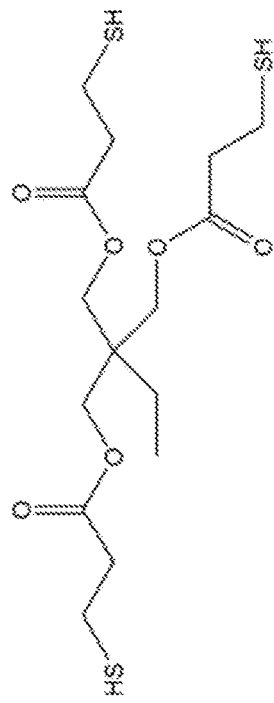
Figure 8B:
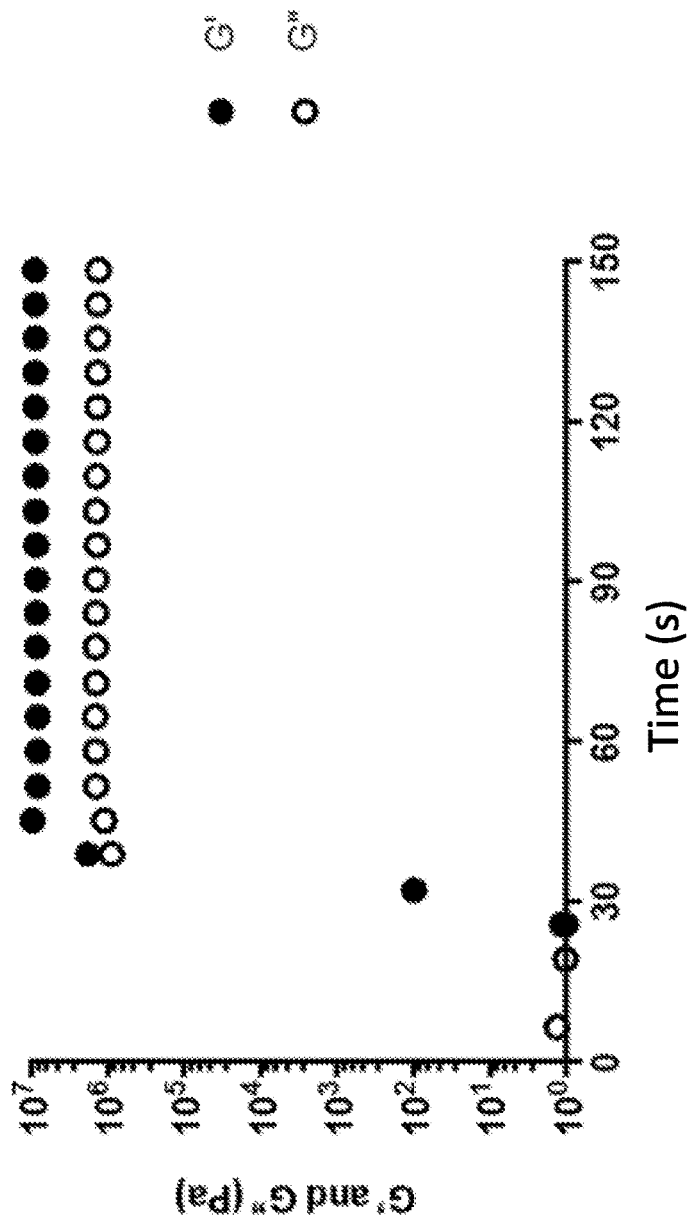
Figure 8C:
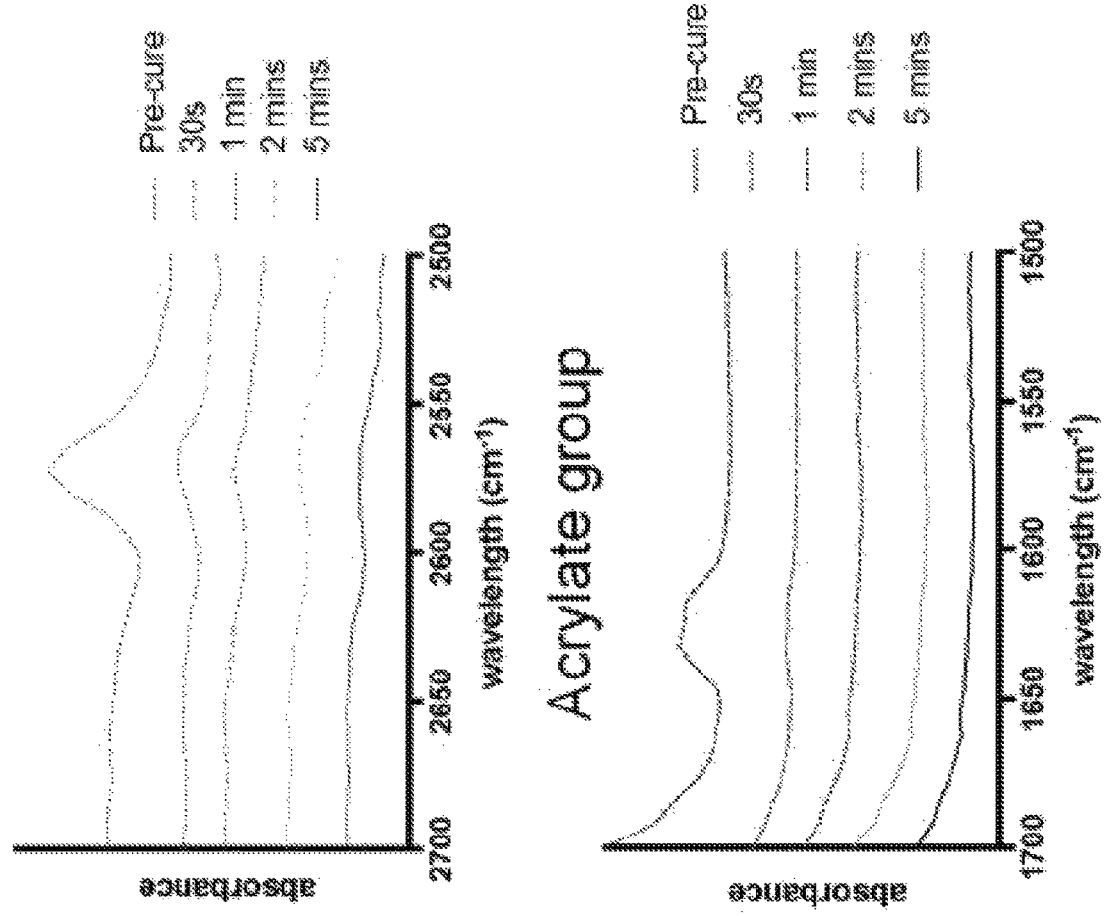

FIG. 8A depicts the chemical structure of an AT03 monomer by adding a tri-thiol and photoinitiator using thiol-ene chemistry. FIG. 8B depicts the rheological measurements of the storage and loss moduli of AT03. The thiol and the triacrylates polymerize by both chain growth and network polymerization to yield fast curing in about 30 seconds. FIG. 8C depicts a significant attenuation of the acrylate and thiol peaks after curing by fourier-transform infrared spectroscopy.

Figure 9A:
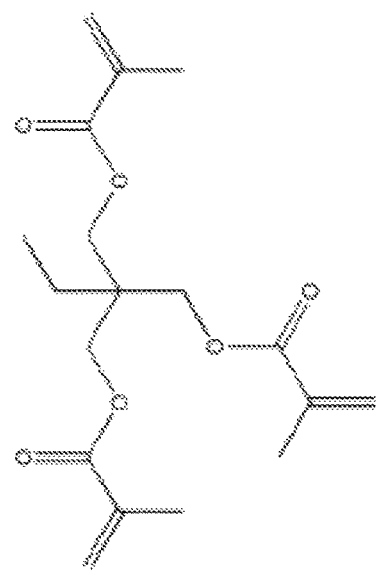
Figure 9B:
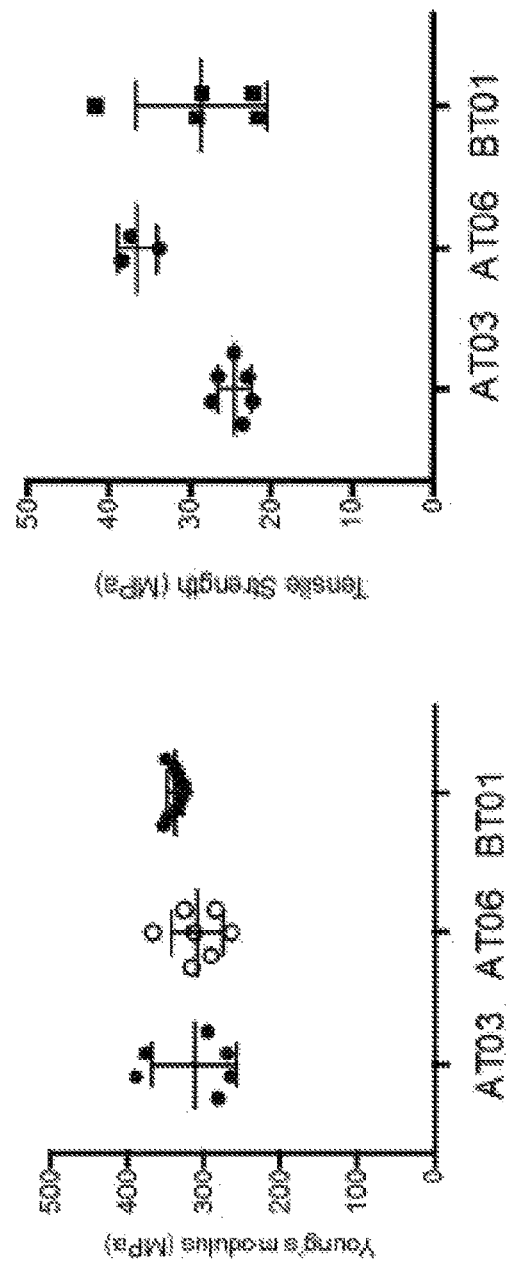

FIG. 9A depicts the chemical structure of BT01 (trimethylolpropane trimethacrylate). FIG. 9B depicts the mechanical properties of AT03, AT07 and BT01 polymers.

Figure 10A:
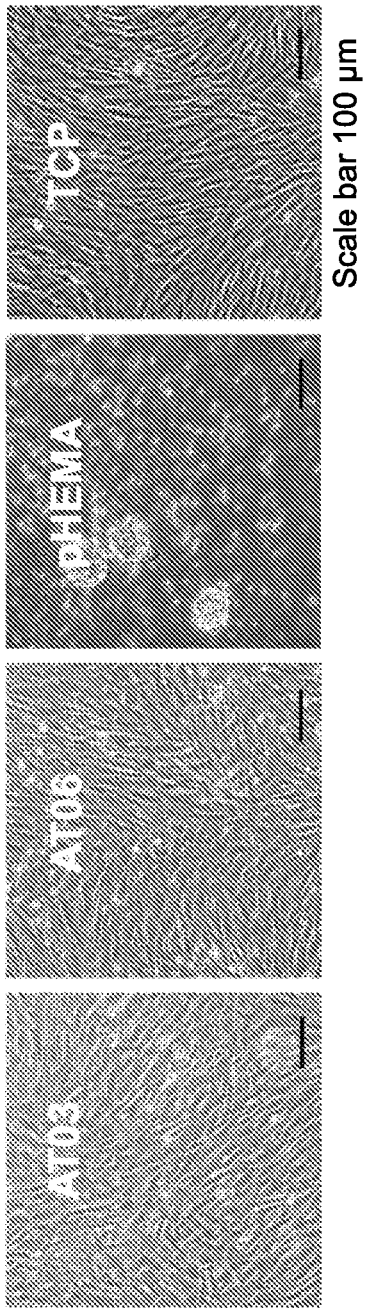
Figure 10C:
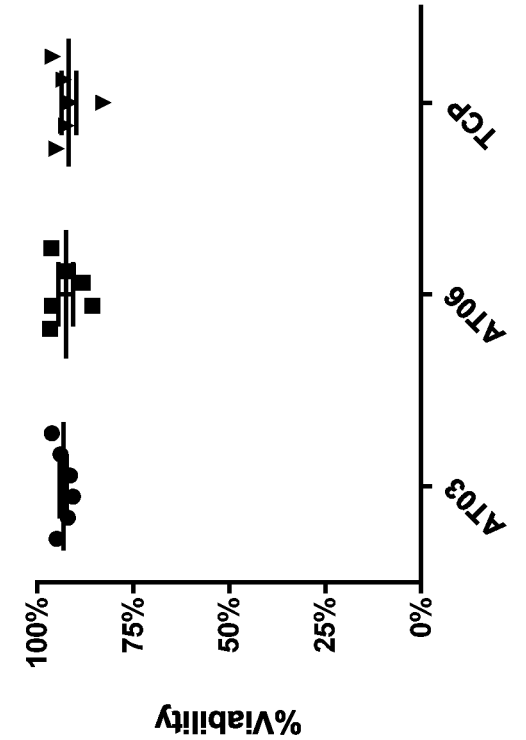
Figure 10B:
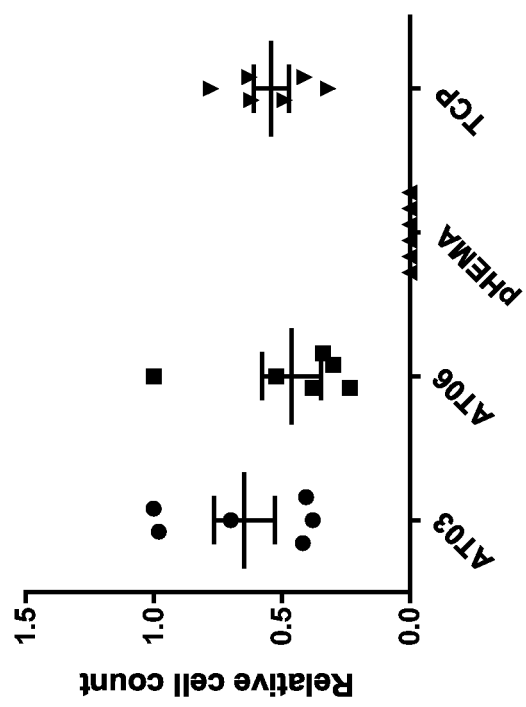

FIGS. 10A-C depict adhesion of DPSCs to scaled-up polymers. Specifically, FIG. 10A depicts adhesion of cells after a 48 hour incubation by phase contrast microscopy. FIG. 10B depicts the relative cell count between AT03, AT06, pHEMA (negative control) and TCP (positive control). DPSCs adhered in serum-free conditions in high confluence on the triacrylates AT03 and AT06, similar to the tissue culture plastic control. No cells adhered to the negative control polyHEMA (scale bar 100 um). FIG. 10C depicts the percent viability between AT03, AT06, pHEMA and TCP. Data were compared using one-way ANOVA with multiple comparisons test ($\alpha$=0.05).

Figure 11A:
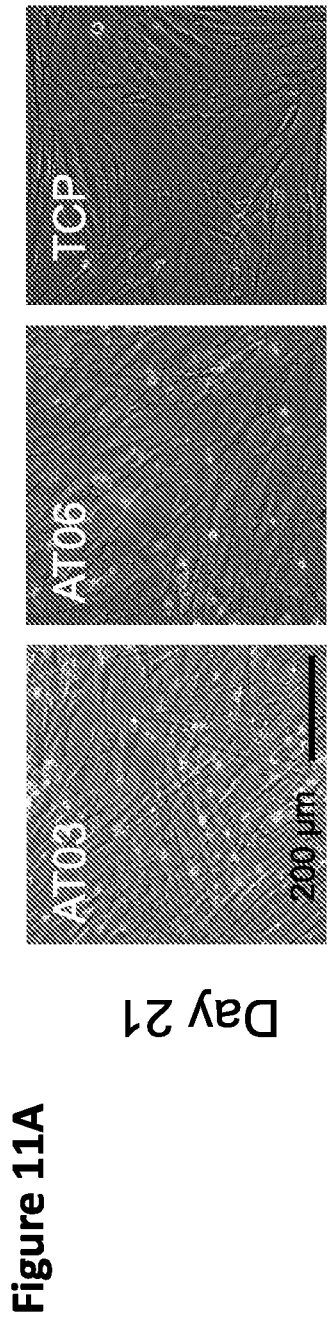
Figure 11B:
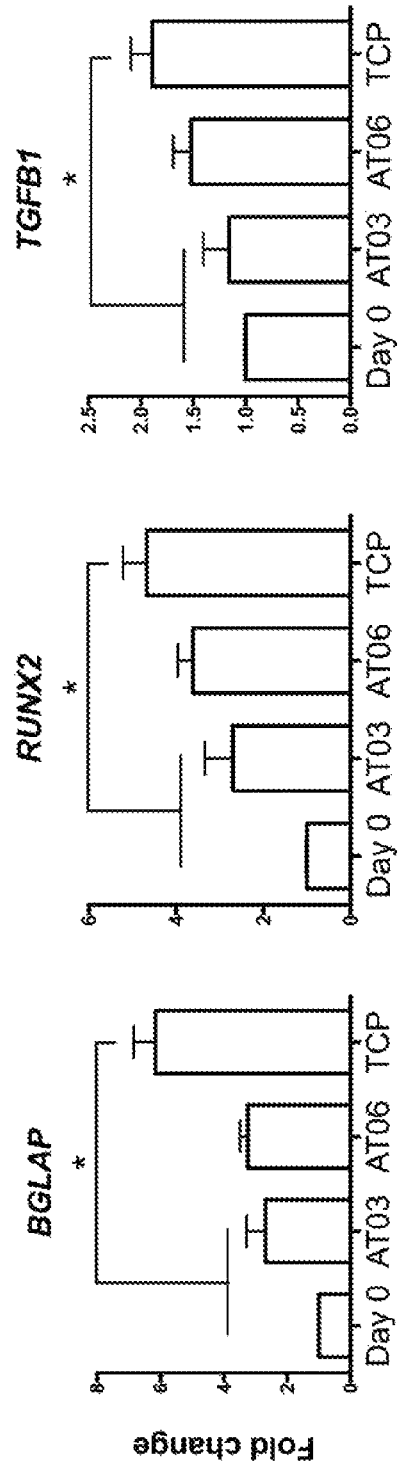

FIGS. 11A and 11B depict long-term culture of DPSCs on AT03 and AT06. Specifically, DPSCs were seeded onto 12-well plates coated with polymers or tissue culture plastic control in serum-free conditions. Media was changed every 3-7 days. Cells were lysed for collecting RNA for quantitative PCR analysis. cDNA was reverse transcribed for RT-qPCR (BioRad). Quantitative PCR was performed in duplicate with 10 ng of cDNA in each reaction, and each qPCR measurement was repeated on at least three replicate samples. Relative gene expression was computed by the delta-delta Ct method, which compared Ct values to a control sample (Day 0) and reference gene (GAPDH). ANOVA and post-hoc statistical tests were performed on the log 2 transform of delta-Ct values to meet the assumption that the data follow a normal distribution. FIG. 11A depicts phase contrast microscopic images of cells at Day 21 in serum-free media. FIG. 11B depicts the relative gene expression level of DPSC differentiation markers: BGLAP (left), RUNX2 (middle) and TGFB1 (right) in DPSCs on AT03, AT06 and TCP (positive control) in serum-free media. Data were normalized to a control sample at Day 0. Data were compared using two-way ANOVA with multiple comparisons test (N$\geq$4, p<0.05). Values represent the mean and the standard error of the mean (SEM).

Figure 12A:
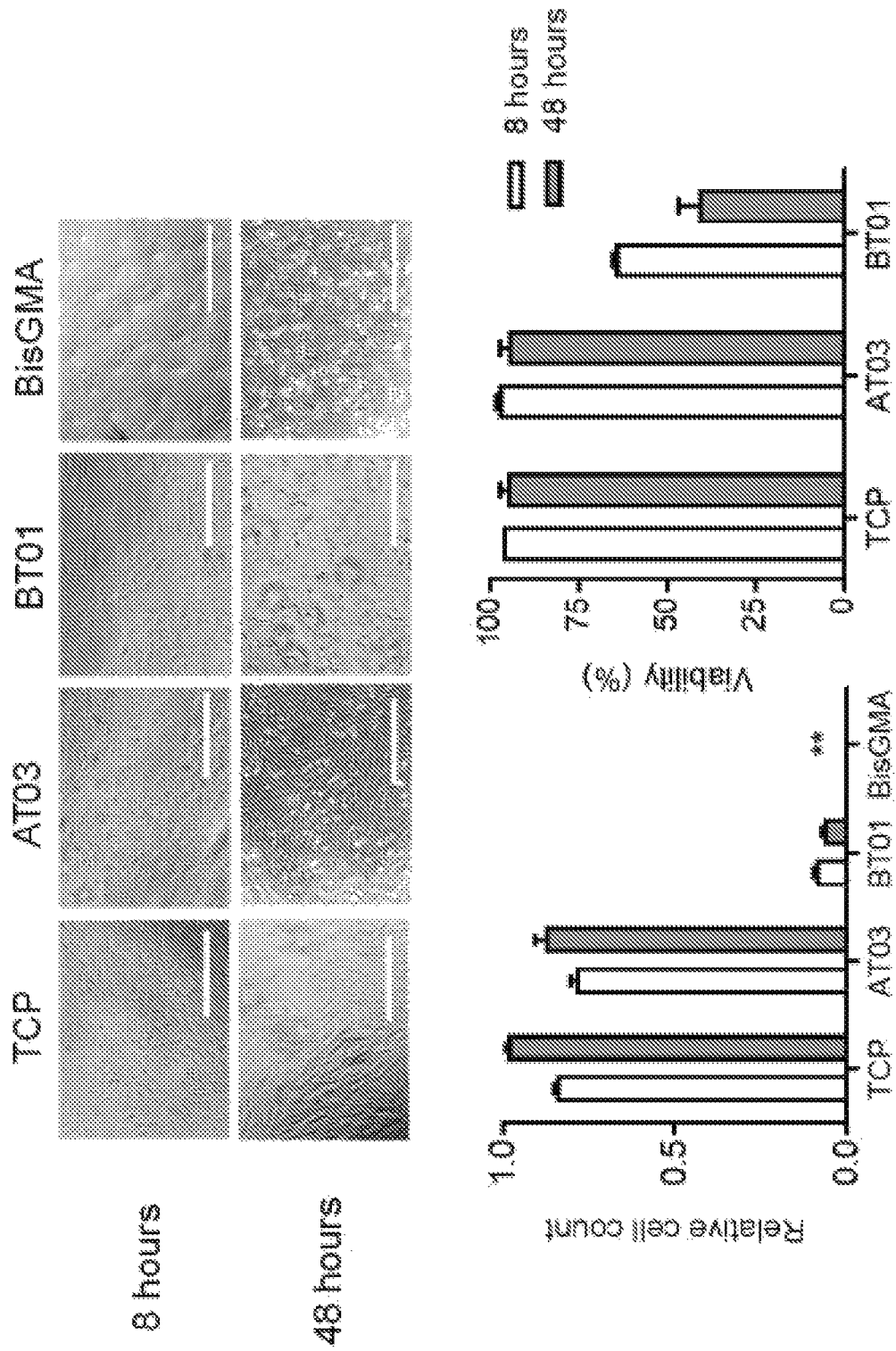
Figure 12B:
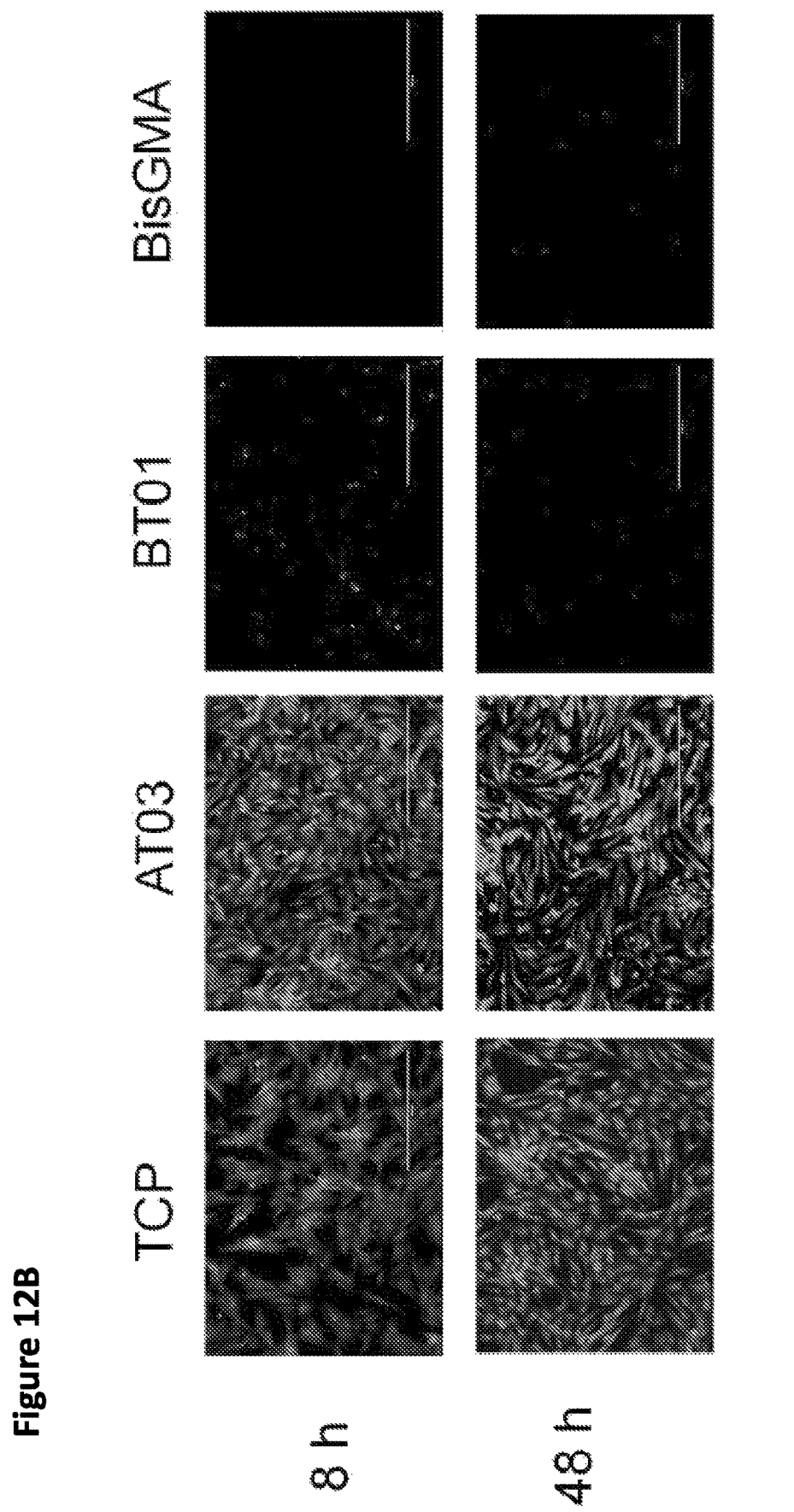
Figure 12C:
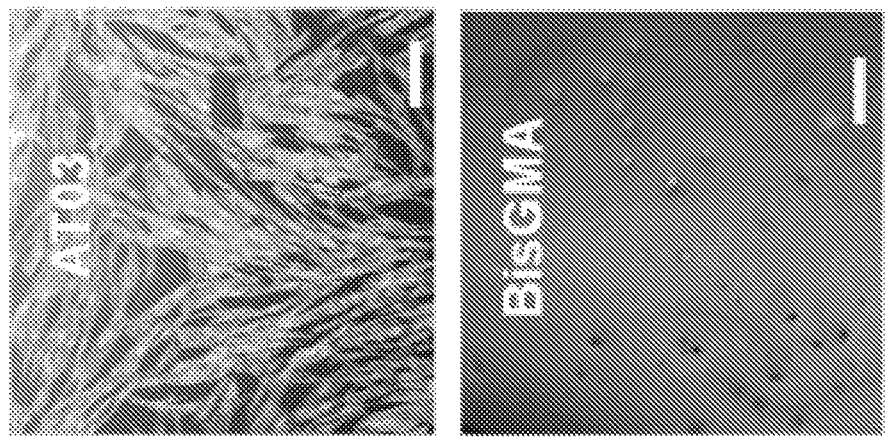
Figure 12D:
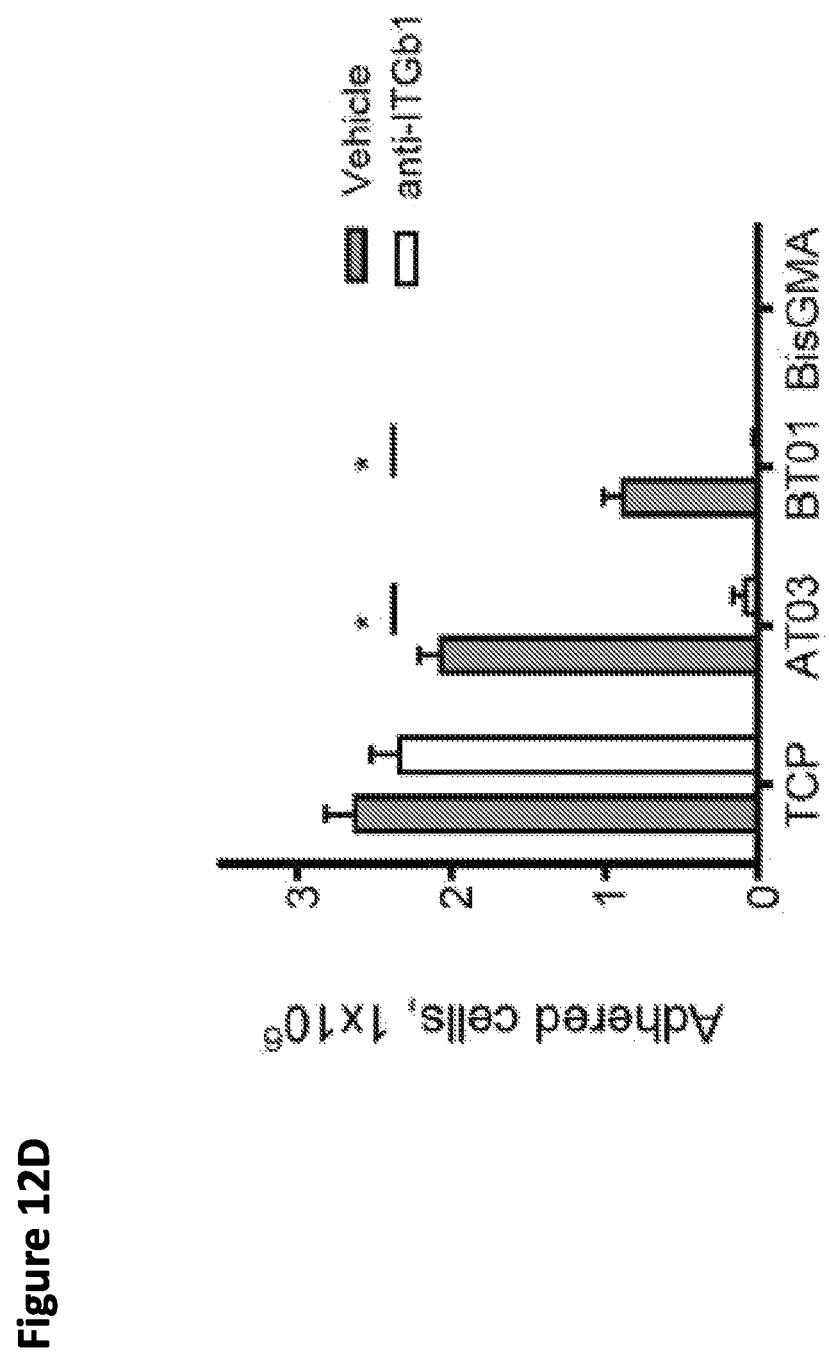
Figure 12E:
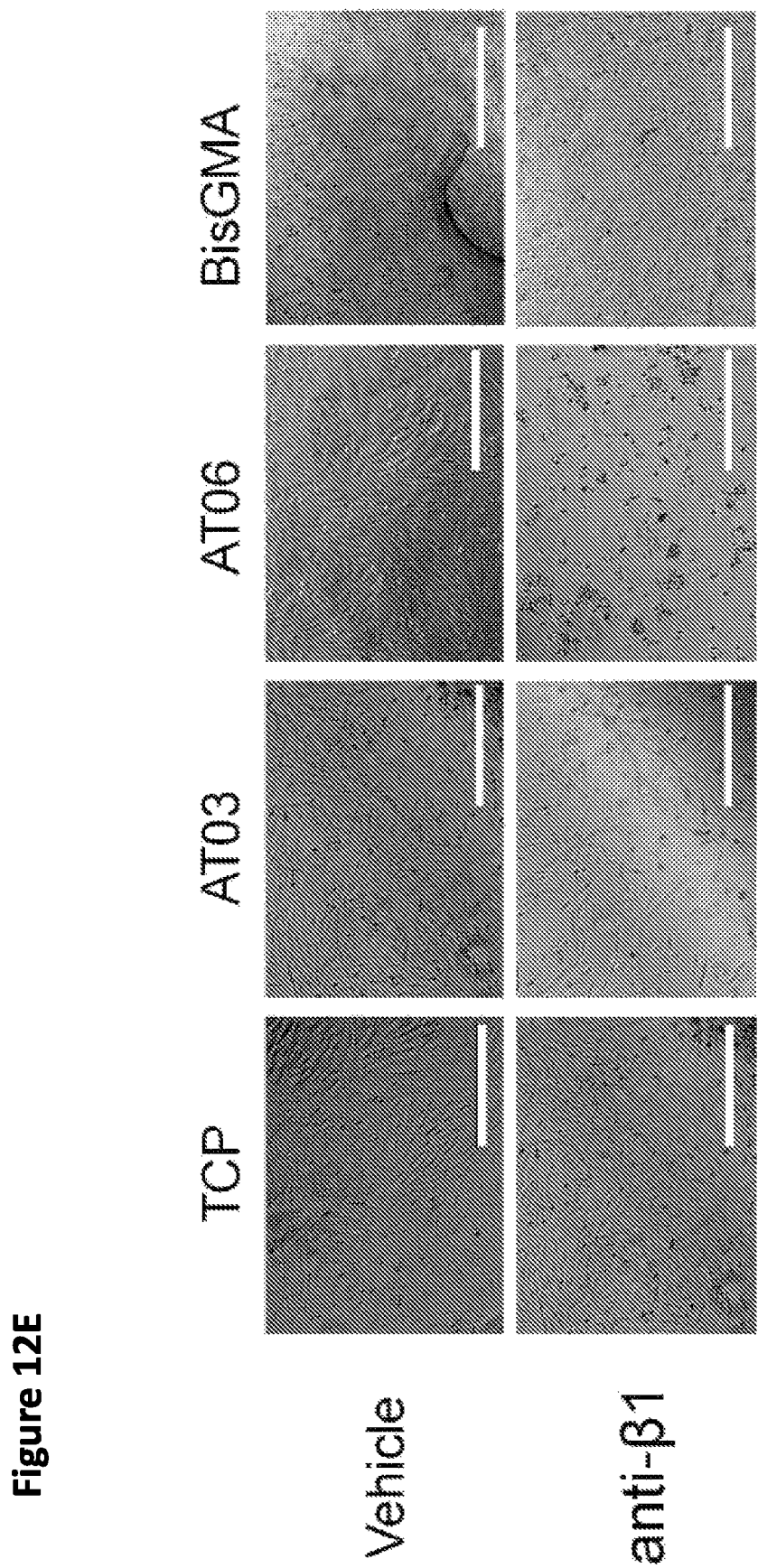

FIGS. 12A-E depict images and graphs demonstrating that DPSCs adhere to triacrylate polymers and proliferate in a ($\beta$3-dependent manner. FIG. 12A depicts DPSC cell count and phase images over 48 hours showing that DPSCs proliferate on the tissue culture plastic and triacrylate AT03, but not on trimethacrylate BT01 or control BisGMA, which is a methacrylate used in commercially available dental materials (scale bar 400 um). The cell counts on BisGMA were below the level of detection. FIG. 12B are images depicting live-dead staining at 8 and 48 hours showing that cells adhered to AT03 are viable similar to TCP, but viable cells are significantly less on BT01 and BisGMA. FIG. 12C are images depicting that DPSCs on AT03 were positive for proliferation marker, Ki67, by both immunostaining and confocal microscopy (F-actin green, Ki67 red). FIGS. 12D and 12E are images and graphs demonstrating that integrin ($\beta$1 receptor was required for the DPSCs to adhere to extracellular matrix that the cells expressed onto the triacrylates. An anti-$\beta$1 antibody was added to block the integrin ($\beta$1 receptor subunit over the 48-hour experiment in serum free media. Cells did not remain adhered on the triacrylates and BisGMA, while it had no significant effect on the tissue culture control. These results demonstrate that DPSCs adhere and proliferate specifically on triacrylates in an integrin-beta1-dependent manner.

Figure 13A:
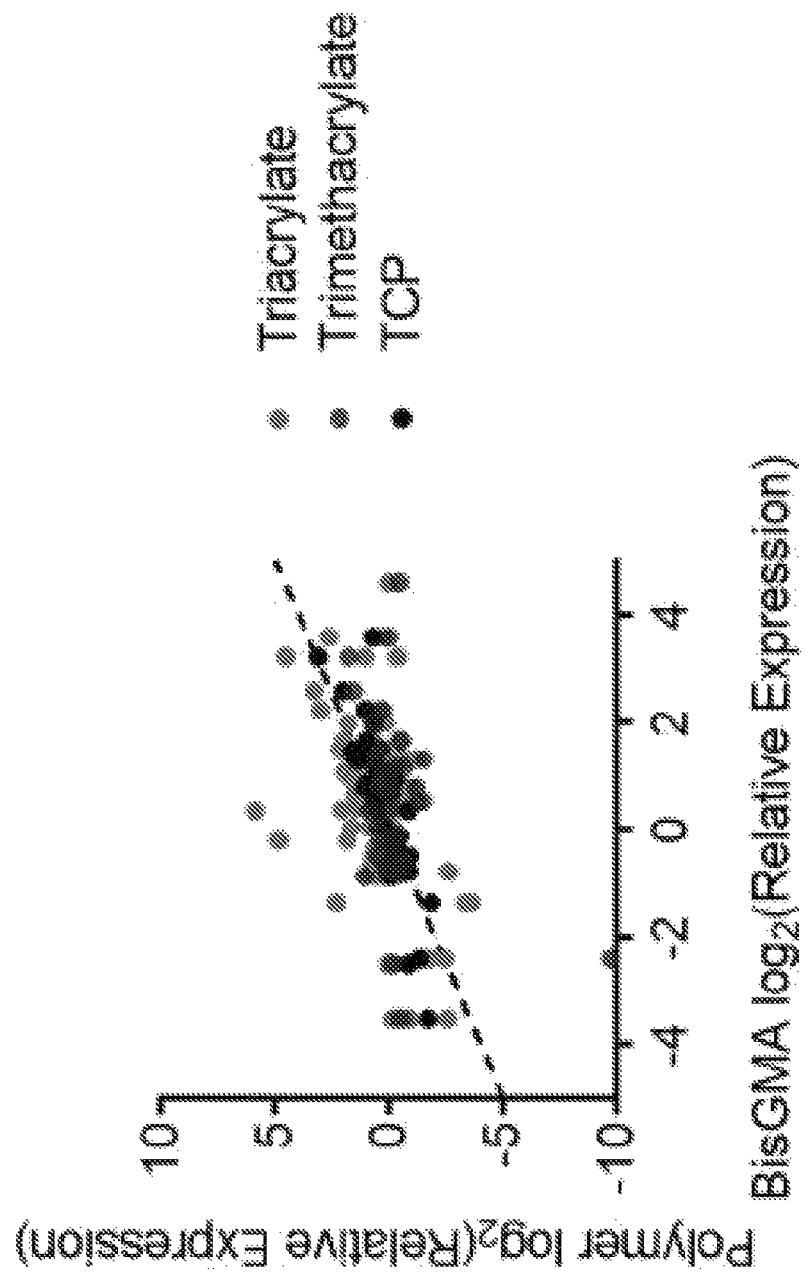
Figure 13B:
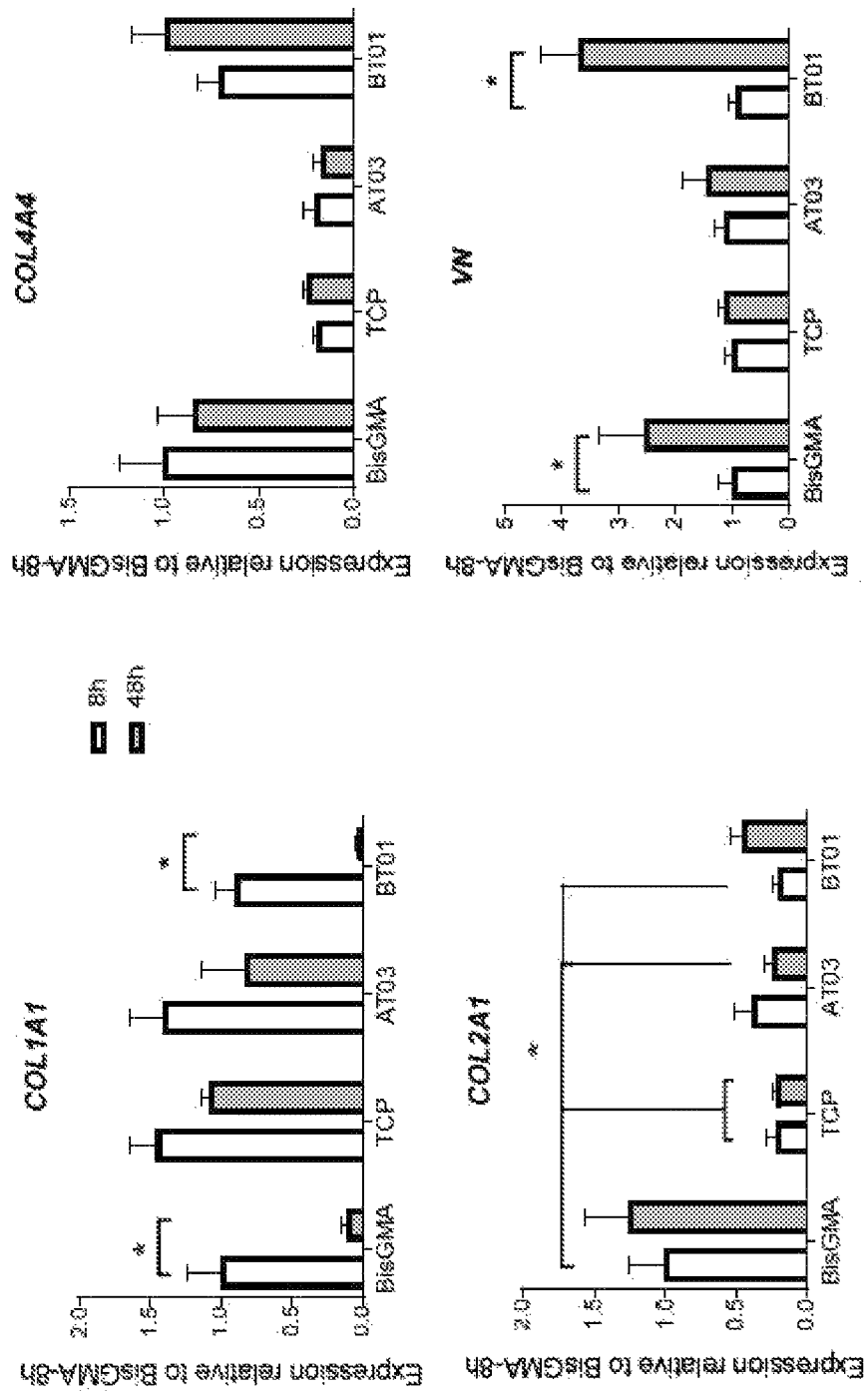
Figure 13C:
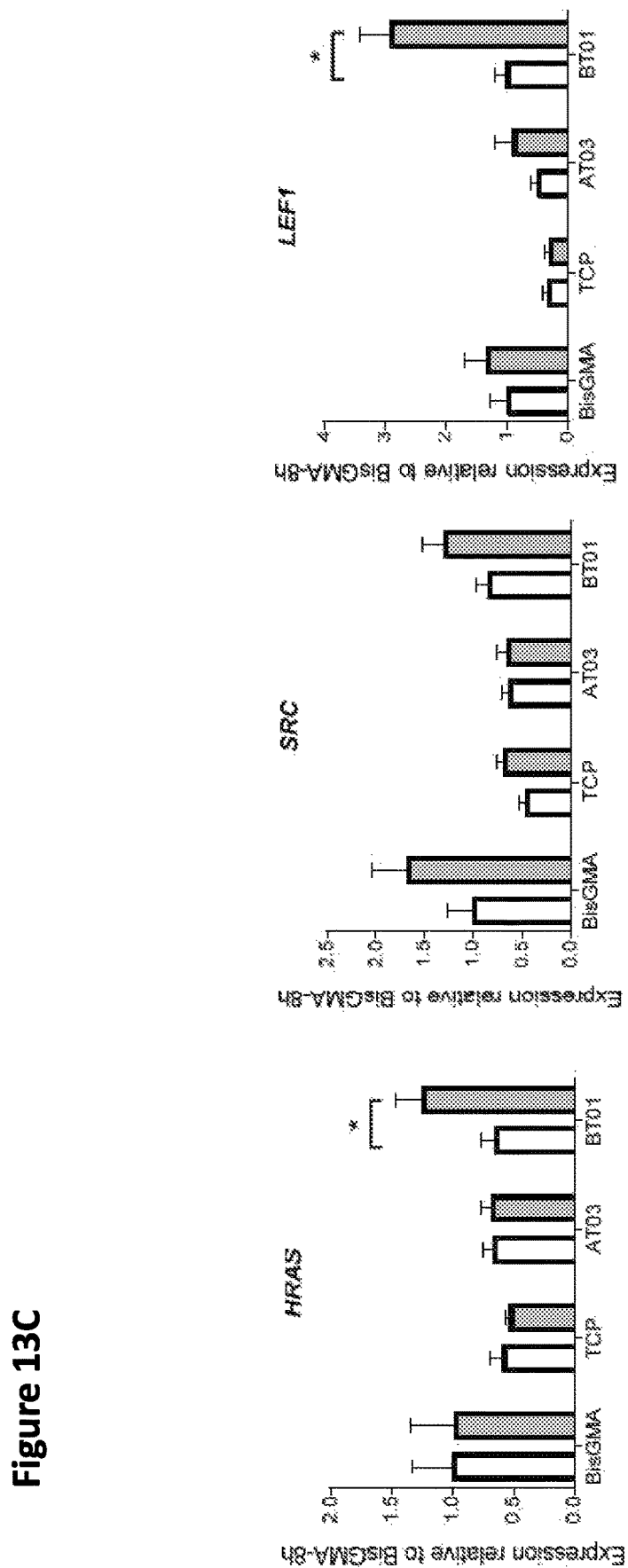

FIGS. 13A-C depict graphs demonstrating that DPSCs on triacrylates express extracellular matrix that enables their adhesion via ($\beta$1 signaling. FIG. 13A is a graph depicting expression levels of genes associated with ($\beta$1 signaling, including commonly expressed matrix proteins collagen 1, collagen 2, collagen 4, and vitronectin, in DPSCs at 8 and 48 hours. FIG. 13B are graphs depicting that COL1A1 expression is maintained on TCP and AT03, whereas COL4A4, COL2A1, and VN are increased on BisGMA and BT01. FIG. 13C are graphs depicting that DPSCs on BisGMA and BT01 upregulated expression of genes associated with cell stress and survival, HRAS, SRC, and LEF1, compared to TCP and AT03.

Figure 14A:
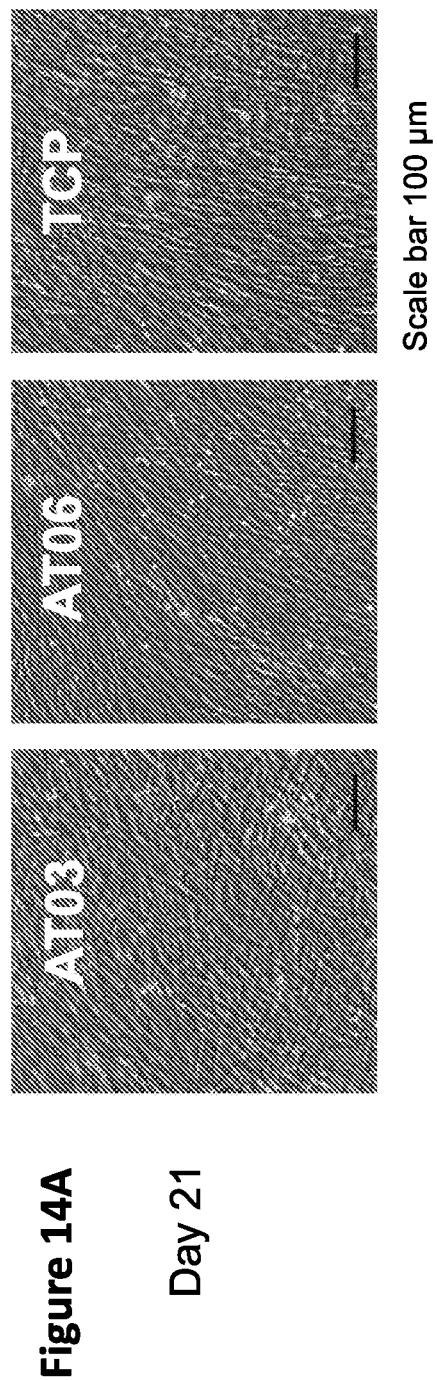
Figure 14B:
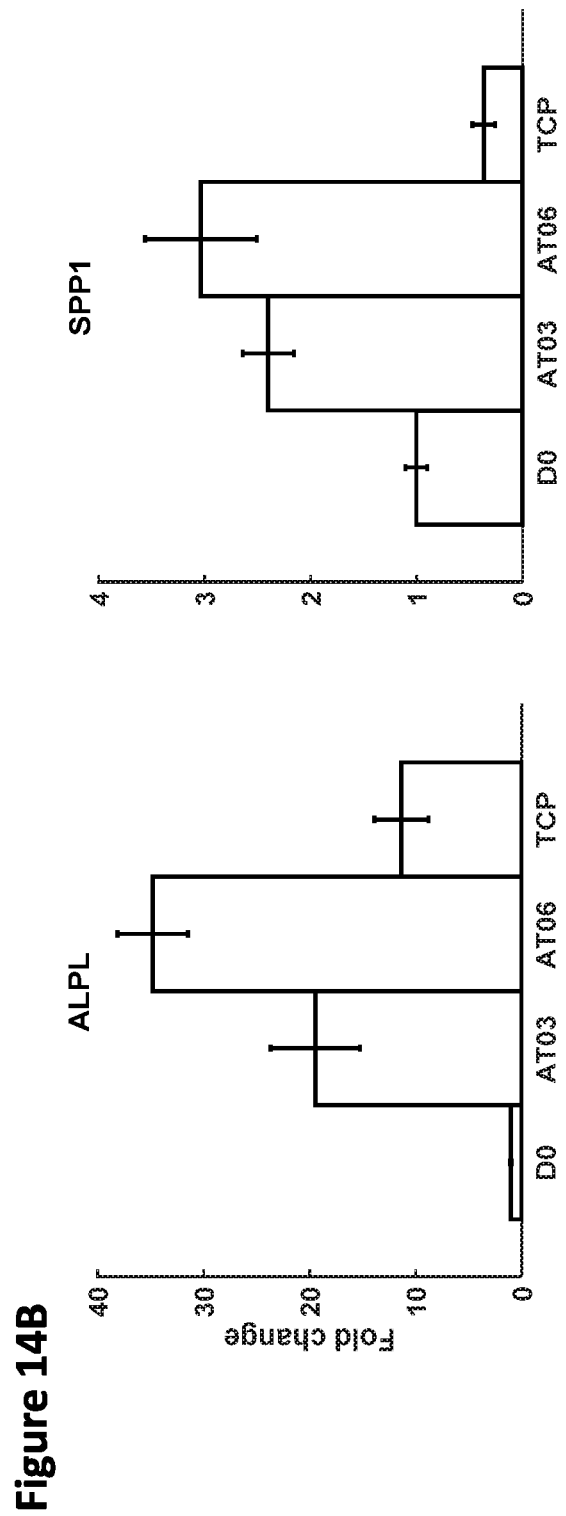

FIGS. 14A and 14B are graphs and images depicting differentiation of DPSCs on AT03 and AT06 under differentiation conditions. Specifically, DPSCs were seeded onto 12-well plates coated with polymers or tissue culture plastic control in serum-free conditions. After cells adhered and reached confluency over 72 hours, media was switched for differentiation conditions to differentiation media. Quantitative PCR analysis was performed for selected DPSC differentiation markers. FIG. 14A are images depicting phase contrast microscopic images of cells at Day 21 in differentiation media. FIG. 14B are graphs depicting the relative gene expression level of DPSC differentiation markers: ALPL (left) and SPP1 (right) in DPSCs on AT03, AT06 and TCP (positive control) in differentiation media. Data were normalized to a control sample at Day 0, and compared using two-way ANOVA with Turkey post-hoc comparisons test (N=6, $\alpha$=0.05). Values represent the mean and the standard error of the mean (SEM).

Figure 15:
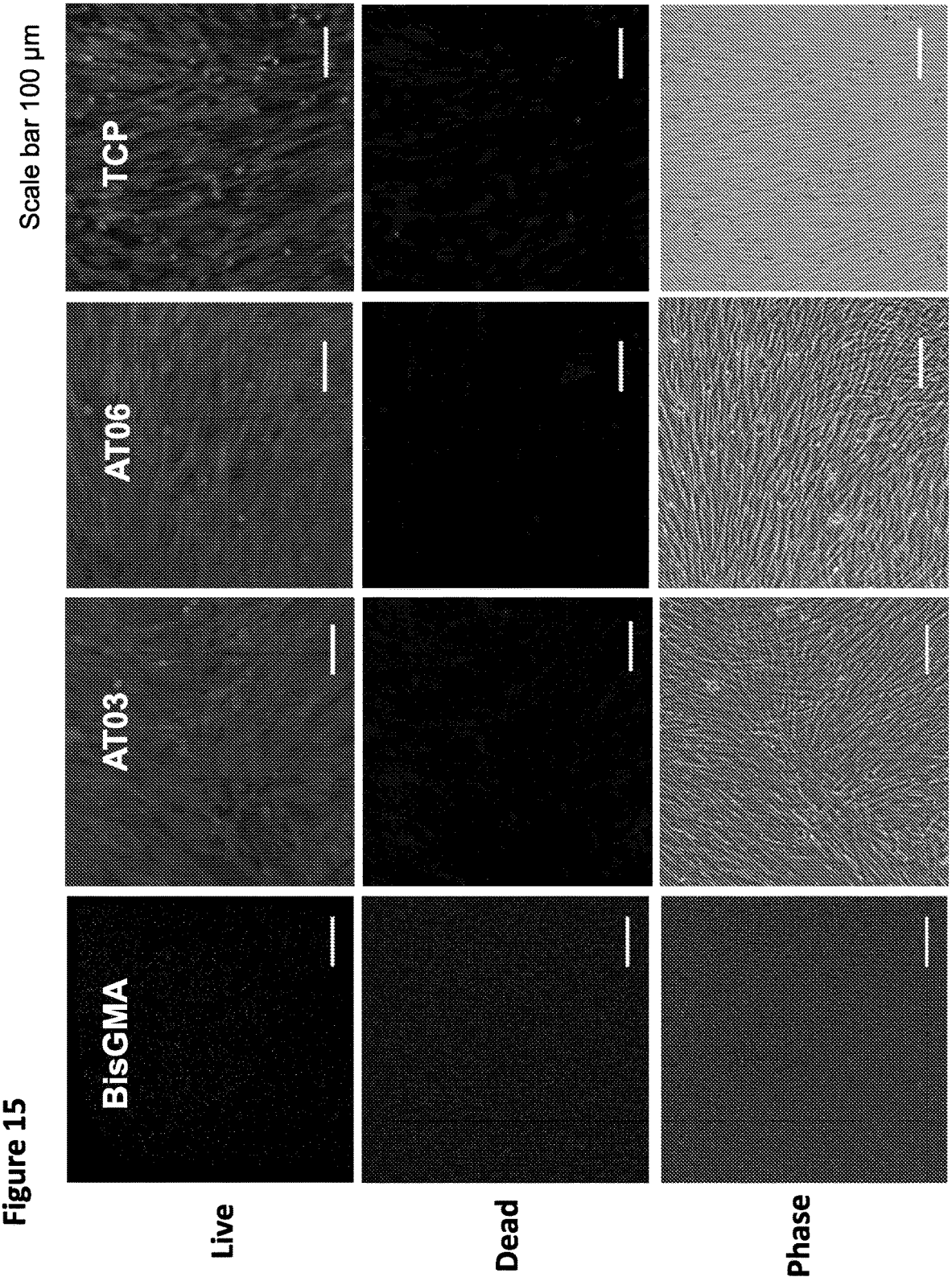

FIG. 15 are live/dead staining and phase contrast microscopic images depicting the adhesion of DPSCs on BisGMA, AT03, and AT06 and TCP under serum-free conditions. Specifically, DPSCs were seeded onto 12-well plates coated with polymers or tissue culture plastic control in serum-free conditions. Cells were stained for live cells with calcein AM and dead cells with ethidium homodimer-1, and imaged with phase contrast microscopy at 48 hours. Scale bar is 100 µm.

Figure 16A:
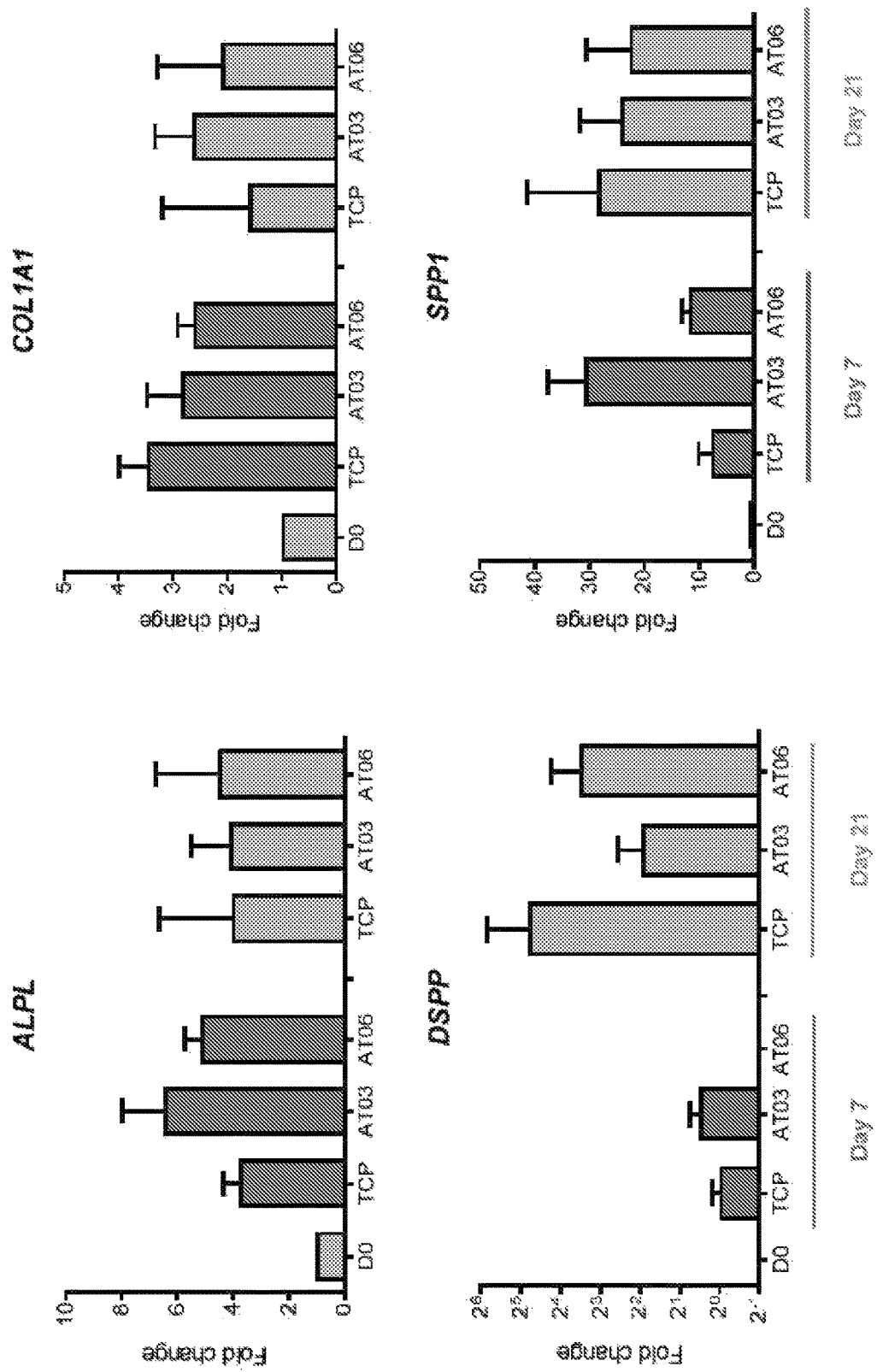
Figure 16B:
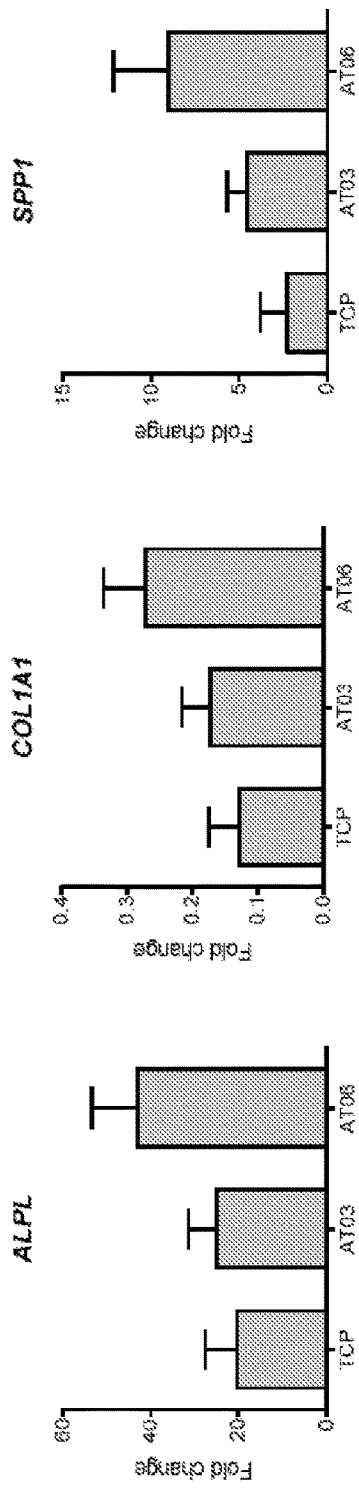
Figure 16C:
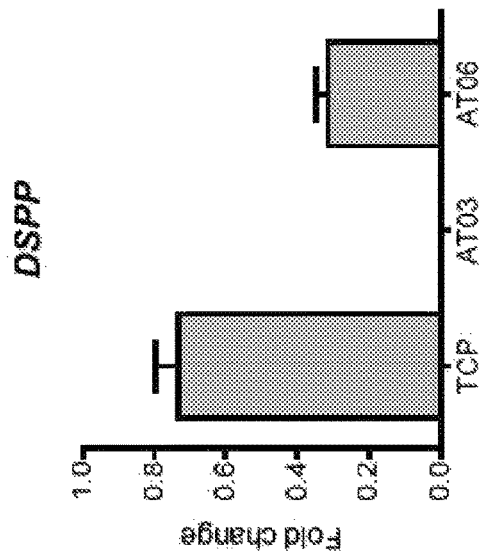

FIGS. 16A-C are graphs demonstrating that triacrylate polymers support DPSC differentiation and reparative dentin after dental pulp injury. FIGS. 16A and 16B are graphs depicting that DPSCs have the potential to regenerate dentin when adhered to the triacrylates AT03 and AT06. DPSCs on AT03 and AT06 expressed markers of osteogenic differentiation after long-term media in osteogenic media in FIG. 16B and expressed markers of odontoblasts that produce dentin, dentin sialophosphoprotein (DSPP), with the addition of TGFβ1 in FIG. 16A. Alkaline phosphatase (ALPL) and osteopontin (SPP1) was increased early on AT03 compared to TCP at Day 7. Collagen I expression (COL1A1) was similar across all tested conditions. FIG. 16C is a graph depicting that cells cultured without TGFβ1 did not show increased expression of DSPP after 21 days in osteogenic media.

Figure 17A:
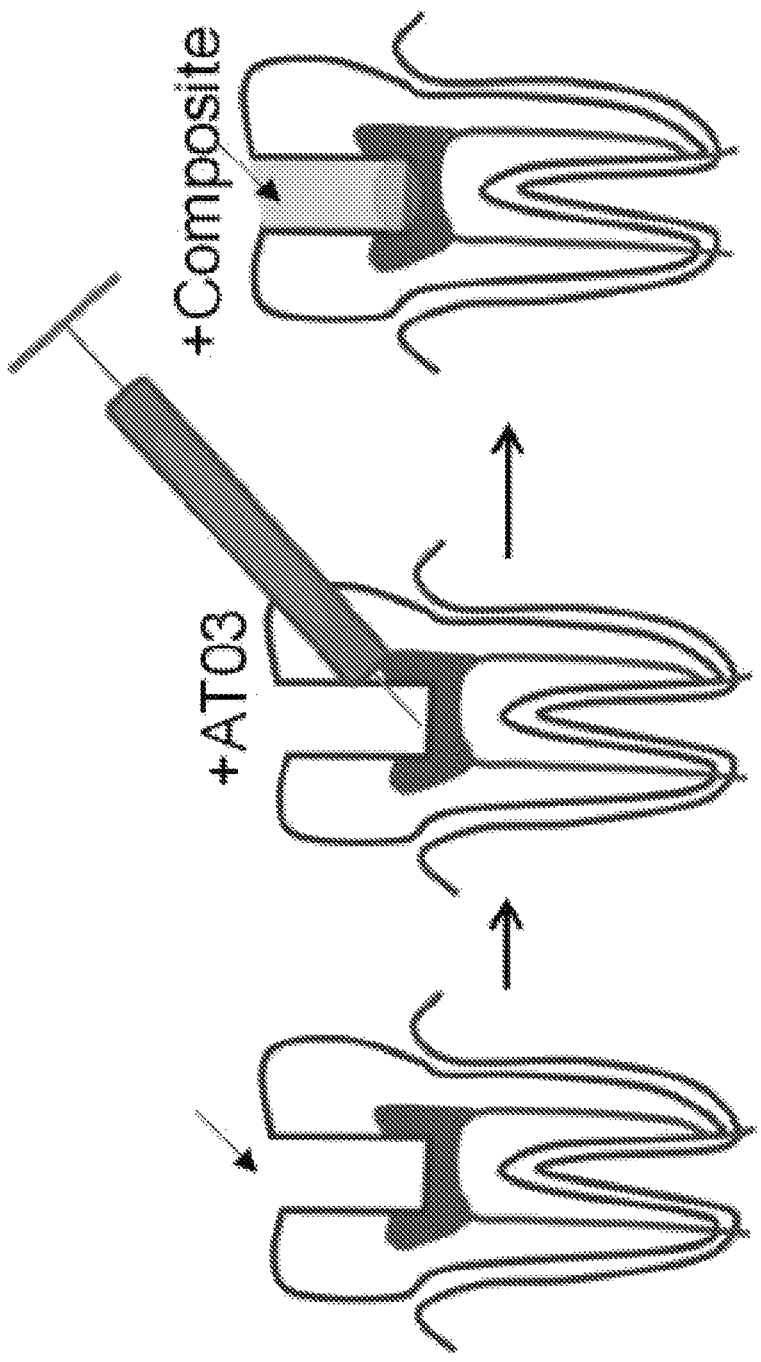
Figure 17B:
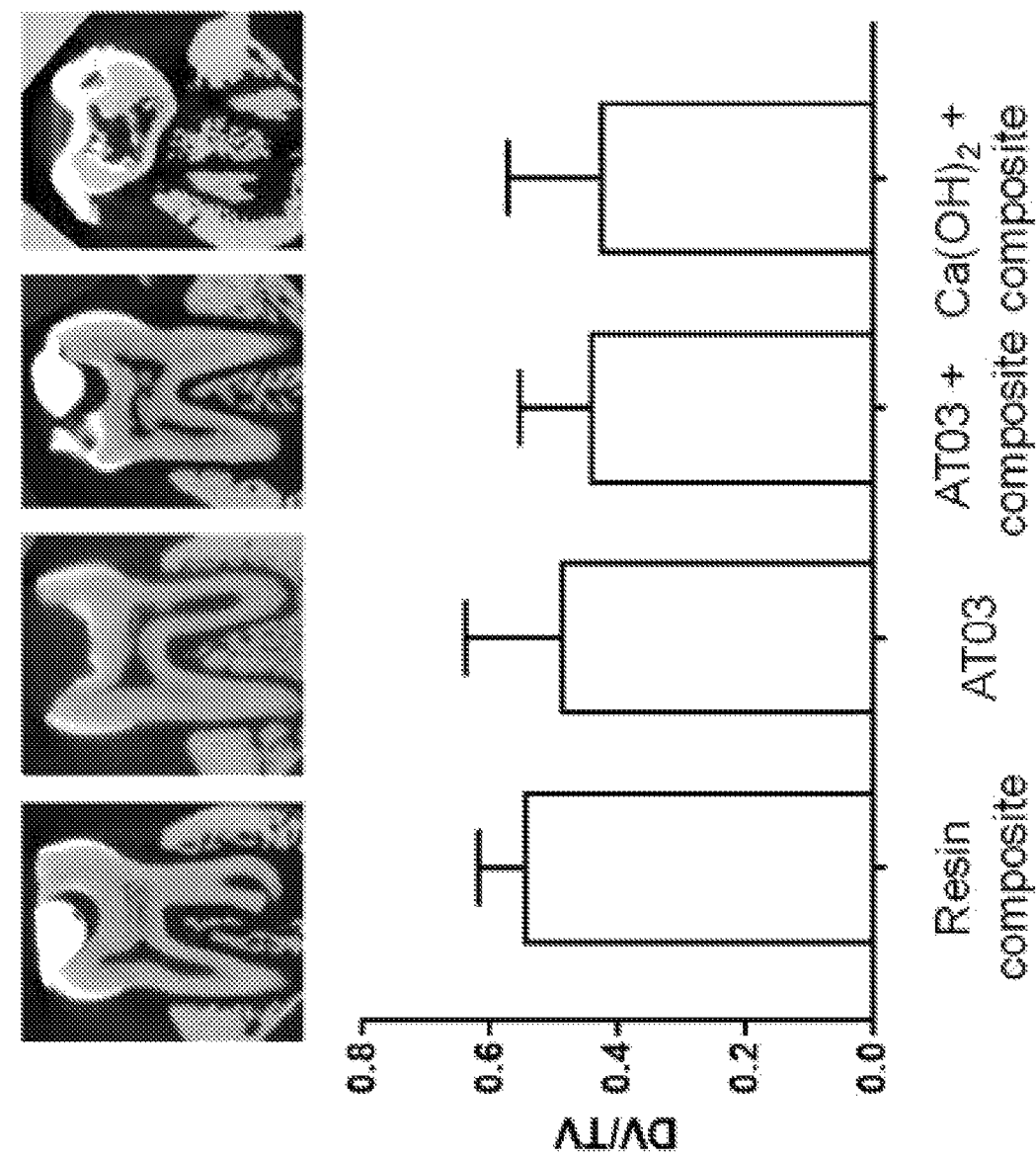
Figure 17C:
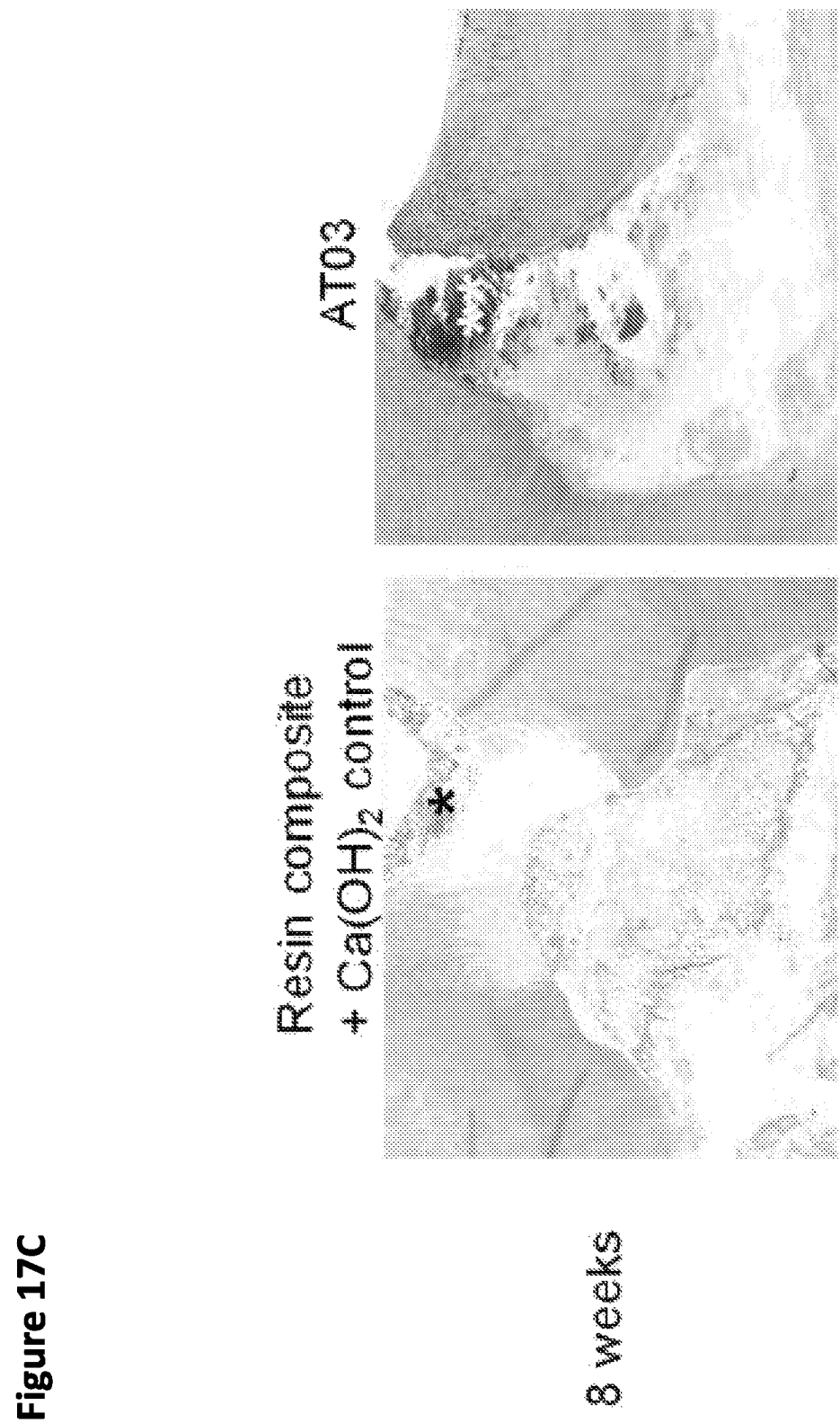
Figure 17D:
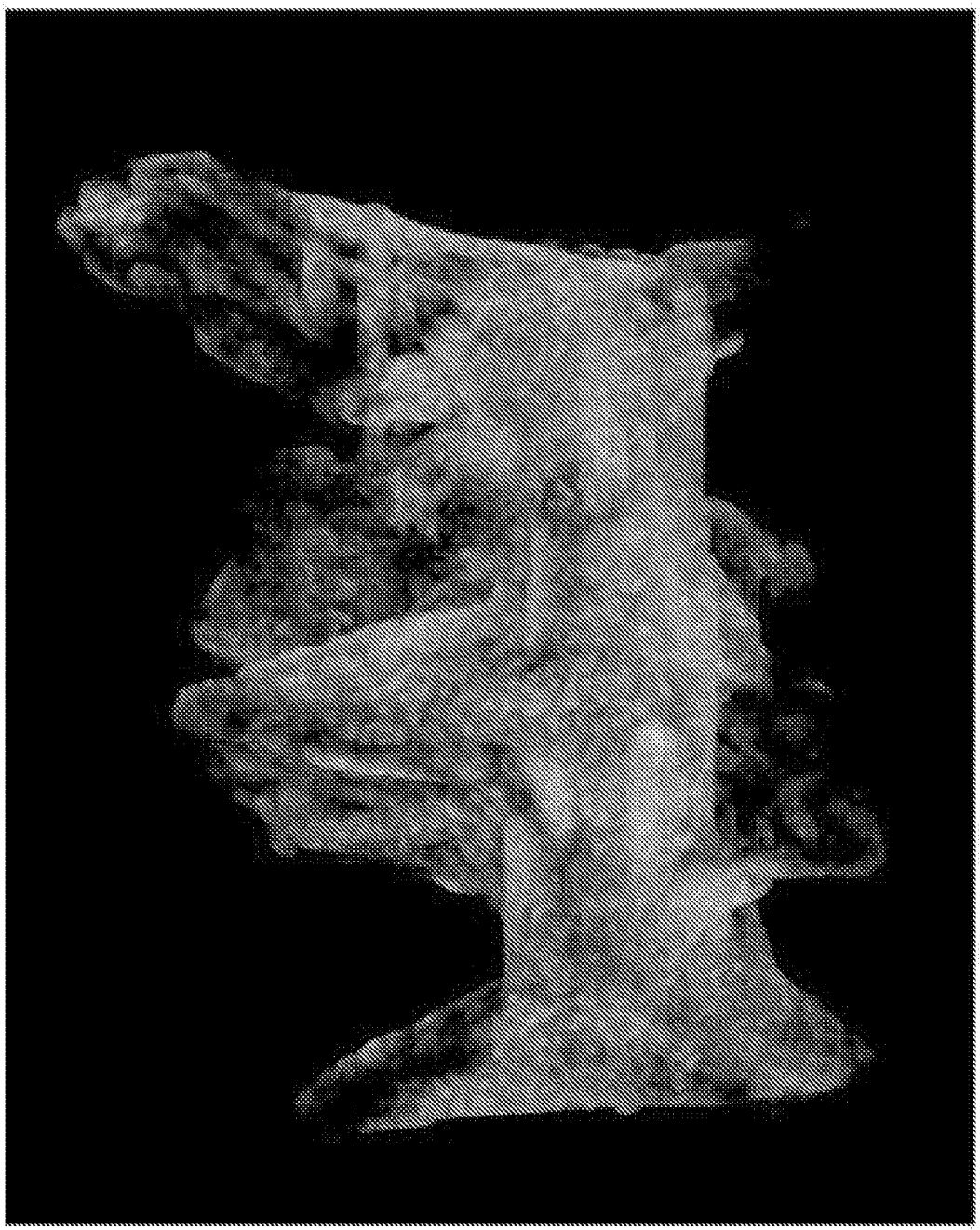

FIGS. 17A-D are graphs and images demonstrating the clinical potential of using AT03 therapeutically in dentistry in a rodent model of dental pulp injury. 6-week year old male SD rats were anesthetized and surgery was performed on their first and second molars to partial resect the pulp tissue. After proper isolation, the AT03-thiol prepolymer was applied to the cavity and cured inside the tooth (FIG. 17A). The control was application of a clinically used materials in dentistry a calcium hydroxide paste, dental adhesive, and a resin composite filling. Animals recovered from anesthesia and were sacrificed after 8 weeks. Dental tissues were properly fixed, imaged with microCT, and processed for histological hard tissue sectioning and staining. MicroCT images were processed to define the pulp volume and segment the mineralized opacities. Quantification of the dentin-to-pulp volume ratio showed no significant differences between conditions (FIG. 17B). Histologic sections showed that the pulp tissue became calcified and necrotic as a result of the partial pulpotomy, likely due to the severity of the surgical defect. The calcifications are consistent with reparative dentin formation. FIG. 17C depicts that the AT03 biomaterial (white asterisks) was retained in contact with the pulp tissue after 8 weeks and the pulp tissue qualitatively appeared similar to the calcium hydroxide and resin composite control (black asterisk). FIG. 17D depicts a representative three-dimensional reconstruction of the rat dental pulp volume from microCT images of a tooth restored with the AT03 triacryate polymer after 8 weeks.

Figure 18:
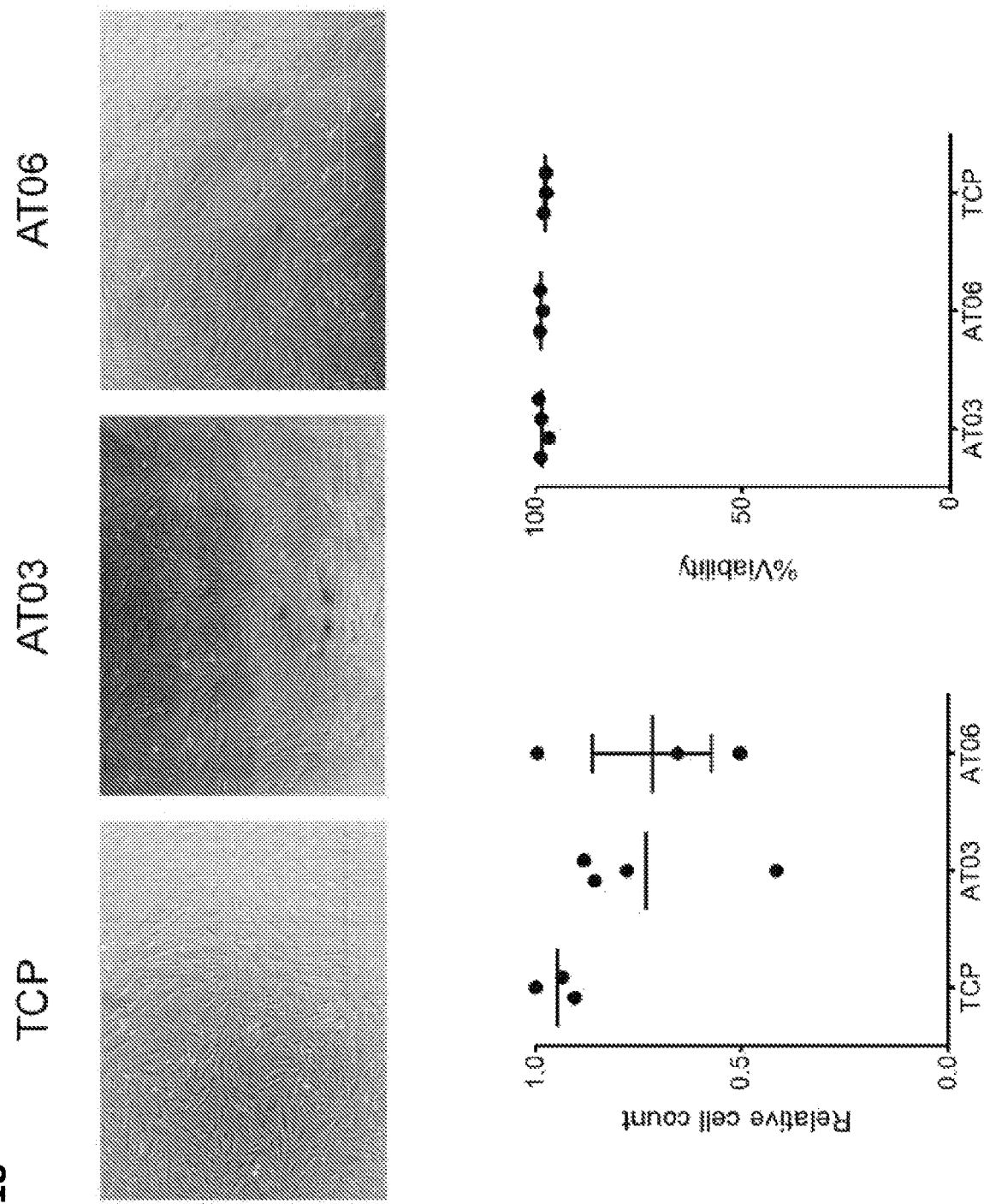

FIG. 18 are images and graphs demonstrating that triacrylate polymers AT03 and AT06 adhere primary human periodontal ligament fibroblasts similar to tissue culture control (TCP). Phase images show confluent monolayers, scale bar 1 mm. Imaging and cell counts of viable cells were performed after 48 hours.

DETAILED DESCRIPTION OF THE INVENTION

The present invention is based, at least in part, on the discovery of certain therapeutic biomaterials that are capable of promoting dentin and/or dental pulp repair and/or regeneration. In particular, the present inventors have surprisingly discovered that, in contrast to methacrylates or other acrylates, such as diacrylates, triacrylates are able to stimulate dental pulp stem cell (DPCS) adhesion, proliferation and/or differentiation, thus, facilitating the regeneration of dentin and/or dental pulp and preserving the vitality of the tooth.

Accordingly, the present invention provides methods and compositions for promoting repair and/or regeneration of a dental tissue in a subject in need thereof. Other embodiments of the invention include methods relating to promoting differentiation of dental pulp stem cells, and methods for treating a dental pulp infection in a subject in need thereof. In further embodiments, the invention includes methods for identifying a compound useful for dental tissue repair and/or regeneration, and methods for identifying a compound useful for treating dental infections. Novel modified triacrylates and uses thereof are also provided herein.

I. Definitions

In order that the present invention may be more readily understood, certain terms are first defined. In addition, it should be noted that whenever a value or range of values of a parameter are recited, it is intended that values and ranges intermediate to the recited values are also part of this invention.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

The articles "a" and "an" are used herein to refer to one or to more than one (i.e., to at least one) of the grammatical object of the article. By way of example, "an element" means one element or more than one element.

As used herein the term "comprising" or "comprises" is used in reference to compositions, methods, and respective component(s) thereof, that are essential to the invention, yet open to the inclusion of unspecified elements, whether essential or not.

The term "consisting of" refers to compositions, methods, and respective components thereof as described herein, which are exclusive of any element not recited in that description of the embodiment.

As used herein, a progenitor cell, e.g., a stem cell, is a relatively undifferentiated cell capable of self-renewal through mitotic cell division and also capable of differentiating into more specialized cell types. As is known in the art, stem cells include embryonic stem cells, which are totipotent, i.e., capable of differentiating into all cell types of the organism from which they were derived, and adult stem cells, which are pluripotent, i.e., capable of differentiating into almost all cell types including types from all three germ layers, multipotent, i.e., capable of differentiating into several cell types of a closely related family of cells, or unipotent, i.e., capable of differentiating into only one type of cell but distinguished from non-stem cells by the ability to self-renew by mitosis.

As used herein, a dental stem cell (DSC; also known as a tooth-derived stem cell) is a progenitor cell derived from vertebrate tooth pulp. A DSC can be from any tooth of any vertebrate that has teeth. In some embodiments, the dental stem cell is derived from a deciduous tooth. In other embodiments, the dental stem cell is derived from a premolar, a molar, an incisor or a canine. DSCs are capable of differentiating into cells of all three germ types and, thus, are pluripotent cells. In some embodiments, the DSCs are dental pulp stem cells (DPSCs).

As described herein, a dental tissue refers to dental pulp, coronal pulp (e.g., occlusal, mesial, distal, buccal, lingual or floor), radicular pulp, periapical tissue, periapical connective tissue, periodontal tissue, accessory canals, apical foramen, foramina, Zone of Rinaggio, zone of Weil, odontoblastic layer, bone, gum, blood vessels, nerves, nerve plexus of Raschkow, cementum, dentin, sclerotic dentin, tertiary dentin, reactionary dentin, reparative dentin, dentinal tubules, neodentin, or any tissues associated with dental pulp containing any of ameloblasts, fibroblasts, odontoblasts, or immune cells including, but not limited to, histiocytes, macrophage, granulocytes, mast cells or plasma cells.

As used herein, the term "dentin" refers to a calcified tissue of the body, and along with enamel, cementum, and dental pulp is one of the four major components of teeth. Dentin is usually covered by enamel on the crown and cementum on the root and surrounds the entire pulp. The formation of dentin, known as dentinogenesis, begins prior to the formation of enamel and is initiated by the odontoblasts of the pulp. An odontoblast is a cell found in the oral cavity of a mammal that produces dentin.

As used herein, the term "dental pulp" refers to a soft living tissue inside a tooth and is confined within the coronal region and root canals of the tooth. The dental pulp contains cells that provide odontogenic, nutritive, sensory and defensive functions to the mature pulp and allows the preservation of vitality during normal homeostatic maintenance and during wound repair after injury. The most predominant cell type in the dental pulp is the fibroblast, but the pulp also contains odontoblasts, blood cells, Schwann cells, endothelial cells, pericytes, undifferentiated mesenchymal cells or dental pulp stem cells. Cells involved in the immune response, such as macrophages, mast cells, antigen processing cells, dendritic cells, and plasma cells can also be found in the pulp during time of inflammation.

By "treatment", "prevention" or "amelioration" of a disease or disorder is meant delaying or preventing the onset of such a disease or disorder, reversing, alleviating, ameliorating, inhibiting, slowing or stopping the progression, aggravation or deterioration, the progression or severity of a condition associated with such a disease or disorder, e.g., a dental infection. In one embodiment, the symptoms of a disease or disorder are alleviated by at least 5%, at least 10%, at least 20%, at least 30%, at least 40%, or at least 50%.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. Preferably, the subject is a mammal. The mammal can be a human, non-human primate, mouse, rat, dog, cat, horse, or cow. Mammals other than humans can be advantageously used as subjects that represent animal models of dental diseases or injuries, or other related pathologies. A subject can be male or female. The subject can be an adult, an adolescent or a child. A subject can be one who has been previously diagnosed with or identified as suffering from or having a risk for developing an injury, disease or condition associated with dental tissue, such as dental trauma, dental infections, pulpitis or dental caries.

As used herein, the term "alkyl" refers to a fully saturated branched or unbranched hydrocarbon moiety. Preferably the alkyl comprises 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, or n-hexyl.

"Alkenyl" refers to an unsaturated hydrocarbon group which may be linear or branched and has at least one carbon-carbon double bond. Alkenyl groups with 2-6 carbon atoms can be preferred. The alkenyl group may contain 1, 2 or 3 carbon-carbon double bonds, or more. Examples of alkenyl groups include ethenyl, n-propenyl, isopropenyl, n-but-2-enyl, n-hex-3-enyl and the like.

"Alkynyl" refers to an unsaturated hydrocarbon group which may be linear or branched and has at least one carbon-carbon triple bond. Alkynyl groups with 2-6 carbon atoms can be preferred. The alkynyl group may contain 1, 2 or 3 carbon-carbon triple bonds, or more. Examples of alkynyl groups include ethynyl, n-propynyl, n-but-2-ynyl, n-hex-3-ynyl and the like.

The number of carbon atoms in a group is specified herein by the prefix "$C_{x-xx}$", wherein x and xx are integers. For example, "$C_{1-4}$alkyl" is an alkyl group which has from 1 to 4 carbon atoms.

"Aryl" by itself or as part of another substituent refers to a monovalent aromatic hydrocarbon group having the stated number of carbon atoms (i.e., $C_5$-$C_{14}$ means from 5 to 14 carbon atoms). Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octophene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthylene, and the like. In a specific embodiment, the aryl group is cyclopentadienyl, phenyl or naphthyl. In a more specific embodiment, the aryl group is phenyl or naphthyl.

As used herein, the term "heterocyclyl" refers to a saturated or unsaturated, monocyclic or bicyclic (e.g., fused, bridged or spiro ring systems) ring system which has from 3- to 11-ring members, or in particular 3 to 7 ring members, or in particular 4- to 9-ring members, at least one of which is a heteroatom, and up to 4 (e.g., 1, 2, 3, or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and sulfone. Heterocyclic rings include heteroaryl rings. As used herein, the term "heteroaryl" refers to an aromatic 3 or 11 membered monocyclic ring system, for example, a 5 or 6 membered monocyclic ring system, having 1 to 4 heteroatoms independently selected from O, S and N, and wherein N can be oxidized (e.g., N(O)) or quaternized, and S can be optionally oxidized to sulfoxide and sulfone. The heterocyclyl group can be attached at a heteroatom or a carbon atom. Examples of heterocyclyls include aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, dihydropyranyl, and heteroaryl rings including azirinyl, oxirenyl, thiirenyl, diazirinyl, azetyl, oxetyl, thietyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, and thiazepinyl and the like. Examples of bicyclic heterocyclic ring systems include 3-azabicyclo[3.1.0]hexanyl, 3-azabicyclo[3.1.1]heptanyl, 2-azaspiro[3.3]heptanyl, 2-oxa-6-azaspiro[3.3]heptanyl, and 5-azaspiro[2.3]hexanyl.

The term "cycloalkyl" refers to completely saturated monocyclic, bicyclic, fused or spiro hydrocarbon groups of 3-11 carbon atoms, or 4-9 carbon atoms. Exemplary monocyclic carbocyclyl groups include, but are not limited to, cyclopropyl, cyclobutyl, cyclopentyl, cyclohexyl, cycloheptyl, cyclopropenyl, cyclobutenyl, cyclopenentyl, cyclohexenyl, cycloheptenyl, cyclobutadienyl, cyclopentadienyl, cyclohexadienyl, cycloheptadienyl, phenyl and cycloheptatrienyl. Exemplary bicyclic carbocyclyl groups include bicyclo[2.1.1]hexyl, bicyclo[2.2.1]heptyl, bicyclo[2.2.1]heptenyl, tricyclo[2.2.1.0$^{2,6}$]heptanyl, 6,6-dimethylbicyclo[3.1.1]heptyl, or 2,6,6-trimethylbicyclo[3.1.1]heptyl, spiro[2.2]pentanyl, and spiro[3.3]heptanyl.

The term "bridged ring system," as used herein, is a ring system that has a carbocyclyl or heterocyclyl ring wherein two non-adjacent atoms of the ring are connected (bridged) by one or more (preferably from one to three) atoms selected from C, N, O, or S. A bridged ring system may have from 3-11 ring members.

The term "spiro ring system," as used herein, is a ring system that has two rings each of which are independently selected from a carbocyclyl or a heterocyclyl, wherein the two ring structures having one ring atom in common. Spiro ring systems have from 3 to 11 ring members.

The term "fused ring system," as used herein, is a ring system that has a carbocyclyl or heterocyclyl ring wherein two adjacent atoms of the ring are connected by two atoms selected from C, N, O, or S. A fused ring system may have from 3-11 ring members.

II. Compositions of the Invention

The present invention provides compositions for use in dental tissue repair and/or regeneration. The compositions include a triacrylate capable of promoting dental pulp stem cell (DPSC) adhesion and/or proliferation and optionally, a scaffold.

The compositions of the present invention comprise a triacrylate capable of promoting dental pulp stem cells adhesion and/or proliferation. The triacrylates of the present invention have significant and unique advantages compared with other types of polyfunctional acrylates, e.g., diacrylates. Unlike diacrylates, which cause severe pain and damage to the pulp and which are not suitable for use in dental tissue repair and/or regeneration, triacrylates have been demonstrated in the present invention to be capable of promoting adhesion and/or proliferation of dental pulp stem cells without any disturbance to the vitality of the cells. Indeed, these triacrylates have been shown to be able to induce differentiation of dental pulp stem cells into a mature and functional cell type, e.g., an odontoblast, which promotes the formation of dentin/pulp structure in a tooth. In addition, triacrylates are compatible with the dental pulp tissue, further indicating that these materials have a therapeutic potential for repair and/or regeneration of dental tissue in a subject in need thereof.

Examples of triacrylates suitable for use in the compositions of the present invention may include, but are not limited to, trimethylolpropane propoxylate triacrylate, trimethylolpropane triacrylate, pentaerythritol triacrylate, trimethylolpropane ethoxylate triacrylate, succinic acid triacrylate, or any other compounds that share a similar chemical structure, or a similar chemical or mechanical property as trimethylolpropane propoxylate triacrylate, trimethylolpropane triacrylate, pentaerythritol triacrylate, trimethylolpropane ethoxylate triacrylate, and/or succinic acid triacrylate, and combinations thereof.

In some embodiments, the triacrylate is trimethylolpropane propoxylate triacrylate as shown below:

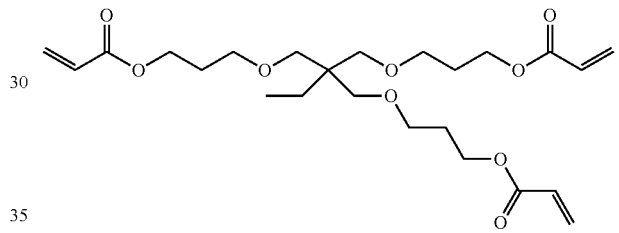

In other embodiments, the triacrylate is trimethylolpropane triacrylate as shown below:

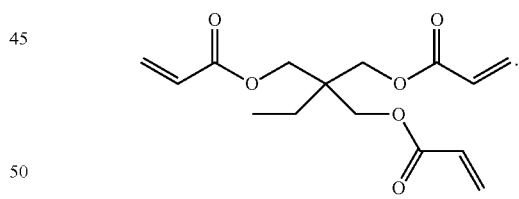

In some embodiments, the triacrylate is pentaerythritol triacrylate as shown below:

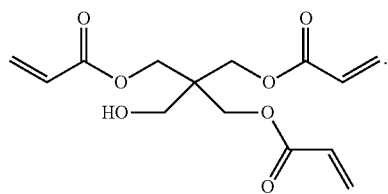 [SMILES: C=CC(=O)OCC(CO)(COC(=O)C=C)COC(=O)C=C]

In other embodiments, the triacrylate is trimethylolpropane ethoxylate triacrylate as shown below:

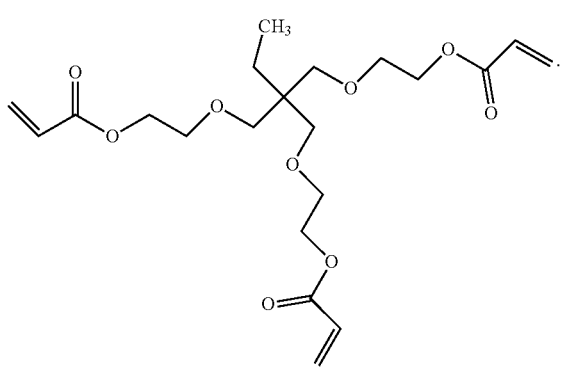 [SMILES: C=CC(=O)OCCOCC(CC)(COCCOC(=O)C=C)COCCOC(=O)C=C]

In yet another embodiment, the triacrylate is succinic acid triacrylate as shown below:

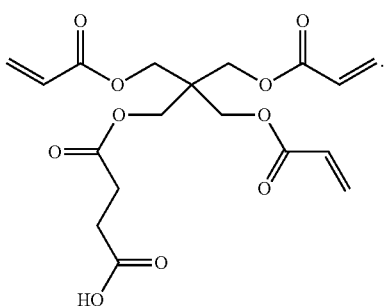 [SMILES: C=CC(=O)OCC(COC(=O)C=C)(COC(=O)C=C)COC(=O)CCC(=O)O]

In some embodiments, the triacrylate is a modified triacrylate. Modification of triacrylates can be performed by any known methods in the art, for example, via chemical reactions such as dehydration, nucleophilic substitution or elimination, and sulfur mediated substitution. In some embodiments, the triacrylate is modified by a reaction with an isocyanate to form a urethane bond. Triacrylates can be modified with any functional group known in the art. For example, a hydroxyl group and/or a carboxyl group on a triacrylate allows addition of a variety of functional groups onto the original triacrylate. Modification of triacrylates with additional chemistries may increase their ability to promote adhesion, migration, proliferation, differentiation of dental pulp stem cells (DPSCs), thus, further promoting dental tissue repair and/or regeneration.

In some embodiments, pentaerythritol triacrylate is modified as a compound of Formula I shown below:

[Formula I]

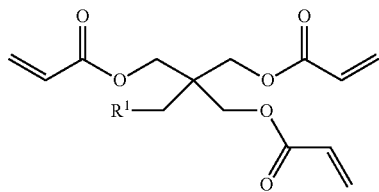

wherein $R^1$ is selected from the group consisting of —$COOR^a$, —$OCOR^a$, —$NR^aCOOR^a$, —$OCON(R^a)_2$, —$NR^bCOR^a$, —$CON(R^a)_2$, —$COR^a$ and —$NHCON(R^a)_2$;
$R^a$ is selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_2$-$C_{11}$heterocyclyl, $C_6$-$C_{14}$aryl, —$SR^b$, and —$OR^b$; wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_2$-$C_{11}$heterocyclyl, and $C_6$-$C_{14}$aryl groups are optionally substituted with one or four groups selected from the group consisting of hydrogen, halogen, hydroxy, cyano, amino, $C_1$-$C_{12}$alkyl, $C_1$-$C_{12}$alkoxy, $C_1$-$C_{12}$alkenyl, $C_1$-$C_{12}$alkynyl, $C_3$-$C_{12}$cycloalkyl, $C_2$-$C_{11}$heterocyclyl, $C_6$-$C_{14}$aryl, $C_1$-$C_{12}$alkylamino, di($C_1$-$C_{12}$alkyl)amino, —$COOR^a$, —$OCOR^a$, —$NR^cCOOR^c$, —$OCON(R^c)_2$, —$NR^cCOR^c$, —$CON(R^c)_2$, —$COR^c$ and —$NHCON(R^c)_2$;

$R^b$ is independently selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two $R^b$ groups may form a heterocyclyl with the nitrogen, oxygen, or sulfur to which they are connected, wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, amino, carboxy, $C_1$-$C_6$alkyl, $C_1$-$C_4$ carbonylamino, and $C_1$-$C_4$ alkoxy; and $R^c$ is independently selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two $R^c$ groups may form a heterocyclyl with the nitrogen or sulfur to which they are connected, wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, amino, carboxy, $C_1$-$C_6$alkyl, $C_1$-$C_4$ carbonylamino, and $C_1$-$C_4$ alkoxy.

In some embodiments, $R^1$ is —$OCON(R^a)_2$; wherein $R^a$ is selected from the group consisting of hydrogen and $C_1$-$C_8$alkyl; wherein the $C_1$-$C_6$alkyl is optionally substituted by one or four groups selected from halogen, hydroxy, amino, carboxy, $C_1$-$C_6$alkyl, $C_1$-$C_4$ carbonylamino, and $C_1$-$C_4$ alkoxy.

In some embodiments, $$R^1= \underset{O}{\overset{}{-O-\underset{\|}{C}-\overset{H}{\underset{}{N}}-(CH_2)_5 CH_3}}.$$

In some embodiments, $R^1$ is —$OCOR^a$; wherein $R^a$ is selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_2$-$C_{11}$heterocyclyl, $C_6$-$C_{14}$aryl, —$N(R^b)_2$, —$SR^b$, and —$OR^b$; wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_2$-$C_{11}$heterocyclyl, and $C_6$-$C_{14}$aryl groups are optionally substituted with one or four groups selected from the group consisting of hydrogen, halogen, hydroxy, cyano, amino, $C_1$-$C_{12}$alkyl, $C_1$-$C_{12}$alkoxy, $C_1$-$C_{12}$alkenyl, $C_1$-$C_{12}$alkynyl, $C_3$-$C_{12}$cycloalkyl, $C_2$-$C_{11}$heterocyclyl, $C_6$-$C_{14}$aryl, $C_1$-$C_{12}$alkylamino, di($C_1$-$C_{12}$alkyl)amino, —$COOR^c$, —$OCOR^c$, —$NR^cCOOR^c$, —$OCON(R^c)_2$, —$NR^cCOR^c$, —$CON(R^c)_2$, —$COR^c$ and —$NHCON(R^c)_2$;

wherein $R^b$ is independently selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two $R^b$ groups may form a heterocyclyl with the nitrogen, oxygen, or sulfur to which they are connected, wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, amino, carboxy, $C_1$-$C_6$alkyl, $C_1$-$C_4$ carbonylamino, and $C_1$-$C_4$ alkoxy; and $R^e$ is independently selected from the group consisting of hydrogen, halogen, $C_1$-$C_{12}$alkyl, $C_1$-$C_{12}$alkenyl, $C_1$-$C_{12}$alkynyl, $C_3$-$C_{12}$cycloalkyl, $C_2$-$C_{11}$heterocyclyl, and $C_6$-$C_{12}$aryl; wherein the $C_1$-$C_{12}$alkyl, $C_1$-$C_{12}$alkenyl, $C_1$-$C_{12}$alkynyl, $C_3$-$C_{12}$cycloalkyl, $C_2$-$C_{11}$heterocyclyl, and $C_6$-$C_{14}$aryl are optionally substituted from the group consisting of hydrogen, halogen, hydroxy, amino, carboxy, $C_1$-$C_4$ carbonylamino, and $C_1$-$C_4$ alkoxy. In some embodiments, the compound is of the following structural formula,

[Formula II]

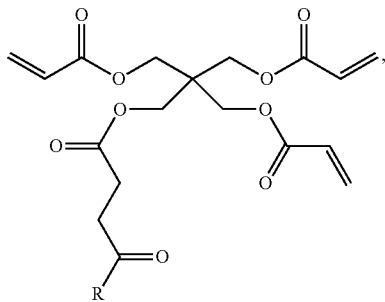

wherein R is selected from the group consisting of hydrogen, bromo, iodo, fluoro, $C_1$-$C_{12}$alkyl, $C_2$-$C_{12}$alkenyl, $C_2$-$C_{12}$alkynyl, $C_3$-$C_{12}$cycloalkyl, $C_2$-$C_{11}$heterocyclyl, $C_6$-$C_{14}$aryl, $N(R^d)_2$, —$SR^d$, and —$OR^e$; wherein the $C_1$-$C_{12}$alkyl, $C_2$-$C_{12}$alkenyl, $C_2$-$C_{12}$alkynyl, $C_3$-$C_{12}$cycloalkyl, $C_2$-$C_{11}$heterocyclyl, and $C_6$-$C_{14}$aryl groups are optionally substituted by one or more groups selected from the group consisting of halogen, hydroxy, cyano, amino, $C_1$-$C_{12}$alkyl, $C_1$-$C_{12}$alkenyl, $C_1$-$C_{12}$alkynyl, $C_1$-$C_{12}$alkoxy, $C_3$-$C_{12}$cycloalkyl, $C_2$-$C_{11}$heterocyclyl, $C_6$-$C_{14}$aryl, $C_1$-$C_{12}$alkylamino, and di($C_1$-$C_{12}$alkyl)amino;

$R^d$ is independently selected from the group consisting of hydrogen, $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two $R^d$ groups may form a heterocyclyl with the nitrogen to which they are connected, wherein the $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, and $C_1$-$C_4$ alkoxy; and $R^e$ is independently selected from the group consisting of $C_2$-$C_{12}$alkyl, $C_2$-$C_{12}$alkenyl, $C_2$-$C_{12}$alkynyl, benzyl, and phenyl, wherein the $C_2$-$C_{12}$alkyl, $C_2$-$C_{12}$alkenyl, $C_2$-$C_{12}$alkynyl, benzyl, and phenyl are optionally substituted from the group consisting of halogen, hydroxy, and $C_1$-$C_4$ alkoxy.

In some embodiments,

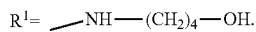

$R^1$= —NH—$(CH_2)_4$—OH.

The triacrylate can be a monomer or it can be polymerized. As used herein, the terms "polymerized" or "polymerization" refer to a process of reacting monomer molecules together in a chemical reaction to form polymer chains or three-dimensional networks. Polymerization of triacrylates can be performed by any methods known in the art, e.g., by photo-polymerization. In some embodiments, the triacrylate is polymerized prior to contacting a dental tissue. In other embodiments, the triacrylate is polymerized after contacting the dental tissue.

Photo-polymerization reactions are chain-growth polymerizations which are initiated by the absorption of visible or ultraviolet light. The light may be absorbed either directly by the reactant monomer, or else by a photoinitiator. Photoinitiators are compounds that upon radiation of light decompose into reactive species that activate polymerization of specific functional groups on the monomer. Photopolymerized systems are typically cured through ultraviolet (UV) radiation, since UV light is more energetic; however, the development of dye-based photoinitiator systems have allowed for the use of visible light, having potential advantages of processes that are more simple and safe to handle.

Photo-polymerization of triacrylate monomers can be performed with a thiol-ene crosslinker upon UV irradiation, as demonstrated in Example 1 below (FIG. 7). A thiol-ene crosslinker can be any compound having a thiol ('SH') functional group. Once the photoinitiator is activated upon exposure to light, the step growth (propagation and chain-transfer steps) and chain growth (homopolymerization) processes can be effectively used to form homogeneous polymer networks.

In some embodiments, the compositions of the present invention further comprise a scaffold. The scaffold may provide a matrix for cells to adhere and guide the process of tissue repair or regeneration in vivo. In some embodiments, the scaffold may comprise a particle that encapsulates the triacrylate. In some embodiments, the particle that encapsulates the composition is selected from the group consisting of a microsphere, a liposome, a microparticle, or combinations thereof.

Since the compositions of the present invention are suitable for delivering into a natural or artificial cavity or chamber of a tooth, the scaffold may have the shape of any mammalian tooth, or cavity or chamber therein. For example, a scaffold can have the shape of a human incisor, a human cuspid, a human bicuspid or a human molar, or a cavity or chamber therein.

A scaffold can be fabricated with any material recognized as useful by a skilled artisan. Suitable scaffold materials are discussed in, for example, Ma and Elisseeff, ed. (2005) Scaffolding in Tissue Engineering, CRC, ISBN 1574445219; Saltzman (2004) Tissue Engineering: Engineering Principles for the Design of Replacement Organs and Tissues, Oxford ISBN 019514130X. The entire contents of which are incorporated herein by reference. The materials utilized to fabricate the scaffold for use in the present invention can generally be categorized into three types: (1) naturally derived materials, including ECM molecules, such as collagens and hyaluronic acid, (2) polysaccharides, such as alginate, agars, agaroses, chitosan, and the like that can be formed into hydrogels of sufficient porosity to serve as tissue scaffolds, and (3) biocompatible synthetic materials including any of a variety of polymers or co-polymers, whether biodegradable or non-biodegradable, that do not elicit adverse affects when implanted into tissue.

Any one of a variety of naturally-derived scaffold-like materials may be used to provide a framework for dental tissue growth in accordance with the present invention. Because the scaffold, or substantial portions thereof, is applied to a natural or artificial cavity or chamber of a tooth in a subject, one will generally prefer to use a scaffold that is derived from a biological tissue that is compatible with the tooth. Such biocompatibility requires that the tissue scaffold does not cause any significant adverse or untoward reactions when administered to the subject. By using a biocompatible tissue scaffold significant immune responses and inflammatory reactions will be avoided.

A large number of naturally-derived tissue scaffold-like materials are available that may be used as scaffolds in accordance with this invention, including those scaffolds fabricated from human, animal or plant tissue. Potential advantages of these types of materials are their biocompatibility and their biological activity. As many of these molecules are found within tissues, they may not induce any foreign body reactions and are presumably receptive to the cell-mediated remodeling that occurs during tissue repair and regeneration (Yannas et al., 1989, Proc. Nat'l Acad. Sci. U.S.A. 86(3):933-7).

ECM molecules, such as collagen may be used as scaffold materials in for the compositions of the invention. Type I collagen, the most prevalent ECM molecule in the body, may be readily isolated from animal tissues and has been extensively utilized to fabricate cell delivery devices (Green et al., 1979, Proc. Natl. Acad. Sci. USA 76(11):5665-8; Yannas et al., 1981, Trans. Am. Soc. Artif. Intern. Organs, 27:19-23; Bell et al., 1981, Science 211 (4486):1052-4; Stem et al., 1990, J. Burn Care Rehabil., 11(1):7-13; Cavallaro et al., 1994, FEBS Lett., 350(2-3):216-8). This material can be processed into a wide variety of structures for use in the invention, e.g., films, sponges and fibers (Green et al., 1979, Proc. Natl. Acad. Sci. USA 76(11):5665-8; Yannas et al., 1981, Trans. Am. Soc. Artif. Intern. Organs, 27:19-23; Bell et al., 1981, Science 211 (4486):1052-4; Stem et al., 1990, J. Burn Care Rehabil., 11(1):7-13; Cavallaro et al., 1994, FEBS Lett., 350(2-3):216-8). The structure and resultant mechanical properties of collagen-based scaffolds can be regulated by the process utilized to extract the collagen from tissues (Cavallaro et al., 1994, FEBS Lett., 350(2-3):216-8), and by various crosslinking processes. Collagen molecules may be crosslinked physically by dehydrothermal (Koide et al., 1993, J. Biomed. Mater. Res., 27(1):79-87) or UV radiation treatments, or chemically by using various chemical agents (Cavallaro et al., 1994, FEBS Lett., 350(2-3):216-8; Koide et al., 1993, J. Biomed. Mater. Res., 27(1):79-87; DeLustro et al., 1990, Clin. Orthop. Relat. Res., (260):263-79). However, the inflammatory response to these materials and their erosion rate are dependent on the specific crosslinking agent that is utilized (Cavallaro et al., 1994, FEBS Lett., 350(2-3):216-8; Anselme, 1992; Koide et al., 1993, J. Biomed. Mater. Res., 27(1):79-87).

Polysaccharides may also be used as scaffolds in accordance with the compositions of the invention. Polysaccharides are carbohydrates characterized by the presence of a repeating structure in which the interunit linkages are of the O-glycoside type. The hydrophilicity of polysaccharides, along with the ease in which they can be formed into hydrogels, makes these materials ideal for use in the compositions of the invention. The variety of saccharide monomers and the variety of possible O-glycoside linkages result in a diversity of polysaccharide structures and conformations. Polysaccharides may be derived from different sources including plants (starch, cellulose), animal (glycogen), algae and seaweeds (alginate and agarose) and microorganisms.

Alginate, a polysaccharide isolated from seaweed, may also be used as a scaffold for the compositions of the present invention. Water soluble sodium alginate readily binds calcium, forming an insoluble calcium alginate hydrocolloid (Sutherland, 1991). These gentle gelling conditions have made alginate a popular material as an injectable cell delivery vehicle (Atala et al., 1994, J. Urol. 152(2 Pt 2):641-3). Accordingly, in some embodiment, the compositions of the present invention may be delivered by injection.

Synthetic polymers are attractive scaffold materials as they can be readily produced with a wide range of reproducible properties and structures. Polymer scaffolds also provide mechanical support against compressive and tensile forces, thus maintaining the shape and integrity of the scaffold in the environment of the tooth.

The morphology of the scaffold can guide the structure of an engineered tissue (Vacanti et al., 1988, J. Pediatr. Surg., 23(1 Pt 2):3-9), including the size, shape and vascularization of the tissue (Mooney et al., 1994, Cell Transplant, 3(2): 203-10; Mooney et al., 1995, 1 Biomed. Mater. Res., 29(8): 959-65; Mooney et al., 1996, Biotechnol. Prog., 12(6):865-8). The proper design of these scaffolds allows them to exhibit the required range of mechanical and biological functions. Synthetic polymeric materials can be precisely controlled in material properties and quality. Moreover, synthetic polymers can be processed with various techniques and supplied consistently in large quantities. The mechanical and physical properties of synthetic polymers can be readily adjusted through variation of molecular structures so as to fulfill their functions without the use of either fillers or additives.

Non-limiting examples of potentially useful materials for all or part of a scaffold used in the compositions of the invention include poly(ethylene) glycol, poly(lactide) (PLA), poly(glycolic acid) (PGA), poly(lactide-co-glycolide) (PLGA), poly($\alpha$-hydroxy acid), poly(caprolactone), polyanhydride, polyglactin, polycarbonates, polyamides, polyanhydrides, polyamino acids, polyorthoesters, polyacetals, polycyanoacrylates), polyphosphazene, degradable polyurethanes, polyacrylates, ethylene-vinyl acetate polymers and other acyl substituted cellulose acetates and derivatives thereof, polyurethanes, polystyrenes, polyvinyl chloride, polyvinyl fluoride, polyvinyl pyrrolidone, poly (vinylimidazole), chlorosulphonated polyolifins, polyethylene oxide, polyvinyl alcohol, Teflon®, nylon, agarose, alginate (e.g., calcium alginate gel), fibrin, fibrinogen, fibronectin, collagen (e.g., a collagen gel), gelatin, hyaluronic acid, chitin, and other suitable polymers and biopolymers, or analogs, mixtures, combinations, and derivatives of the above.

In some embodiments, the scaffold comprises a hydrogel. A hydrogel is understood to have a network of polymer chains that are hydrophilic, sometimes found as a colloidal gel in which water is the dispersion medium. Hydrogels can be highly absorbent (e.g., over about 80%, 85%, 90%, 95%, 99%, or 99.9% water) natural or synthetic polymers. Hydrogels can also possess a degree of flexibility similar to natural tissue, due to their significant water content. A hydrogel can include, for example, polyvinyl alcohol, sodium polyacrylate, acrylate polymers or copolymers with hydrophilic groups. Natural hydrogels can include agarose, methylcellulose, hyaluronan, or other naturally derived polymers.

In some embodiments, the hydrogel is selected from the group consisting of collagen, alginate, polysaccharide, gelatin, chitosan, hyaluronic acid (HA), polyethylene glycol (PEG), poly(glycolide) (PGA), poly(L-lactide) (PLA), poly (lactide-co-glycolide) (PLGA), and polylactic-coglycolic acid. In other embodiments, the hydrogel is an alginate.

In some embodiments, a scaffold used in the compositions of the present invention has a high porosity. Such a porous structure provides space for cell migration, adhesion, and the growth of new dental tissue.

Pores and channels of a scaffold can be engineered to be of various diameters. For example, the pores of the scaffold can have a diameter range from micrometers to millimeters. In some embodiments, the pores of the matrix material include microchannels. Microchannels can have an average diameter of about 0.1 µm to about 1,000 µm, e.g., about 50 µm to about 500 µm (for example about 100 µm, 150 µm, about 200 µm, about 250 µm, about 300 µm, about 350 µm, about 400 µm, about 450 µm, about 500 µm, or about 550 µm). One skilled in the art will understand that the distribution of microchannel diameters can have any distribution including a normal distribution or a non-normal distribution. In some embodiments, microchannels are a naturally occurring feature of the scaffold material(s). In other embodiments, microchannels are engineered to occur in the scaffold materials.

The compositions of the invention can be incorporated into a scaffold by any known method. In some embodiments, the triacrylates are imbedded in a gel, e.g., an alginate gel. For example, the triacrylate may be incorporated into the pores of an alginate gel.

Alternatively, the triacrylates of the invention may be chemically tethered to, or absorbed in, the scaffold by methods known in the art. Chemical modification methods may be used to covalently link the triacrylates on the surface of a scaffold. The surface functional groups of a scaffold can be coupled with reactive functional groups of the triacrylates to form covalent bonds using coupling agents well known in the art such as aldehyde compounds, carbodiimides, and the like. Additionally, a spacer molecule can be used to gap the surface reactive groups and the reactive groups of the triacrylates to allow more flexibility of such molecules on the surface of the scaffold. Other similar methods of attaching triacrylates to the interior or exterior of a scaffold will be known to one of skill in the art.

The composition of the present invention may further comprise a bioactive agent for repair and/or regeneration of a dental tissue. As used herein, "bioactive agents" refer to biological materials, for example, cytokines; growth factors; antibodies; antibiotics and differentiation factors.

In some embodiments, a bioactive agent is a compound selected from the group consisting of a chemotactic compound, an osteogenic compound, a dentinogenic compound, an amelogenic compound, a cementogenic compound, an angiogenic compound, an odontogenic compound, a neurogenic compound, and combinations thereof. As used herein, a chemotactic compound is a compound that attracts cells. An osteogenic compound is a compound that encourages new bone synthesis. A dentinogenic compound is a compound that encourages new dentin synthesis. An amelogenic compound is a compound that encourages tooth enamel synthesis. A cementogenic compound is a compound that encourages cementum synthesis. An angiogenic compound is a compound that encourages blood vessel formation. An odontogenic compound is a compound that encourages tooth formation. A neurogenic compound is a compound that encourages nerve formation. A composition described herein may include more than one bioactive agent, for example two, three, four, or more bioactive agents.

Non-limiting examples of additional bioactive agents suitable for inclusion in the compositions of the invention include platelet-derived growth factor (PDGF), endothelial cell growth factor (ECGF), transforming growth factor-β1 (TGF-β1), epidermal growth factor (EGF), stromal cell-derived factor-1 (SDF1), a bone morphogenetic protein (BMP), a growth and differentiation factor (GDF), insulin-like growth factor-1 (IGF1), vascular endothelial growth factor (VEGF), fibroblast growth factor (FGF), a dentin matrix protein, a dentin sialoprotein, a bone sialoprotein, amelogenin, an integrin, vascular endothelial growth factor (VEGF), basic fibroblast growth factor (bFGF), angiogenin, angiopoietin-1, del-1, follistatin, granulocyte colony-stimulating factor (G-CSF), hepatocyte growth factor/scatter factor (HGF/SF), interleukin-8 leptin, midkine, placental growth factor, platelet-derived endothelial cell growth factor (PD-ECGF), platelet-derived growth factor-BB (PDGF-BB), pleiotrophin (PTN), progranulin, proliferin, transforming growth factor-α (TGF-α), transforming growth factor-β (TGF-β), tumor necrosis factor-α (TNF-α), matrix metalloproteinase (MMP), angiopoietin 1 (ang1), ang2, delta-like ligand 4 (DLL4), connective tissue growth factor (CTGF), bone morphogenic protein (BMP), nerve growth factor (NGF), brain derived nerve factor (BDNF), NT-4, and NT-3.

A bioactive agent can be from any mammalian species. In some embodiments, the bioactive agent is a human bioactive agent, particularly when the mammal being treated is a human. The bioactive ingredient can be a recombinant bioactive agent.

In some embodiments, suitable bioactive agents include therapeutic agents. As used herein, the term "therapeutic agent" refers to a substance used in the diagnosis, treatment, or prevention of a disease, e.g., dental infections or diseases. Any therapeutic agent known to those of ordinary skill in the art to be of benefit in the diagnosis, treatment or prevention of a dental infection or disease is contemplated as a therapeutic agent in the context of the present invention. Therapeutic agents include pharmaceutically active compounds, hormones, growth factors, antibodies, anti-tumor drugs, antibiotics, anti-inflammatory agents, analgesic drugs or combinations thereof. Any of the therapeutic agents may be combined to the extent such combination is biologically compatible. Exemplified antibiotics may include, but not limited to, tetracyclines, penicillin, streptomycin, amoxicillin, augmentin, clindamycin, azithromycin and aureomycin. Exemplified analgesic may include, but not limited to, paracetamol, diclofenac, ketoprofen, aspirin, naproxen, indomethacin, ketorolac, ibuprofen, piroxicam, celecoxib, meloxicam, mefenemic acid, rofecoxib, and nimesulide.

Additional therapeutic agents may include, but are not limited to, those found in Harrison's Principles of Internal Medicine, 13th Edition, Eds. T. R. Harrison et al. McGraw-Hill N.Y., N.Y.; Physicians Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's The Pharmacological Basis of Therapeutics; and current edition of The Merck Index, the entire contents of all of which are incorporated herein by reference.

The amount of therapeutic agents included in a composition of the invention depends on various factors including, for example, the specific agent; function which it should carry out; required period of time for release of the agent; quantity to be administered. Generally, dosage of a therapeutic agent, i.e., amount of therapeutic agent in composition, is selected from the range of about 0.001% (w/w) to about 10% (w/w); about 1% (w/w) to about 5% (w/w); or about 0.1% (w/w) to about 1% (w/w).

In some embodiments, the compositions of the present invention may further comprise a cell, e.g. a dental pulp stem cell. Dental pulp stem cells are multi-potent neural crest-derived stem cells with therapeutic potential for dentin and/or dental pulp regeneration.

Dental pulp stem cells can be obtained from any tooth of any vertebrate that has teeth. In some embodiments, the dental pulp stem cell is derived from the pulp tissue from a baby tooth. In other embodiments, the dental pulp stem cell is derived from the pulp tissue from a premolar, a molar, an incisor or a canine. The dental pulp stem cells can differentiate into a more mature and functional cell, for example, an odontoblast. As described herein, an odontoblast is a cell found in the oral cavity of a mammal that initiates the process of dentinogensis, resulting in the formation of dentin. The dental pulp stem cells can produce a dentin and/or pulp tissue structure in vivo and in vitro.

One way to incorporate cells into the compositions is by incubating a triacrylate of the present invention in an aqueous solution comprising the cells to be incorporated. The aqueous solution can comprise enough cells to repair and/or regenerate dental tissue, e.g., from about $10^4$ to about $10^8$ cells/ml, about $10^4$ to about $10^6$ cells/m, about $10^6$ to about $10^8$ cells/ml, about $10^4$ cells/ml to about $10^5$ cells/ml, about $10^4$ cells/ml to about $10^7$ cells/ml, or about $10^5$ cells/ml to about $10^8$ cells/ml.

In some embodiments, the composition comprises more that one cell type. Cells amenable to be incorporated into the compositions of the invention include, but are not limited to, stem cells (embryonic stem cells, mesenchymal stem cells, dental stem cells, bone-marrow derived stem cells and hematopoietic stem cells), progenitor cells, vascular endothelial cells, endothelial progenitor cells, mesenchymal cells, ameloblasts, and neural stem cells, odontoblasts, or immune cells including, but not limited to, histiocytes, macrophage, granulocytes, mast cells or plasma cells.

In some embodiments, the cell is a genetically modified cell. A cell can be genetically modified to express and secrete a desired compound, e.g., a bioactive agent, a growth factor, differentiation factor, or a cytokine. Methods of genetically modifying cells for expressing and secreting compounds of interest are known in the art and easily adaptable by one of skill in the art.

An ordinary skill artisan in the art can locate, isolate and expand such cells. In addition, the basic principles of cell culture and methods of locating, isolation and expansion and preparing cells for tissue engineering are described in "Culture of Cells for Tissue Engineering" Editor(s): Gordana Vunjak-Novakovic, R. Ian Freshney, 2006 John Wiley & Sons, Inc., and in "Cells for tissue engineering" by Heath C. A. (Trends in Biotechnology, 2000, 18:17-19), the entire contents of all of which are incorporated herein by reference.

In some embodiments, the compositions of the present invention are free of a bioactive agent. In those embodiments, application of a triacrylate and a plurality of dental pulp stem cells to the dental tissue is sufficient to enhance DPSC adhesion, proliferation and/or differentiation, thus promoting repair and/or regeneration of dental tissue.

In some embodiments, the compositions of the present invention may be combined with existing dental composite materials to provide an additional effect to the existing material, and could potentially lead to enhanced dental tissue repair and/or regeneration.

The compositions of the present invention are suitable for delivering to a natural or artificial cavity or chamber of a tooth in a subject. Delivery of the compositions to a subject can be accomplished by any appropriate route known in the art. As used herein, the term "delivery" refers to the placement of a composition into a subject by a method or route which results in at least partial localization of the composition at a desired site such that a desired effect is produced.

Exemplary modes of delivery include, but are not limited to, injection, insertion, implantation, or delivery within a scaffold that encapsulates the composition of the invention at the target tissue, e.g., dental tissue. In some embodiments, the composition is delivered to a natural or artificial cavity or chamber of a tooth of a subject by injection. When the compositions of the invention are dissolved in a solution, they can be injected into the dental tissue by a syringe. In some embodiments, the compositions are polymerized prior to delivery. In other embodiments, the composition may be delivered as a monomer, wherein the monomer is polymerized upon delivering into a natural or artificial cavity or chamber of a tooth by in situ polymerization.

The compositions of the invention can alternatively be introduced into or onto a tooth, or chamber or cavity therein, via a carrier based system, such as an encapsulation vehicle. For example, the compositions can be micro-encapsulated to provide for enhanced stability or prolonged delivery. Encapsulation vehicles include, but are not limited to, microparticles, liposomes, microspheres, or the like, or a combination of any of the above to provide the desired release profile in varying proportions.

Polymeric microspheres can be produced using naturally occurring or synthetic polymers and are particulate systems in the size range of 0.1 to 500 µm. Polymeric micelles are polymeric delivery vehicles with similar characteristics to microspheres and can also facilitate encapsulation and matrix integration of a compound described herein. Fabrication, encapsulation, and stabilization of microspheres for a variety of payloads are within the skill of the art (see e.g., Varde & Pack (2004) *Expert Opin. Biala* 4(1) 35-51). Polymer materials useful for forming microspheres include PIA, PLGA, PLGA coated with DPPC, DPPC, DSPC, EVAc, gelatin, albumin, chitosan, dextran, DL-PLG, SDLMs, PEG (e.g., ProMaxx), sodium hyaluronate, diketopiperazine derivatives (e.g., Technosphere), calcium phosphate-PEG particles, and/or oligosaccharide derivative DPPG (e.g., Solidose). Encapsulation can be accomplished, for example, using a water/oil single emulsion method, a water-oil-water double emulsion method, or lyophilization. Several commercial encapsulation technologies are available (e.g., ProLease®, Alkerme).

Liposomes can also be used to encapsulate and deliver the compositions of the invention. Conventional liposomes are composed of neutral or anionic lipids (natural or synthetic). Commonly used lipids are lecithin such as phosphatidylcholines, phosphatidylethanolamines, sphingomyelins, phosphatidylserines, phosphatidylglycerols, and phosphatidylinositols. Liposome encapsulation methods are commonly known in the arts (Galovic et cal. (2002) *Eur. J. Pharin. Sci.* 15, 441-448; Wagner et al. (2002) *J. Liposome Res.* 12, 259-270). Targeted liposomes and reactive liposomes can also be used. Reactive or polymorphic liposomes include a wide range of liposomes, the common property of which is their tendency to change their phase and structure upon a particular interaction (e.g., pH-sensitive liposomes). See, e.g., La sic (1997) Liposomes in Gene Delivery, CRC Press, Fla.)

The compositions of the present invention are also suitable as cell culture substrates. Biological studies in vitro use polymer substrates to adhere and culture cells. Surface chemistry regulates how cells interact with these materials. Currenity, plasma-treated polystyrene is widely used in cell studies due it its ability to adsorb proteins from serum and proteins expressed by cells, which are required for cell adhesion and function. However, it is not well understood how treated-polystyrene affects the biology of the cells. Additionally, plasma treatment alters the surface chemistry by adding polar chemical groups in an uncontrolled manner and adds to manufacturing costs. The present inventor surprisingly discovered that the compositions of the present invention, e.g., triacrylate, are suitable as cell culture substrates, without any additional surface modifications. Further, these triacrylates provide a more physiologic substrate for cells in vitro, without requiring additional surface treatments, compared with tissue culture plastic. Culturewares that are coated with triacrylates and are cured with UV light are highly scalable with commercial manufacturing.

The present invention also provides novel compounds of Formula II, or a pharmaceutically acceptable salt thereof, comprising the structure:

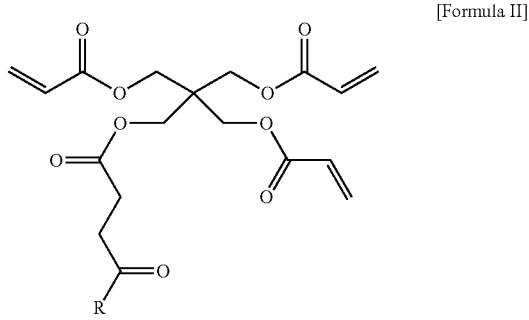

[Formula II]

wherein R is selected from the group consisting of hydrogen, bromo, iodo, fluoro, $C_1$-$C_{12}$alkyl, $C_2$-$C_{12}$alkenyl, $C_2$-$C_{12}$alkynyl, $C_3$-$C_{12}$cycloalkyl, $C_2$-$C_{11}$heterocyclyl, $C_6$-$C_{14}$aryl, $N(R^d)_2$, —$SR^d$, and —$OR^e$; wherein the $C_1$-$C_{12}$alkyl, $C_2$-$C_{12}$alkenyl, $C_2$-$C_{12}$alkynyl, $C_3$-$C_{12}$cycloalkyl, $C_2$-$C_{11}$heterocyclyl, and $C_6$-$C_{14}$aryl groups are optionally substituted by one or more groups selected from the group consisting of halogen, hydroxy, cyano, amino, $C_1$-$C_{12}$alkyl, $C_1$-$C_{12}$alkenyl, $C_1$-$C_{12}$alkynyl, $C_1$-$C_{12}$alkoxy, $C_3$-$C_{12}$cycloalkyl, $C_2$-$C_{11}$heterocyclyl, $C_6$-$C_{14}$aryl, $C_1$-$C_{12}$alkylamino, and di($C_1$-$C_{12}$alkyl)amino;

$R^d$ is independently selected from the group consisting of hydrogen, $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two $R^d$ groups may form a heterocyclyl with the nitrogen to which they are connected, wherein the $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, and $C_1$-$C_4$ alkoxy; and $R^e$ is independently selected from the group consisting of $C_2$-$C_{12}$alkyl, $C_2$-$C_{12}$alkenyl, $C_2$-$C_{12}$alkynyl, benzyl, and phenyl, wherein the $C_2$-$C_{12}$alkyl, $C_2$-$C_{12}$alkenyl, $C_2$-$C_{12}$alkynyl, benzyl, and phenyl are optionally substituted from the group consisting of halogen, hydroxy, and $C_1$-$C_4$ alkoxy.

In some embodiments, R is selected from the groups consisting of hydrogen, bromo, iodo, fluoro, $C_1$-$C_6$alkyl, $C_2$-$C_6$alkenyl, $C_2$-$C_6$alkynyl, $C_3$-$C_8$cycloalkyl, $C_2$-$C_6$heterocyclyl, $C_6$-$C_{12}$aryl, —$N(R^d)_2$, —$SR^d$, and —$OR^e$; wherein $C_1$-$C_6$alkyl, $C_2$-$C_6$alkenyl, $C_2$-$C_6$alkynyl, $C_3$-$C_6$cycloalkyl, $C_2$-$C_6$heterocyclyl, $C_6$-$C_{12}$aryl are optionally substituted by one to four groups selected from halogen, hydroxy, and $C_1$-$C_4$ alkoxy;

$R^d$ is independently selected from the groups consisting of hydrogen, $C_1$-$C_6$alkyl, $C_3$-$C_8$cycloalkyl, $C_6$-$C_{14}$aryl, and $C_2$-$C_{11}$heterocyclyl, wherein the $C_1$-$C_6$alkyl, $C_3$-$C_8$cycloalkyl, $C_6$-$C_{14}$aryl, and $C_2$-$C_{11}$heterocyclyl are optionally substituted by one of more groups selected from halogen, hydroxy, and $C_1$-$C_4$ alkoxy; and $R^e$ is independently selected from the groups consisting of $C_2$-$C_6$alkyl, benzyl, and phenyl, the $C_2$-$C_6$alkyl, benzyl, and phenyl are optionally substituted from the groups consisting of halogen, hydroxy, and $C_1$-$C_4$ alkoxy.

In some embodiments, R is selected from the group consisting of hydrogen, $C_1$-$C_{12}$alkyl, $C_2$-$C_{12}$alkenyl, $C_2$-$C_{12}$alkynyl, $C_3$-$C_{12}$cycloalkyl, $C_2$-$C_{11}$heterocyclyl, $C_6$-$C_{14}$aryl, —$N(R^d)_2$, —$SR^d$, and —$OR^e$; wherein the $C_1$-$C_{12}$alkyl, $C_2$-$C_{12}$alkenyl, $C_2$-$C_{12}$alkynyl, $C_3$-$C_{12}$cycloalkyl, $C_2$-$C_{11}$heterocyclyl, and $C_6$-$C_{14}$aryl groups are optionally substituted by one or more groups selected from the group consisting of halogen, hydroxy, cyano, amino, $C_1$-$C_{12}$alkyl, $C_1$-$C_{12}$alkenyl, $C_1$-$C_{12}$alkynyl, $C_1$-$C_{12}$alkoxy, $C_3$-$C_{12}$cycloalkyl, $C_2$-$C_{11}$heterocyclyl, $C_6$-$C_{14}$aryl, $C_1$-$C_{12}$alkylamino, and di($C_1$-$C_{12}$alkyl)amino;

$R^d$ is independently selected from the group consisting of hydrogen, $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two $R^d$ groups may form a heterocyclyl with the nitrogen to which they are connected, wherein the $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, and $C_1$-$C_4$ alkoxy; and $R^e$ is independently selected from the group consisting of $C_2$-$C_{12}$alkyl, $C_2$-$C_{12}$alkenyl, $C_2$-$C_{12}$alkynyl, benzyl, and phenyl, wherein the $C_2$-$C_{12}$alkyl, $C_2$-$C_{12}$alkenyl, $C_2$-$C_{12}$alkynyl, benzyl, and phenyl are optionally substituted from the group consisting of halogen, hydroxy, and $C_1$-$C_4$ alkoxy.

In some embodiments, R is selected from the group consisting of hydrogen, $C_1$-$C_{12}$alkyl, —$N(R^d)_2$, —$SR^d$, and —$OR^e$; wherein the $C_1$-$C_{12}$alkyl is optionally substituted by one or more groups selected from the group consisting of halogen, hydroxy, cyano, amino, $C_1$-$C_{12}$alkyl, $C_1$-$C_{12}$alkylamino, and di($C_1$-$C_{12}$alkyl)amino;

$R^d$ is independently selected from the group consisting of hydrogen and $C_1$-$C_{12}$alkyl, or wherein the two $R^d$ groups may form a heterocyclyl with the nitrogen to which they are connected, wherein the $C_1$-$C_{12}$alkyl is optionally substituted by one of more groups selected from halogen, hydroxy, and $C_1$-$C_4$ alkoxy; and $R^e$ is independently selected from the group consisting of $C_2$-$C_{12}$alkyl, benzyl, and phenyl, wherein the $C_2$-$C_{12}$alkyl, benzyl, and phenyl are optionally substituted from the group consisting of halogen, hydroxy, and $C_1$-$C_4$ alkoxy.

In some embodiments, the aryl is anthracenyl, naphthyl, and phenyl.

In some embodiments, the heterocyclyl is aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydropyranyl, imidazolinyl, dihydropyranyl, azirinyl, oxirenyl, thiirenyl, diazirinyl, azetyl, oxetyl, thietyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, thiazepinyl 3-azabicyclo[3.1.0]hexanyl, 3-azabicyclo[3.1.1]heptanyl, 2-azaspiro[3.3]heptanyl, 2-oxa-6-azaspiro[3.3]heptanyl, or 5-azaspiro [2.3]hexanyl.

The present invention further provides a composition for use in dental tissue repair and/or regeneration wherein the composition comprises a modified succinic acid triacrylate compound comprising the chemical structure shown above (Formula II). Such modified succinic acid triacrylate compounds may have an enhanced ability to promote adhesion, migration, proliferation and/or differentiation of dental pulp stem cells (DPSCs), thus, further promoting dental tissue repair and/or regeneration. These compositions are suitable for use in the methods of the present invention as described below.

The present invention also provides a novel compound of Formular III, or a pharmaceutically acceptable salt thereof, comprising the structure:

[Formula III]

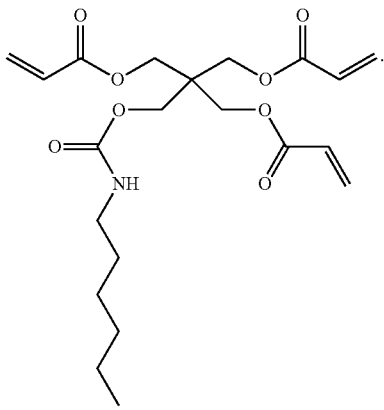

The present invention further provides compositions for use in dental tissue repair and/or regeneration wherein the compositions comprise a pentaerythitol triacrylate-4-((4-hydroxybutyl)amino)-4-oxobutanoic acid compound comprising the chemical structure of Formula III.

The present invention also provides a novel compound of Formular IV, or a pharmaceutically acceptable salt thereof, comprising the structure:

[Formula IV]

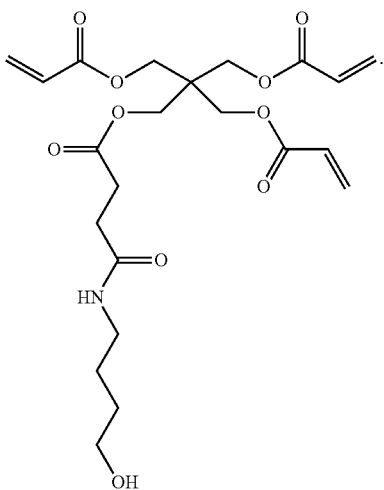

The present invention further provides compositions for use in dental tissue repair and/or regeneration wherein the compositions comprise a compound comprising the chemical structure of Formula IV. These compositions are suitable for use in the methods of the present invention as described below.

III. Methods of the Invention

The invention further provides methods for promoting dental tissue repair and/or regeneration in a subject in need thereof. The methods of the present invention include contacting the dental tissue with a composition comprising a triacrylate capable of promoting dental pulp stem cell (DPSC) adhesion and/or proliferation; and allowing DPSCs to adhere and/or proliferate, thereby promoting repair and/or regeneration of the dental tissue.

As used herein, the term "contacting" (e.g., contacting a dental tissue or a plurality of dental tissues with a composition) is intended to include any form of interaction (e.g., direct or indirect interaction) of a composition and a dental tissue or a plurality of dental tissues. Contacting a dental tissue or a plurality of dental tissues with a composition may be performed either in vivo or in vitro. In certain embodiments, the dental tissue or a plurality of dental tissues are contacted with the composition in vitro and subsequently transferred into a subject in an ex vivo method of administration. Contacting the dental tissue or a plurality of dental tissues with the composition in vivo may be done, for example, by injecting the composition into the dental tissue or a plurality of dental tissues, or by injecting the composition into another area adjacent to the dental tissue or a plurality of dental tissues, such that dental cells within the dental tissue or a plurality of dental tissues will travel towards the composition.

In certain embodiments of the invention, contacting a dental tissue or a plurality of dental tissues in vitro may be done by incubating the dental tissue or a plurality of dental tissues with a composition. In some embodiments, the in vitro contact may occur by incubating a dental tissue or a plurality of dental tissues with the composition for a period of time, such as, for example, about 1 hour, about 2 hours, about 4 hours, about 8 hours, about 24 hours, about 48 hours, about 72 hours, about 96 hours, about 120 hours, about 144 hours, about 168 hours, or longer than 168 hours, or ranges thereof.

The term "regeneration", as used herein, encompasses both regeneration of tissue with recourse to exactly the type of tissue to be regenerated, in the sense of an increase in the mass of the tissue, as well as the production of new tissue starting from a different type of tissue or cell than that to be produced. For example, the term "dental tissue regeneration" refers to the process by which new dental tissues from progenitor cells, such as stem cells, e.g., dental pulp stem cells.

Dental repair can encompass dental restoration, e.g., using a dental restoration material, e.g., comprising a composition described herein, e.g., a composition comprising a triacrylate described herein.

The methods of the present invention are suitable for repair and/or regeneration of any type of dental tissue including, but not limited to, a dental pulp tissue, a coronal pulp tissue, a radicular pulp tissue, a periapical tissue, a periapical connective tissue, a periodontal tissue, an accessory canal tissue, an apical foramen tissue, a foramina tissue, a Zone of Rinaggio tissue, a zone of Weil tissue, an odontoblastic layer, a bone tissue, a gum tissue, a blood vessel tissue, a nerve tissue, a nerve plexus of Raschkow tissue, a cementum tissue, a dentin tissue, a sclerotic dentin tissue, a tertiary dentin tissue, a reactionary dentin tissue, a reparative dentin tissue, a dentinal tubule tissue, a neodentin tissue, and any tissues associated with dental pulp containing any of ameloblasts, fibroblasts, odontoblasts, or immune cells including, but not limited to, histiocytes, macrophage, granulocytes, mast cells or plasma cells.

In some embodiments, the dental tissue is a dental pulp tissue. In other embodiments, the dental tissue is a dentin tissue.

In some embodiments, the compositions of the present invention can provide a substrate for the growth of cells or formation of tissue. In some embodiments, the compositions promote adhesion, migration, differentiation and/or proliferation of a dental tissue to repair and/or regenerate the dental tissue. In other embodiments, the composition is suitable for treating a dental infection in a subject in need thereof.

The methods of the present invention include contacting the dental tissue with a composition comprising a triacrylate capable of promoting dental pulp stem cell (DPSC) adhesion and or proliferation. The dental tissue can be contacted with the composition by any known routes in the art, e.g., by delivering the composition to a natural or artificial cavity or chamber of a tooth in a subject. As used herein, the term "delivery" refers to the placement of a composition into a subject by a method or route which results in at least partial localization of the composition at a desired site such that a desired effect is produced.

Exemplary modes of delivery include, but are not limited to, injection, insertion, implantation, or delivery within a scaffold that encapsulates the composition of the invention at the target tissue, e.g., dental tissue. In some embodiments, the composition is delivered to a natural or artificial cavity or chamber of a tooth of a subject by injection. When the compositions of the invention are dissolved in a solution, they can be injected into the dental tissue by a syringe.

In some embodiments, the compositions, e.g., triacrylates, may be delivered as a monomer, wherein the composition is polymerized upon delivering into a natural or artificial cavity or chamber of a tooth by in situ polymerization. In some embodiments, the triacrylate is polymerized by UV irradiation. In other embodiments, the compositions, e.g., triacrylates, may be delivered as a polymer, wherein the triacrylates are polymerized prior delivering into a natural or artificial cavity or chamber of a tooth.

In some embodiments, the compositions of the invention can alternatively be introduced into or onto a natural or artificial cavity or chamber of a tooth via a carrier based system, such as an encapsulation vehicle. For example, the compositions can be micro-encapsulated to provide for enhanced stability or prolonged delivery. Encapsulation vehicles include, but are not limited to, microparticles, liposomes, microspheres, or the like, or a combination of any of the above.

In yet another embodiment, the compositions of the present invention may further comprise a scaffold, wherein the composition is delivered into a natural or artificial cavity or chamber of a tooth within the scaffold. As described in section II above, the triacrylates may be chemically tethered to, or absorbed in the scaffold by methods known in the art. Alternatively, the scaffold may comprise a particle that encapsulates the triacrylates.

The methods of the present invention are suitable for dental tissue repair and/or regeneration in a subject, wherein the subject is a mammal. In some embodiments, a mammal is a primate, e.g., a human or an animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, a subject is selected from the group consisting of a human, a dog, a pig, a cow, a rabbit, a horse, a cat, a mouse and a rat. In preferred embodiments, the subject is a human.

The present invention further provides methods for promoting differentiation of dental pulp stem cells. The methods include contacting the dental pulp stem cells with a composition comprising a triacrylate capable of promoting dental pulp stem cells adhesion and/or proliferation, and allowing dental pulp stem cells to adhere and/or proliferate, thereby promoting differentiation of the dental pulp stem cells.

Dental pulp stem cells (DPSCs) are multi-potent stem cells derived from neural crest of a tooth pulp. DPSCs can be obtained from any tooth of any vertebrate that has teeth. In some embodiments, the dental pulp stem cell is derived from the pulp tissue from a baby tooth. In other embodiments, the dental pulp stem cell is derived from the pulp tissue from a premolar, a molar, an incisor or a canine.

The dental pulp stem cells can differentiate into a more mature and functional cell, for example, an odontoblast. As described herein, an odontoblast is a cell found in the oral cavity of a mammal that initiates the process of dentinogenesis, resulting in the formation of dentin. The dental pulp stem cells can produce a dentin and/or pulp tissue structure in vivo and in vitro.

The methods of the present invention may further include a step of assessing DPSC differentiation. Methods for measuring DPSC differentiation are well known in the art. For example, expression levels of DPSC differentiation markers can be measured to determine the state of DPSC differentiation.

Markers of DPSC differentiation are known in the art. Examples of such markers include, but are not limited to, BGLAP, DSPP, RUNX2, TGFB1, DMP1, ALP and SPP1. Expression levels of DPSC differentiation markers can be measured using RNA-based and/or protein-based assays.

The level of an mRNA encoding a marker can be measured using methods known to those skilled in the art, e.g. Northern analysis. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilizing ribonucleic acid hybridization include nuclear run-on assays, RT-PCR, RNase protection assays (Melton et al., *Nuc. Acids Res.* 12:7035), Northern blotting and In Situ hybridization. Gene expression can also be detected by microarray analysis.

For Northern blotting, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes.

In situ hybridization (ISH) is a powerful and versatile tool for the localization of specific mRNAs in cells or tissues. Hybridization of the probe takes place within the cell or tissue. Since cellular structure is maintained throughout the procedure, ISH provides information about the location of mRNA within the tissue sample. The procedure begins by fixing samples in neutral-buffered formalin, and embedding the tissue in paraffin. The samples are then sliced into thin sections and mounted onto microscope slides. (Alternatively, tissue can be sectioned frozen and post-fixed in paraformaldehyde.) After a series of washes to dewax and rehydrate the sections, a Proteinase K digestion is performed to increase probe accessibility, and a labeled probe is then hybridized to the sample sections. Radiolabeled probes are visualized with liquid film dried onto the slides, while nonisotopically labeled probes are conveniently detected with colorimetric or fluorescent reagents. This latter method of detection is the basis for Fluorescent In Situ Hybridisation (FISH).

Methods for detection which can be employed include radioactive labels, enzyme labels, chemiluminescent labels, fluorescent labels and other suitable labels.

Typically, RT-PCR is used to amplify RNA targets. In this process, the reverse transcriptase enzyme is used to convert RNA to complementary DNA (cDNA) which can then be amplified to facilitate detection. Relative quantitative RT-PCR involves amplifying an internal control simultaneously with the gene of interest. The internal control is used to normalize the samples. Once normalized, direct comparisons of relative abundance of a specific mRNA can be made across the samples. Commonly used internal controls include, for example, GAPDH, HPRT, actin and cyclophilin.

Expression of a marker of dental pulp stem cell differentiation can also be assessed at the protein level, using a detection reagent that detects the protein product encoded by the mRNA of the biomarker, directly or indirectly. For example, if an antibody reagent is available that binds specifically to a biomarker protein product to be detected, then such an antibody reagent can be used to detect the expression of the biomarker in a sample from the subject, using techniques, such as immunohistochemistry, ELISA, FACS analysis, and the like.

Other known methods for detecting the marker at the protein level include methods such as electrophoresis, capillary electrophoresis, high performance liquid chromatography (HPLC), thin layer chromatography (TLC), hyperdiffusion chromatography, and the like, or various immunological methods such as fluid or gel precipitation reactions, immunodiffusion (single or double), immunoelectrophoresis, radioimmunoassay (RIA), enzyme-linked immunosorbent assays (ELISAs), immunofluorescent assays, and Western blotting.

In one aspect, the present invention provides methods for treating periodontal disease e.g., a dental pulp infection, in a subject in need thereof. The methods include contacting a dental pulp tissue with a composition comprising a triacrylate capable of promoting dental pulp stem cell (DPSC) adhesion and/or proliferation; and regenerating dental pulp tissue by allowing DPSCs to adhere and/or proliferate; thereby treating the periodontal disease in the subject.

Periodontal diseases generally range from simple gum inflammation to serious disease that results in major damage to the soft tissue and bone that support the teeth. Periodontal disease results in loss of bony attachment to the root surface from chronic inflammation. Current treatment involves debriding the tissue to remove inflamed tissue. However the scaling involved in this procedure results in a loss of the cementum layer that connects the periodontal ligament from the bone to the root of the tooth. Thus, it is very difficult for the healed periodontal ligament to attach to the root after treatment. Triacrylates of the invention can be used as a varnish or coating on the roots of teeth to support re-attachment of the periodontal ligament after scaling and debridement.

In another aspect, the present invention provides methods for treating a dental infection, e.g., a dental pulp infection, in a subject in need thereof. Dental infections may arise from pulpitis, i.e., inflammation of the dental pulp tissue, which begins on the tooth's surface as dental caries. Dental infections may result in an exposure of pulp tissue, and eventually lead to a decay and/or loss of dentin and/or pulp, which are conventionally treated by endodontic surgery, e.g., root canal therapy.

Root canal therapy is commonly used in the case of severe caries where a substantial portion of the dentin and pulp tissue has been degraded, often into the vicinity of the root canal. During a root canal procedure, the entire pulp tissue (healthy or diseased), and some of the dentin are removed. Gutta-percha is used to fill the void formed in the root canal and coronal regions of the tooth, a resin or amalgam filing is used to replace the pulp, and often a metal or porcelain crown is cemented into place. As a result, root canal therapy completely devitalizes a tooth and hence terminates dentin formation. Unfortunately, the synthetic materials typically used to replace lost tooth structure are not capable of completely replacing the function of the lost tissue, and often fail over time making the tooth prone to fracture and subsequent loss.

Rather than destroying all remaining pulp tissue, the present invention eliminates the need for root canal therapy while preserving the remaining pulp and regenerating new dentin.

Indeed, the present invention provides methods for treating infection of a dental pulp in a subject in need thereof. The methods include contacting a dental pulp tissue with a composition comprising a triacrylate capable of promoting dental pulp stem cell (DPSC) adhesion and/or proliferation; and optionally, regenerating dental pulp tissue by allowing DPSCs to adhere and proliferate; thereby treating the dental pulp infection in the subject.

As described herein, infection of a dental pulp may result in exposure of dental pulp tissue. In certain embodiments, the dental tissue is contacted with the composition in vitro and subsequently transferred into a subject in an ex vivo method of administration. In other embodiments, the dental tissue is contacted with the composition in vivo, for example, by delivering the composition into or near the dental tissue by any methods as described herein.

Exemplary modes of delivery include, but are not limited to, injection, insertion, implantation, or delivery within a scaffold that encapsulates the composition of the invention at the target tissue, e.g., dental tissue. In some embodiments, the composition is delivered to a natural or artificial cavity or chamber of a tooth of a subject by injection. When the compositions of the invention are dissolved in a solution, they can be injected into the dental tissue by a syringe.

In other embodiments, the composition may be delivered as a triacrylate monomer, wherein the monomer is polymerized upon delivering into a natural or artificial cavity or chamber of a tooth by in situ polymerization. In some embodiments, the monomer is polymerized by UV irradiation. In other embodiments, the compositions, e.g., triacrylates, may be delivered as a polymer, wherein the triacrylates are polymerized prior delivering into a natural or artificial cavity or chamber of a tooth.

In some embodiments, the compositions of the invention can alternatively be introduced into or onto a natural or artificial cavity or chamber of a tooth via a carrier based system, such as an encapsulation vehicle. For example, the compositions can be micro-encapsulated to provide for enhanced stability or prolonged delivery. Encapsulation vehicles include, but are not limited to, microparticles, liposomes, microspheres, or the like, or a combination of any of the above to provide the desired release profile in varying proportions.

In yet another embodiment, the triacrylate composition of the present invention may further comprise a scaffold, wherein the composition is delivered into a natural or artificial cavity or chamber of a tooth within the scaffold. The triacrylate may be chemically tethered to, or absorbed in the scaffold by methods known in the art. Alternatively, the scaffold may comprise a particle that encapsulates the triacrylate. In some embodiments, the triacrylate may be released from the scaffold upon delivery at the target site.

In certain embodiments of the invention, contacting a dental tissue with a composition may occur for a period of time, such as, for example, about 1 hour, about 2 hours, about 4 hours, about 8 hours, about 24 hours, about 48 hours, about 72 hours, about 96 hours, about 120 hours, about 144 hours, about 168 hours, or longer than 168 hours. In some embodiments, the dental tissue is contacted with the composition for a sufficient period of time to allow cells from the exposed pulp tissue to migrate toward the composition, adhere and proliferate, thus regenerating the dentin and/or pulp tissue.

IV. Screening Assays

The invention also provides methods (also referred to herein as "screening assays") for identifying compounds, e.g., polymers, which promote dental tissue repair and/or regeneration. The present invention further provides methods for identifying a compound useful for treating a dental infection.

These methods generally include providing a plurality of dental pulp stem cells, and contacting the plurality of the dental pulp stem cells with a test compound. In certain aspects, the methods of the invention include determining the effect of a test compound (or a plurality of test compounds or a library of test compounds) on a biological activity of dental pulp stem cells, e.g., cell adhesion, using methods known in the art or described herein.

Compounds identified as increasing a biological activity of dental pulp stem cells, e.g., adhesion or differentiation, using the assays described herein are useful for, e.g., promoting dental tissue repair and/or regeneration and/or treating dental infections.

As used herein, the term "contacting" (i.e., contacting a cell e.g. a dental pulp stem cell, with a compound) includes incubating the compound and the cell together in vitro (e.g., adding the compound to cells in culture) as well as administering the compound to a subject such that the compound and cells of the subject are contacted in vivo.

The term "compound" or "test compound" includes reagents or test agents which are employed in the methods or assays are present in the compositions of the invention. The term "compound" or "test compound" includes compounds that have not previously been identified as, or recognized to be, agents that increase a biological activity of dental pulp stem cells, e.g., cell adhesion, are useful for promoting dental tissue repair and/or regeneration, or treating dental infections in a subject. In one embodiment, more than one compound, e.g., a plurality of compounds, can be tested at the same time in a screening assay for their ability to increase a biological activity of dental pulp stem cells, e.g., cell adhesion, to promote dental tissue repair and/or regeneration, or treat dental infections in a subject. The term "library of test compounds" refers to a panel comprising a multiplicity of test compounds.

Examples of compounds or test compounds include, but are not limited to, nucleic acids (e.g., DNA and RNA), carbohydrates, lipids, proteins, peptides, peptidomimetics, small molecules, polymers, naturally derived materials including ECM molecules, such as collagens and hyaluronic acid, polysaccharides such as alginate, agars, agarose and the like that can be formed into hydrogels, biocompatible synthetic materials including any of a variety of polymers or co-polymers, and other drugs. Compounds can be obtained using any of the numerous approaches in combinatorial library methods known in the art, for example: biological libraries; spatially addressable parallel solid phase or solution phase libraries; synthetic library; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des.* 12:145; U.S. Pat. Nos. 5,738,996; and 5,807,683, the entire contents of each of the foregoing references are incorporated herein by reference).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233, the entire contents of each of the foregoing references are incorporated herein by reference. Libraries of compounds may be presented, e.g., presented in solution (e.g., Houghten (1992) *Bio/Techniques* 13:412-421), or on beads (Lam (1991) *Nature* 354:82-84), plate, chips (Fodor (1993) *Nature* 364:555-556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865-1869) or phage (Scott and Smith (19900 *Science* 249:386-390; Devlin (1990) *Science* 249:404-406; Cwirla et al. (1990) *Proc. Natl. Acad. Sci. USA* 87:6378-6382; and Felici (1991) *J. Mol. Biol.* 222:301-310). The entire contents of each of the foregoing references are incorporated herein by reference.

In one embodiment, the ability of a test compound to increase a biological activity of dental pulp stem cells, e.g., cell adhesion, as compared to an appropriate control is measured in a screening assay of the invention.

An "appropriate control" or "suitable control" is any one or more controls or standards (positive and/or negative) familiar to one of ordinary skill in the art useful for comparison purposes. In some embodiments, a "suitable control" or "appropriate control" is a value, level, activity, determined in the absence of a test compound, as described herein. For example, a biological activity or read-out of such a biological activity may be determined in the presence and absence of a test compound. In other embodiments, a "suitable control" or "appropriate control" is a value, level, activity, determined in the presence of a compound that is known to have no effect on the biological activity of dental pulp stem cells, e.g., a negative control. In still other embodiments, a "suitable control" or "appropriate control" is a value, level, activity, determined in the presence of a compound that is known to have an effect on the biological activity of dental pulp stem cells, e.g., a positive control, so that the positive response can be compared to the unknown response of the test compound.

Different biological activities of dental pulp stem cells are suitable to be tested in the screening assays. For example, the effect of test compounds on dental pulp stem cell adhesion, proliferation, viability, and/or differentiation can be tested. Methods of performing the adhesion assays, proliferation assays, viability assays, and differentiation assays are known in the art. As demonstrated in Example 1 of the present invention, adhesion of dental pulp stem cells on various polymers were determined, and polymers that support dental pulp stem cells adhesion were identified.

In some embodiments, the methods of the invention comprise a combination of two or more of the assays described herein. For example, a compound that increase a biological activity of dental pulp stem cells, e.g., cell adhesion, can be identified using a cell-based assay, and the ability of the compound to modulate the expression and/or activity of a molecule involved in other biological activities of the dental pulp stem cells can also be determined. As demonstrated in Example 3 of the present invention, the selected test compound (or "compound of interest") from the adhesion assay were subsequently tested for their effect on dental pulp stem cell differentiation. Exemplified markers for dental pulp stem cell differentiation may include, but not limited to, BGLAP, DSPP, RUNX2, TGFB1, DMP1, ALP, SPP1, and any markers known in the art.

Accordingly, compounds identified in the subject screening assays can be used in methods of modulating one or more of the biological activities of dental pulp stem cells. Once a test compound is identified to increase a biological activity of dental pulp stem cells, e.g., cell adhesion, by one of the variety of methods described herein, the selected test compound (or "compound of interest") can then be further evaluated for its effect on additional activity of the cells, for example by contacting the compound of interest with cells either in vivo (e.g., by administering the compound of interest to a subject) or ex vivo (e.g., by isolating cells from the subject and contacting the isolated cells with the compound of interest or, alternatively, by contacting the compound of interest with a cell line) and determining the effect of the compound of interest on the cells, as compared to an appropriate control (such as untreated cells or cells treated with a control compound, or carrier, that does not modulate the biological response).

Compounds identified by the screening assays of the present invention are considered as candidate therapeutic compounds useful for treating diseases, e.g., dental infections, as described herein. Thus, the invention also includes compounds identified in the screening assays, and methods for their administration and use in the treatment, prevention, or delay of development or progression of diseases described herein.

V. Kits

The present invention also provides kits. Such kits can include a composition described herein and, in certain embodiments, instructions for administration. Such kits can facilitate performance of the methods described herein. When supplied as a kit, the different components of the composition can be packaged in separate containers and admixed immediately before use. Components include, but are not limited to a triacrylate, e.g., trimethylolpropane propoxylate triacrylate, trimethylolpropane triacrylate, pentaerythritol triacrylate, trimethylolpropane ethoxylate triacrylate, succinic acid triacrylate, a cell or a plurality of cells, e.g., dental pulp stem cells, a bioactive agent, e.g., an antibiotic, an anti-inflammatory, or any bioactive agent as described above; a scaffold, e.g., a hydrogel, or any other agents as described above. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

The kits of the invention may optionally comprise additional components useful for performing the methods of the invention. By way of example, the kits may comprise solutions for preparation of triacrylates, cell culture medium suitable for cells, e.g., dental stem pulp cells, one or more sample compartments.

In certain embodiments, kits can be supplied with instructional materials which describe performance of the methods of the invention. Kits may include instructions for in situ polymerization of monomers with crosslinking reagents, e.g., thiol-ene crosslinkers. In some embodiments, kits include instructions for culturing cells in vitro. In other embodiments, kits include instructions for administration or delivery of a composition to a tooth of a subject, e.g., a natural or artificial cavity or chamber of a tooth. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

The present invention is further illustrated by the following examples, which are not intended to be limiting in any way. The entire contents of all references, patents and published patent applications cited throughout this application, as well as the Figures, are hereby incorporated herein by reference.

EXAMPLES

Example 1. High Throughput Polymer Screen Using Polymer Microarrays

Polymer microarray allows simultaneous screening of diverse polymer chemistries to propel material discovery for biological applications. In order to identify novel biomaterials for improving dental treatment, a high-through screen polymer screen was performed using polymer microarrays (Anderson, D G et al., 2004, *Nature Biotechnology* 22, 863-866; Mei, Y et al., 2010, *Nature Materials* 9, 768-778; Celiz, A D, et al., 2015, *Advanced Materials* doi:10.1002/adma.201501351). DPSCs were procured from human donor teeth and expanded in tissue culture to be used in the experimental workflow, which involved screening, scaling up the materials to cell culture substrates, materials characterization, and biological characterization (FIG. 3A).

Briefly, 119 commercially available monomers of 250-400 μm diameter were printed and photo-polymerized on polyHEMA coated slides in microarrays (University of Nottingham), with six replicates per array. Monomers were polymerized by in situ polymerization with thiol-ene cross-linking upon ultraviolet (UV) irradiation (FIG. 7). Monomers and thiol-ene crosslinking reagents were presented at a molar ratio of 1.4:1. 1% w/v of photoinitiator was added to monomer solution. 400 μL of mixed monomer solution was added to each well of 12-well tissue culture plate. Each well was irradiated with 365 nm UV light for 5 minutes at an intensity of 20 mW/cm$^2$. UV-sterilized polymer coatings were left on plates for 30 minutes, then washed three times with Hanks' balanced salt solution (HBSS). Subsequently, polymer coatings were incubated in serum free alpha-MEM with ascorbic acid and penicillin/streptomycin for 48 hours. Plates were replaced with fresh media prior to addition of cells.

Human dental pulp stem cells (DPSCs) was passaged twice on tissue culture polystyrene (TCP) to enrich adherent DPSC population in complete media (alpha minimum essential media (MEM) with ascorbic acid, 20% fetal bovine serum, and 1% pencillin/streptomycin). Alternatively, DPSCs isolated from a donor's extracted third molar were passaged on TCP before seeding onto arrays. DPSCs were seeded at high (80,000 cells per array) and low seeding density (8,000 cells per array) on two arrays in serum-free media conditions (alpha MEM with 0.1 mM ascorbic acid and 1% penicillin/streptomycin at 37° C. under 5% $CO_2$). Cells were fixed with 4% paraformaldehyde (PFA), and stained with DAPI and phalloidin to determine cell adhesion. (FIG. 3B, scale bar=100 um). Automated-stage fluorescent imaging was performed with manual cell counting and image processing to quantify adhered cell number and cell area per polymer spot. The quantification of a combined area x count index yielded top-performing polymers identified as AT03 (trimethylolpropane triacrylate) and AT06 (pentaerythritol triacrylate) (FIG. 3C, black bars, statistically significantly different from overall mean, p<0.05, Kruskal-Wallis test with Dunn's multiple comparisons test, n=5 per marker).

Figure 3C:
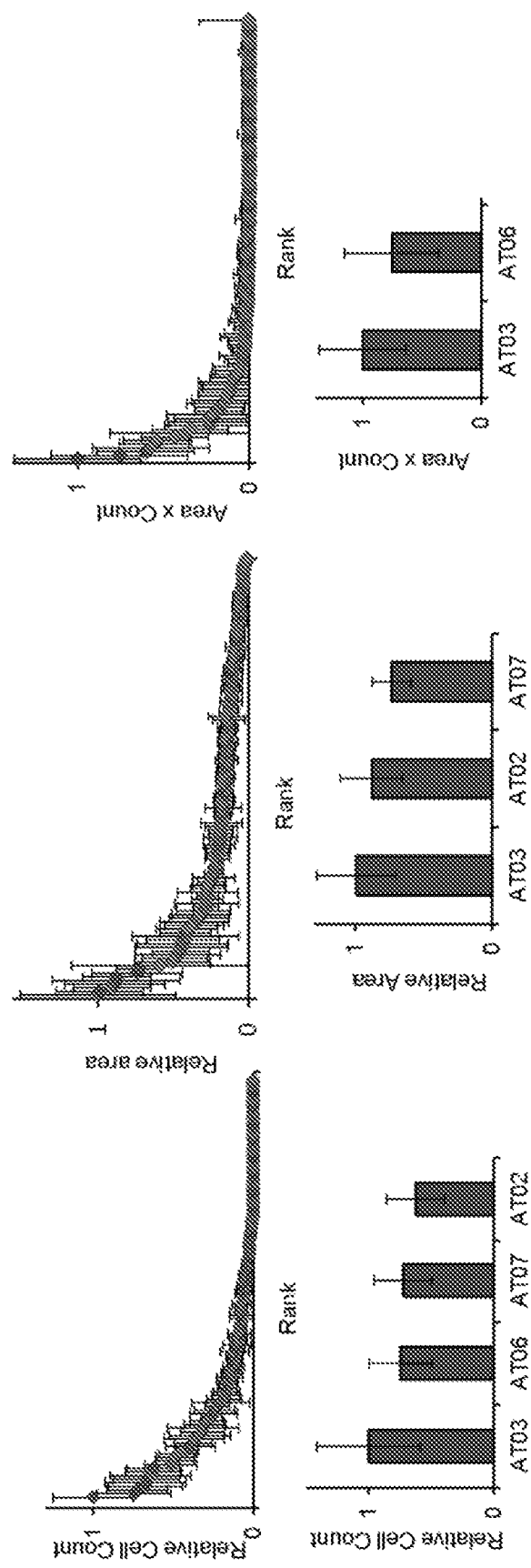

Fluorescence imaging and cell counting revealed polymer hits with mean cell numbers that are different from the overall mean cell number per spot (FIG. 3C). Out of those hits, three polymers, AT03 (trimethylolpropane triacrylate), AT06 (pentaerythritol triacrylate) and AT07 (trimethylolpropane ethoxylate triacrylate), demonstrated the highest relative DPSC adhesion after 48 hours (FIG. 4).

Remarkably, AT03 and AT06 were very consistent in chemical structure (FIGS. 5 and 6). Thus, thiol-ene chemistry was employed to scale up hit monomers AT03 and AT06 to bulk polymers, by adding a tri-thiol and photoinitiator (FIG. 8A). The thiol and triacrylates polymerize by both chain growth and network polymerization to yield fast curing in about 30 seconds, which was demonstrated by rheological measurements of the storage and loss moduli of AT03 (FIG. 8B). The storage modulus increased to 10 megapascals ($10^7$ Pa) by 60 seconds. The residual acrylate and thiol chemical groups were measured on the surface of the polymers by fourier-transform infrared spectroscopy, which showed significant attenuation of the acrylate and thiol peaks after curing (FIG. 8C). These data demonstrate that the triacrylates are suitable for in-situ curing, which is ideal for clinical applications in dentistry.

Methacrylate monomers are commonly used in dental fillings. The ability of DPSCs to adhere to trimethacrylates was assessed and compared with triacrylates. A trimethacrylate, BT01 (FIG. 9A), was generated in order to directly compare the behavior of DPSCs on triacrylates, AT03 and AT06, and trimethacrylate. BT01 was similarly polymerized with the tri-thiol. The mechanical properties of the resulting polymers were tested by compression and tension tests. The results demonstrate that the polymers yield similar compressive modulus of around 300 MPa. AT06 showed significantly higher tensile strength of close to 40 MPa, compared to a mean of between 20-30 MPa for BT01 and AT03 (FIG. 9B).

Example 2. DPSCS Adhere to Triacrylate Polymers and Proliferate in a J-Dependent Manner Subsequently, polymers AT03 (trimethylolpropane triacrylate) and AT06 (pentaerythritol triacrylate) were scaled up into 12-well plates for further testing on DPSC adhesion, proliferation and differentiation in vitro.

DPSCs were seeded at a density of 75,000 cells/cm$^2$ onto 12-well plates coated with polymers or tissue culture plastic control in serum-free conditions (alpha MEM with ascorbic acid and penicillin/streptomycin). Cells were adhered for 48 hours and imaged with phase contrast microscopy (FIG. 10A).

In order to determine the cell count and viability, plates were washed thoroughly with HBSS to remove non-adhered cells. Subsequently, cells were obtained from the surface by treatment of trypsin/EDTA for 5 minutes, followed by staining with Trypan blue and cell counting with the Countess Cell counter (Thermo). As demonstrated by FIGS. 10B and 10C, no statistically significant difference in cell count or percent viability was observed between cells when incubated on plates coated with AT03, AT06 and TCP (positive control), confirming the ability of AT03 and AT06 in supporting DPSCs adhesion.

DPSC cell count and phase images over 48 hours showed that DPSCs proliferate on the tissue culture plastic and triacrylate AT03, but not on trimethacrylate BT01 or control BisGMA, which is a methacrylate used in commercially available dental materials (FIG. 12A, scale bar 400 um). The cell counts on BisGMA were below the level of detection. Live-dead staining at 8 and 48 hours showed that cells adhered to AT03 are viable similar to TCP, but viable cells are significantly less on BT01 and BisGMA (FIG. 12B). Immunostaining for proliferation marker Ki67 and confocal microscopy showed that DPSCs on AT03 were positive for Ki67, which was consistent with the imaging and cell count data (FIG. 12C, F-actin green, Ki67 red).

To test whether integrin β1 receptor was required for the DPSCs to adhere to extracellular matrix that the cells expressed onto the triacrylates, an anti-β1 antibody was used to block the integrin β1 receptor subunit over the 48-hour experiment in serum-free media. FIGS. 12D and 12E showed that upon treatment of anti-β1 antibody, cells did not remain adhered on the triacrylates and BisGMA, while it had no significant effect on the tissue culture control. Together, these results demonstrate that DPSCs adhere and proliferate specifically on triacrylates in an integrin-β1-dependent manner.

Subsequently, expression levels of a wide range of genes associated with β1 signaling were measured in order to determine whether DPSCs on triacrylates express extracellular matrix that enables their adhesion via β1 signaling. Specifically, expression levels of commonly expressed matrix proteins collagen 1, collagen 2, collagen 4, and vitronectin were measured at 8 and 48 hours. FIG. 13B showed that COL1A1 expression is maintained on TCP and AT03, whereas COL4A4, COL2A1, and VN are increased on BisGMA and BT01. Furthermore, DPSCs on BisGMA and BT01 upregulated expression of genes associated with cell stress and survival, HRAS, SRC, and LEF1, compared to TCP and AT03 (FIG. 13C). These data suggest that collagen I expression is correlated with DPSC adhesion to the triacrylates, whereas conversely the cells that don't adhere well on BisGMA and BT01 compensate by upregulating other matrix genes and cell survival genes.

Example 3. Long-Term Culture and Differentiation of DPSCs on AT03 and AT06

To assess the ability of AT03 (trimethylolpropane triacrylate) and AT06 (pentaerythritol triacrylate) for supporting long-term cell culture and promoting DPSC differentiation, cells were treated with polymer coated plates for 21 days. Briefly, DPSCs were seeded at a density of 75,000 cells/cm$^2$ onto 12-well plates coated with polymers and TCP control in serum-free conditions (alpha MEM with ascorbic acid and penicillin/streptomycin). Media was changed every 2-3 days. Cells were imaged with phase contrast microscopy (FIG. 11A).

In order to determine the differentiation states of DPSCs, gene expression levels of several differentiation markers were measured by quantitative PCR. Cells were lysed for collecting RNA in RNA lysis buffer with 1% 2-mercaptoethanol to isolated RNA (PureLink RNA Micro Scale Kit, Thermo Scientific). RNA was quantified by NanoDrop spectrophotometer. Subsequently, cDNA was reverse transcribed by iScript™ Advanced Reverse Transcription Supermix for RT-qPCR (BioRad). Quantitative PCR was performed in duplicate with 10 ng of cDNA in each reaction on the BioRad CFX96 with AdvancedSSO SYBR® Green Supermix (BioRad) and PrimePCR primers (BioRad). Each qPCR measurement was repeated on at least three replicate samples. Relative gene expression was computed by the delta-delta Ct method, which compared Ct values to a control sample (Day 0) and reference gene (GAPDH). ANOVA and post-hoc statistical tests were performed on the log 2 transform of delta-Ct values to meet the assumption that the data follow a normal distribution. Data were normalized to a control sample at Day 0. Data were compared using two-way ANOVA with multiple comparisons test (N≥4, p<0.05). Values represent the mean and the standard error of the mean (SEM). As demonstrated in FIG. 11B, after 21 days of culture in serum-free conditions, AT03 and AT06 maintained lower levels of DPSC differentiation markers when compared to TCP positive control.

Surprisingly, when DPSCs were switched from serum-free media into differentiation media, gene expression levels of DPSC differentiation markers were changed significantly in both AT03 and AT06 coated plates. For this experiment, DPSCs were seeded at a density of 75,000 cells/cm$^2$ onto 12-well plates coated with polymers or TCP control in serum-free conditions (alpha MEM with ascorbic acid and penicillin/streptomycin). After cells were adhered and reached confluency over 72 hours, media was switched for differentiation conditions to differentiation media (alpha MEM with 10 mM beta-glycerophosphate, 10 nM dexamethasone, and 50 ug/mL (283.4 µM) ascorbic acid, 10% FBS). Similarly, media was changed every 2-3 days, and cells were imaged with phase contrast microscopy at Day 21 (FIG. 14A). Gene expression levels of different markers were determined by quantitative PCR as described above. Data were normalized to a control sample at Day 0, and compared using two-way ANOVA with Turkey post-hoc comparisons test (N=6, α=0.05). Values represent the mean and the standard error of the mean (SEM). FIG. 14B clearly demonstrated that both AT03 and AT06 stimulated a statistically significant increase in the expression levels of DPSC differentiation markers such as ALP and SPP1, when compared to TCP control after 21 days of culture in differentiation media. In some experiments, growth factor TGF-beta1 was added at 10 ng/mL to induce odontogenic differentiation. TGF-beta1 is known to regulate dentin regeneration. FIG. 16A shows how the addition of TGF-beta1 induced significant upregulation of gene expression of DSPP over 21 days in the TCP control, as well as AT06 and AT03. Under similar conditions without TGF-beta1, the cells do not express increased levels of DSPP (FIG. 16C).

Indeed, both ALP and SPP1 have been shown to be involved in reparative dentin formation. ALP, alkaline phosphatase, is a known marker for the detection of early osteogenic differentiation of cells, the expression of which is greatly enhanced during differentiation into osteogenic lineage (Chen C, et al., 2011 *Int Endod J;* 44:836-42). It is also an ectoenzyme involved in the degradation of inorganic pyrophosphate to release phosphate in the cytodifferentiation phase for mineralization; hence, it is a biological marker for bone turnover (Kulterer B, et al., 2007, *BMC Genomics* 8: 70). ALP is considered to play a key role in the mineralization of reparative dentin, and Col I is the predominant collagen in dentin that provides a structural framework for inorganic deposition. ALP and Col I are protein markers of early odontoblast development and are therefore associated with an intense secretory activity of the cell, whereas protein markers of late development (such as OCN) indicate that cells enter into a quiescent phase (Larmas M. 2008, *J Dent Res;* 87: 198).

SPP1, also known as secreted phosphoprotein 1, OPN, osteopontin is a multifunctional sialic acidrich phosphorylated glycoprotein highly expressed in the bone, teeth, and several pathologic calcification sites of soft tissues. SPP1 is an important middle-stage marker related both to bone formation and resorption, and recently Sodek et al. reported that SPP1 is also related to host defenses or tissue repair (Sodek J, et al., 2000 *Crit Rev Oral Biol Med;* 11: 279-303). Moreover, SPP1 contains several cell-adhesive domains, such as the integrin binding arginine-glysine-aspartate sequence, and thus mediates the cell-matrix interaction to cause adhesion, migration, and cytodifferentiation (Liaw L, et al., 1995 *J Clin Invest;* 95: 713-24).

In addition to alkaline phosphatase (ALP) and osteopontin (SPP1), DPSCs on AT03 and AT06 were shown to express markers of odontoblasts that produce dentin, dentin sialophosphoprotein (DSPP), with the addition of TGFβ1. Therefore, a significant increase in the expression levels of these DPSC differentiation markers further validated the finding that AT03 and AT06 were capable of both promoting DPSC adhesion and increasing DPSC differentiation, demonstrating that these biomaterials may have a great therapeutic potential to promote dentin regeneration in vivo by stimulating DPSC proliferation and differentiation.

Example 4. Comparison Between Existing Dental Polymer, AT03 and AT06 for DPSCs Adhesion Dental composite resins are types of synthetic resins which are used in dentistry as restorative material or adhesives. A commonly used dental composite is bisphenol A-glycidyl methacrylate (Bis-GMA). Bis-GMA is the reaction product of bisphenol A and glycidyl methacrylate that undergoes polymerization when exposed to ultraviolet light or mixed with a catalyst. It is used as a bond implant material and as the resin component of dental sealants and composite restorative materials.

The ability of exiting dental polymer, Bis-GMA, in promoting adhesion of DPSCs was tested and compared with AT03 (trimethylolpropane triacrylate) and AT06 (pentaerythritol triacrylate). Briefly, DPSCs were seeding onto 12-well plates coated with polymers or tissue culture plastic control in serum-free conditions (alpha MEM with ascorbic acid and penicillin/streptomycin). After 48 hours, the plates were washed with Hank's balanced salt solution (HBSS) to remove non-adhered cells, and remaining adhered cells were stained with calcein AM and ethidium homodimer-1 to characterize the live and dead cells, respectively. The labeled cells were imaged with phase contrast microscopy. As demonstrated in FIG. 15, no cells adhered to Bis-GMA coated surfaces, so they are not amenable for regenerative dental applications, whereas cells were clearly adhered when treated with AT03 and AT06 coated plates, suggesting that both AT03 and AT06 were more efficient than Bis-GMA in promoting DPSC adhesion, and are compatible with dental pulp stem cells. Accordingly, the triacrylates of the invention represent a novel biomaterial for improving dental treatments and can be practically used in a clinical context.

Example 5. AT03 for Treatment of Dental Pulp Injury

The clinical potential of using AT03 therapeutically in dentistry was demonstrated in a rodent model of dental pulp injury. 6-week year old male SD rats were anesthetized and surgery was performed on their first and second molars to partial resect the pulp tissue. This relates clinically to a partial pulpotomy in human patients, which is used to treat decay and pulp injury in pediatric patients. Hemostasis and drying of the tissue was obtained by pressure with cotton points. After proper isolation, the AT03-thiol prepolymer was applied to the cavity and cured inside the tooth (FIG. 17A). The control was application of a clinically used materials in dentistry a calcium hydroxide paste, dental adhesive, and a resin composite filling. Animals recovered from anesthesia and were sacrificed after 8 weeks. Dental tissues were properly fixed, imaged with microCT, and processed for histological hard tissue sectioning and staining. MicroCT images were processed to define the pulp volume and segment the mineralized opacities. Quantification of the dentin-to-pulp volume ratio showed no significant differences between conditions (FIG. 17B). Histologic sections showed that the pulp tissue became calcified and necrotic as a result of the partial pulpotomy, likely due to the severity of the surgical defect. The calcifications are consistent with reparative dentin formation. The AT03 biomaterial (white asterisks) was retained in contact with the pulp tissue after 8 weeks and the pulp tissue qualitatively appeared similar to the calcium hydroxide and resin composite control (black asterisk, FIG. 17C).

Together, these data demonstrate that the triacrylate successfully retains contact with pulp tissue after in-situ curing and supports pulp calcification after injury in a clinically-relevant setting of partial pulpotomy.

Example 6. Periodontal Ligament Fibroblasts Adhere to Triacrylate Polymers

The ability of triacrylate polymers AT03 and AT06 to adhere to primary human periodontal ligament fibroblasts was also tested. As shown in FIG. 18, triacrylate polymers AT03 and AT06 adhere to primary human periodontal ligament fibroblasts similar to tissue culture control (TCP). Human periodontal ligament fibroplasts (PDLFs) were obtained from extracted human teeth (Lonza) and cultured in stromal growth media (Lonza) for 2 passages. Cells were adhered on 12-well culture plates coated with AT03 and AT06, as well as a tissue culture plate control, in serum-free media at 25 k cells/cm$^2$. Phase images show confluent monolayers, scale bar 1 mm. Imaging and cell counts of viable cells were performed after 48 hours, and similar cell counts and percentage viability were observed for cells on AT03, AT06 and TCP control.

These data demonstrate that these triacrylate polymers are useful for periodontal applications. Periodontal disease results in loss of bony attachment to the root surface from chronic inflammation. Current treatment involves debriding the tissue to remove inflamed tissue. However the scaling involved in this procedure results in a loss of the cementum layer that connects the periodontal ligament from the bone to the root of the tooth. Thus, it is very difficult for the healed periodontal ligament to attach to the root after treatment. As demonstrated in this example, the triacrylates of the invention may be used as a varnish or coating on the roots of teeth to support re-attachment of the periodontal ligament after scaling and debridement.

Example 7. Application of Triacrylates for Cell Studies

Biological studies in vitro use polymer substrates to adhere and culture cells. Surface chemistry regulates how cells interact with these materials. Plasma-treated polystyrene is widely used in cell studies due it its ability to adsorb proteins, from serum and expressed by cells, which are required for cell adhesion and function. However, it is not well understood how treated-polystyrene affects the biology of the cells. Additionally, plasma treatment alters the surface chemistry by adding polar chemical groups in an uncontrolled manner and adds to manufacturing costs.

The present inventor surprisingly discovered that triacrylate materials are suitable as cell culture substrates, without any additional surface modifications. Cell culture plates were coated with triacrylates using "thiol-ene" polymerization. Briefly, all triacrylates were mixed with a multifunctional thiol, trimethylolpropane tris(3-mercaptopropionate), in a 1:0.5 molar ratio [acrylate:thiol] with photoinitiator, 2,2-Dimethoxy-2-phenylacetophenone (1% w/w), in the bulk and polymerized using UV light. In a typical experiment, an amber vial containing trimethylolpropane triacrylate (0.45 g, 1.5 mmol), trimethylolpropane tris(3-mercaptopropionate) (0.32 g, 0.8 mmol) and 2,2-dimethoxy-2-phenylacetophenone (7.7 mg, 0.03 mmol) was vortexed until homogenous. The "thiol-ene" polymerization solution was added to each well (50 uL) of a 12-well tissue culture treated plate to cover the surface of each well. The plate for subsequently exposed to UV for 5 minutes (10 mW/cm$^2$, 280 nm) to polymerize the solutions in-situ for subsequent in-vitro cell culture. Culturewares that are coated with the pre-polymer solution and are cured with UV light are highly scalable with commercial manufacturing.

Primary human dental pulp stem cells (DPSCs) adhere and function on triacrylate polymers similar to tissue culture-treated polystyrene, without cytotoxicity seen on methacrylate and trimethacrylate materials. Confluent monolayers of DPSCs require integrin β1 to remain adhered on triacrylates, as shown by loss of attachment with the addition of a blocking antibody, whereas cells on tissue culture plastic were not significantly affected by blocking β1. After culturing 21 days in differentiation induction media with TGFβ1, DPSCs expressed increased levels of differentiation markers compared to tissue culture plastic. Adherence to triacrylates was also observed by other cell types, such as primary human periodontal fibroblasts. These data demonstrate that triacrylates provide a more physiologic substrate for cells in vitro, without requiring additional surface treatments, compared with tissue culture plastic.

EQUIVALENTS

Those skilled in the art will recognize, or be able to ascertain using no more than routine experimentation, many equivalents to the specific embodiments of the invention described herein. such equivalents are intended to be encompassed by the following claims. The contents of all references, patents and published patent applications cited throughout this application are incorporated herein by reference.

We claim:

1. A composition for use in dental tissue repair and/or regeneration, comprising a triacrylate capable of promoting adhesion and/or proliferation of dental pulp stem cells (DPSCs); and a porous scaffold, wherein the scaffold comprises a particle that encapsulates the triacrylate, and wherein the scaffold comprises one or more pores having a diameter of about 50-500 μm.

2. The composition of claim 1, wherein the particle that encapsulates the triacrylate is selected from the group consisting of a microsphere, a liposome, a microparticle, or combinations thereof.

3. The composition of claim 1, wherein the scaffold comprises a hydrogel selected from the group consisting of collagen, alginate, polysaccharide, gelatin, chitosan, hyaluronic acid (HA), polyethylene glycol (PEG), poly(glycolide) (PGA), poly(L-lactide) (PLA), poly(lactide-co-glycolide) (PLGA), and polylactic-coglycolic acid.

4. The composition of claim 1, wherein the triacrylate is selected from the group consisting of trimethylolpropane propoxylate triacrylate, trimethylolpropane triacrylate, pentaerythritol triacrylate, trimethylolpropane ethoxylate triacrylate, succinic acid triacrylate and combinations thereof.

5. The composition of claim 1, wherein the triacrylate is modified triacrylate.

6. The composition of claim 5, wherein the triacrylate is a compound of Formula I, comprising the structure:

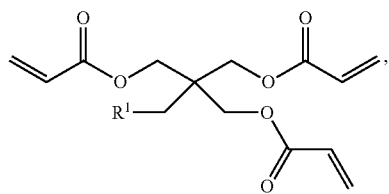

[Formula I]

or a pharmaceutically acceptable salt thereof;
wherein $R^1$ is selected from the group consisting of
—$COOR^a$, —$OCOR^a$, —$NR^aCOOR^a$, —$OCON(R^a)_2$, —$NR^bCOR^a$, —$CON(R^a)_2$, —$COR^a$ and —$NHCON(R^a)_2$;
$R^a$ is selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_2$-$C_{11}$heterocyclyl, $C_6$-$C_{14}$aryl, —$N(R^b)_2$, —$SR^b$, and —$OR^b$; wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_2$-$C_{11}$heterocyclyl, and $C_6$-$C_{14}$aryl groups are optionally substituted with one or four groups selected from the group consisting of hydrogen, halogen, hydroxy, cyano, amino, $C_1$-$C_{12}$alkyl, $C_1$-$C_{12}$alkoxy, $C_1$-$C_{12}$alkenyl, $C_1$-$C_{12}$alkynyl, $C_3$-$C_{12}$cycloalkyl, $C_2$-$C_{11}$heterocyclyl, $C_6$-$C_{14}$aryl, $C_1$-$C_{12}$alkylamino, di($C_1$-$C_{12}$alkyl)amino, —$COOR^c$, —$OCOR^c$, —$NR^cCOOR^c$, —$OCON(R^c)_2$, —$NR^cCOR^c$, —$CON(R^c)_2$, —$COR^c$ and —$NHCON(R^c)_2$;

$R^b$ is independently selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two $R^b$ groups may form a heterocyclyl with the nitrogen, oxygen, or sulfur to which they are connected, wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, amino, carboxy, $C_1$-$C_6$alkyl, $C_1$-$C_4$ carbonylamino, and $C_1$-$C_4$ alkoxy; and $R^c$ is independently selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two $R^c$ groups may form a heterocyclyl with the nitrogen or sulfur to which they are connected, wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, amino, carboxy, $C_1$-$C_6$alkyl, $C_1$-$C_4$ carbonylamino, and $C_1$-$C_4$ alkoxy.

7. The composition of claim 6, wherein $R^1$ is —$OCON(R^a)_2$;
wherein $R^a$ is selected from the group consisting of hydrogen and $C_1$-$C_8$alkyl; wherein the $C_1$-$C_6$alkyl is optionally substituted by one or four groups selected from halogen, hydroxy, amino, carboxy, $C_1$-$C_6$alkyl, $C_1$-$C_4$ carbonylamino, and $C_1$-$C_4$ alkoxy.

8. The composition of claim 6, wherein the compound is of the following structural formula, or a pharmaceutically acceptable salt thereof;

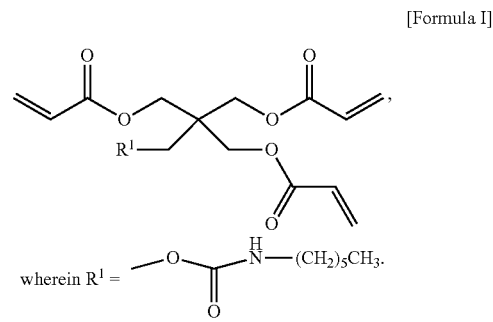

[Formula I]

wherein $R^1$ =

9. The composition of claim 6, wherein $R^1$ is —$OCOR^a$; wherein $R^a$ is selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_2$-$C_{11}$heterocyclyl, $C_6$-$C_{14}$aryl, —$N(R^b)_2$, —$SR^b$, and —$OR^b$; wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_2$-$C_{11}$heterocyclyl, and $C_6$-$C_{14}$aryl groups are optionally substituted with one or four groups selected from the group consisting of hydrogen, halogen, hydroxy, cyano, amino, $C_1$-$C_{12}$alkyl, $C_1$-$C_{12}$alkoxy, $C_1$-$C_{12}$alkenyl, $C_1$-$C_{12}$alkynyl, $C_3$-$C_{12}$cycloalkyl, $C_2$-$C_{11}$heterocyclyl, $C_6$-$C_{14}$aryl, $C_1$-$C_{12}$alkylamino, di($C_1$-$C_{12}$alkyl)amino, —COOR$^c$, —OCOR$^c$, —NR$^c$COOR$^c$, —OCON(R$^c$)$_2$, —NR$^c$COR$^c$, —CON(R$^c$)$_2$, —COR$^c$ and —NHCON(R$^c$)$_2$;

wherein R$^b$ is independently selected from the group consisting of hydrogen, $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two R$^b$ groups may form a heterocyclyl with the nitrogen, oxygen, or sulfur to which they are connected, wherein the $C_1$-$C_{12}$alkyl, $C_1$-$C_{12}$alkoxy, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, amino, carboxy, $C_1$-$C_6$alkyl, $C_1$-$C_4$ carbonylamino, and $C_1$-$C_4$ alkoxy; and R$^c$ is independently selected from the group consisting of hydrogen, halogen, $C_1$-$C_{12}$alkyl, $C_1$-$C_{12}$alkenyl, $C_1$-$C_{12}$alkynyl, $C_3$-$C_{12}$cycloalkyl, $C_2$-$C_{11}$heterocyclyl, and $C_6$-$C_{14}$aryl; wherein the $C_1$-$C_{12}$alkyl, $C_1$-$C_{12}$alkenyl, $C_1$-$C_{12}$alkynyl, $C_3$-$C_{12}$cycloalkyl, $C_2$-$C_{11}$heterocyclyl, and $C_6$-$C_{14}$aryl are optionally substituted from the group consisting of hydrogen, halogen, hydroxy, amino, carboxy, $C_1$-$C_4$ carbonylamino, and $C_1$-$C_4$ alkoxy.

10. The composition of claim 9, wherein the compound is of the following structural formula,

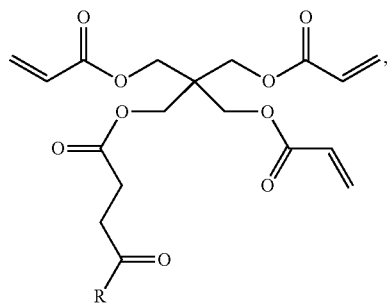

[Formula II]

or a pharmaceutical salt thereof; wherein

R is selected from the group consisting of hydrogen, bromo, iodo, fluoro, $C_1$-$C_{12}$alkyl, $C_2$-$C_{12}$alkenyl, $C_2$-$C_{12}$alkynyl, $C_3$-$C_{12}$cycloalkyl, $C_2$-$C_{11}$heterocyclyl, $C_6$-$C_{14}$aryl, —N(R$^d$)$_2$, —SR$^d$, and —OR$^e$; wherein the $C_1$-$C_{12}$alkyl, $C_2$-$C_{12}$alkenyl, $C_2$-$C_{12}$alkynyl, $C_3$-$C_{12}$cycloalkyl, $C_2$-$C_{11}$heterocyclyl, and $C_6$-$C_{14}$aryl groups are optionally substituted by one or more groups selected from the group consisting of halogen, hydroxy, cyano, amino, $C_1$-$C_{12}$alkyl, $C_1$-$C_{12}$alkenyl, $C_1$-$C_{12}$alkynyl, $C_1$-$C_{12}$alkoxy, $C_3$-$C_{12}$cycloalkyl, $C_2$-$C_{11}$heterocyclyl, $C_6$-$C_{14}$aryl, $C_1$-$C_{12}$alkylamino, and di($C_1$-$C_{12}$alkyl)amino;

R$^d$ is independently selected from the group consisting of hydrogen, $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl, or wherein the two R$^d$ groups may form a heterocyclyl with the nitrogen to which they are connected, wherein the $C_1$-$C_{12}$alkyl, $C_2$-$C_{12}$alkenyl, $C_2$-$C_{12}$alkynyl, $C_3$-$C_{12}$cycloalkyl, $C_6$-$C_{14}$aryl, and $C_2$-$C_{11}$heterocyclyl are optionally substituted by one of more groups selected from halogen, hydroxy, and $C_1$-$C_4$ alkoxy; and R$^e$ is independently selected from the group consisting of $C_2$-$C_{12}$alkyl, $C_2$-$C_{12}$alkenyl, $C_2$-$C_{12}$alkynyl, benzyl, and phenyl, wherein the $C_2$-$C_{12}$alkyl, $C_2$-$C_{12}$alkenyl, $C_2$-$C_{12}$alkynyl, benzyl, and phenyl are optionally substituted from the group consisting of halogen, hydroxy, and $C_1$-$C_4$ alkoxy.

11. The composition of claim 9, wherein the compound is of the following structural formula, or a pharmaceutically acceptable salt thereof;

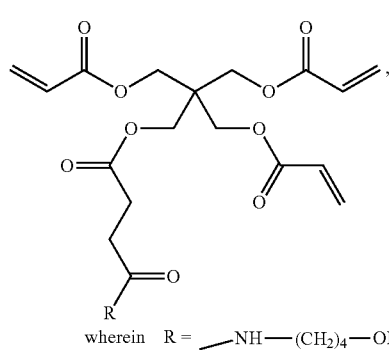

[Formula II]

wherein R = —NH—(CH$_2$)$_4$—OH.

12. The composition of claim 5, wherein modification of the triacrylate increases the ability of the triacrylate to promote adhesion, proliferation of dental pulp stem cells (DPSCs), and/or dental tissue repair and/or regeneration.

13. The composition of claim 1, wherein the composition further comprises a plurality of dental pulp stem cells (DPSCs).

14. The composition of claim 1, wherein the triacrylate is polymerized triacrylate.

15. A method for promoting dental tissue repair and/or regeneration promoting differentiation of dental pulp stem cells (DPSCs), and/or treating a dental pulp infection in a subject in need thereof, comprising:
   contacting the dental tissue with a composition of claim 1; and
   allowing DPSCs to adhere to the composition and/or proliferate, thereby promoting repair and/or regeneration of the dental tissue, promoting differentiation of dental pulp stem cells (DPSCs), and/or treating a dental pulp infection in the subject.

16. The method of claim 15, wherein the dental tissue is selected from the group consisting of a dental pulp tissue, a coronal pulp tissue, a radicular pulp tissue, a dentin tissue, a periapical tissue, a periapical connective tissue, a periodontal tissue, an accessory canal tissue, an apical foramen tissue, a foramina tissue, an odontoblastic layer, a bone tissue, a gum tissue, a blood vessel tissue, a nerve tissue, a cementum tissue, a neodentin tissue, and tissues associated with dental pulp comprising any of ameloblasts, fibroblasts, odontoblasts, histiocytes, macrophage, granulocytes mast cells or plasma cells.

17. The method of claim 15, wherein the triacrylate is selected from the group consisting of trimethylolpropane propoxylate triacrylate, trimethylolpropane triacrylate, pentaerythritol triacrylate, trimethylolpropane ethoxylate triacrylate, succinic acid triacrylate and combinations thereof.

18. The method of claim 15, wherein the subject is a human.

19. A kit comprising:
a composition of claim 1; and
instructions for delivery of the composition into a dental tissue of a subject to treat a dental condition in the subject.

* * * * *